US006300085B1

(12) United States Patent
Alkon

(10) Patent No.: US 6,300,085 B1
(45) Date of Patent: *Oct. 9, 2001

(54) DIAGNOSTIC METHOD FOR ALZHEIMER'S DISEASE

(75) Inventor: Daniel L. Alkon, Bethesda, MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,646

(22) PCT Filed: Sep. 26, 1995

(86) PCT No.: PCT/US95/12433

§ 371 Date: Jul. 18, 1997

§ 102(e) Date: Jul. 18, 1997

(87) PCT Pub. No.: WO96/10182

PCT Pub. Date: Apr. 4, 1996

Related U.S. Application Data

(63) Continuation-in-part of application No. 08/312,202, filed on Sep. 26, 1994, now Pat. No. 5,976,816, which is a continuation-in-part of application No. 08/056,456, filed on May 3, 1993, now Pat. No. 5,580,748.

(51) Int. Cl.[7] ........................... G01N 33/53; G01N 33/48
(52) U.S. Cl. ........................ 435/7.21; 436/63; 436/172; 436/811
(58) Field of Search ............................. 435/7.1, 7.21, 435/7.24, 7.92, 7.94, 7.95; 436/518, 528, 530, 531, 63, 811, 172

(56) References Cited

U.S. PATENT DOCUMENTS

| 4,925,664 | 5/1990 | Jackson et al. . |
| 5,580,748 | 12/1996 | Alkon et al. . |

FOREIGN PATENT DOCUMENTS

| 0344995 | 12/1989 | (EP) . |
| 9416327 | 7/1994 | (WO) . |
| 9425872 | 11/1994 | (WO) . |

OTHER PUBLICATIONS

R. Etcheberrigaray et al., *Soc. Neurosci Abstract,* vol. 18, Oct. 25–30, 1992 "Distinguishing Features of Potassium Channels in Fibroblasts From Alzheimer Aged and Young Donors".

D. Dewar et al., *Neurobiol. Aging.* vol. 13 (Suppl. 1), Jul. 12–17, 1992 "Multiple Ion Channel Binding Sites are Differentially Altered in Alzheimer's Disease Cortex".

M. Ikeda et al. *Brain Res.* vol. 567, pp. 51–56 (1991) "Selective Reduction of Iodine–125 Apamin Binding Sites in Alzheimer's Hippocampus: A Quantitative Autoradiographic Study".

R. Etcheberrigaray et al. *Proc. Nat'l Ac. Sciences,* vol. 89, pp. 7184–7188 (1992) "Classical Conditioning and Protein Kinase C Activation Regulate the Same Single Potassium Channel in Hermissenda Crassicornis Photoreceptors".

B. Sakmann and E. Neker, *Ann. Rev. Physiol.* vol. 46, pp. 455–472 (1984) "Patch Clamp Techniques For Studying Ionic Channels in Excitable Membranes".

E. Ito et al., *Neuroscience Research,* vol. 18: Abstract 615 (1993) "A Laboratory Diagnosis Of Alzheimer's Disease With Patch–Clamp and Ca2+—imaging techniques".

R. Etcheberrigaray et al., Proceedings Of The National Academy Of Sciences (USA) vol. 90, No. 17. 8209–8213 (1993) "Potassium channel dysfunction in fibroblasts indentifies patients with Alzheimer disease.".

E. Ito et al., Proceedings Of The National Academy Of Sciences (USA) vol. 91, No. 2, pp. 534–538 (1994) "Internal Ca2+ mobilization is altered in fibroblasts from patients with Alzheimer disease".

H.M. Huang et al., *Neurobiology Of Aging,* vol. 12: pp. 469–473 (1994) "Inositol Phosphates and Intracellular Calcium After Bradykinin Stimulation in Fibroblasts From Young, Normal Aged and Alzheimer Donors".

A. Grossmann et al., *Neurobiology Of Aging,* vol. 14, No. 2: 177–185 (1993) "Intracellular Calcium Response Is Reduced in CD4+ Lymphocytes in Alzheimer's Disease and in Older Persons with Down's Syndrome".

B. Sakmann et al., *Ann. Rev. Physiol.,* vol. 46: 455–472 (1984) "Patch Clamp Techiques for Studying Ionic Channels in Excitable Membranes".

C. Peterson et al., *Neurobiology Of Aging,* vol. 9, No. 3: 261–266 (1988) "Altered response of Fibroblasts From Aged and Alzheimer Donors to Drugs That Elevate Cytosolic Free Calcium".

A.F. Ghuysen–Itard et al., *Gerontology,* vol. 39:163–169 (1993) "Loss of Calcium–Homeostatic Mechanisms in Polymorphouclear Leukocytes of Demented and Nondemented Elderly Subjects".

(List continued on next page.)

*Primary Examiner*—Patricia A. Duffy
(74) *Attorney, Agent, or Firm*—Morgan & Finnegan LLP

(57) ABSTRACT

The present invention provides methods for the diagnosis of Alzheimer's disease using human cells. Specifically, one method detects differences between potassium channels in cells from Alzheimer's patient and normal donors, and differences in intracellular calcium concentrations between Alzheimer's and normal cells in response to chemicals known to increase intracellular calcium levels. Other methods detect differences between the memory associated GTP binding Cp20 protein levels between Alzheimer's and normal cells. In addition a diagnostic index for improved assessment between Alzheimer's and non Alzheimer's cells is provided.

13 Claims, 33 Drawing Sheets

OTHER PUBLICATIONS

A. Adunsky et al., *Journal of Neuroimmunology*, vol. 33:167–172 (1991) "Increased Cytosolic Free Calcium In Lymphocytes of Alzheimer Patients".

M. Ikdeda et al., *Brain Research*, vol. 567 51–56 (1991) "Selective Reduction of [$^{125}$I]apamin binding sites in Alzheimer Hippocampus: A Quanitive Autoradiographic Study".

D. Crespo et al., *Mechanisms of Aging and Development*, vol. 62:223–229 (1992) "The Influence of Age On Supraoptic Nucleus Neurons Of The Rat: Morphometric And Morphologic Changes".

Alkon et al., *J. Neurochem*, vol. 51:903 (1988), "Regulation of Hermissenda K+ channels by Cytoplasmic and Membrane–Associated C–Kinase".

J.T. Nearly et al., *Nature*, vol. 293:658 (1981), "Change In A Specific Phosphoprotein band Following Associative Learning In Hermissenda".

T.J. Nelson et al., *J. Neurochem*, vol. 57:2065 (1991), "Classical Conditioning–Induced Changes in Low–Molecular–Weight GTP–Binding Proteins in Rabbit Hippocampus".

Alkon et al., *PNAS* (USA) vol. 87:1611 (1990), "Contraction of Neuronal Branching Volume: An Anatomic Correlate of Pavlovian Conditioning".

S. Moshiach et al., *Brain Research*, vol. 605:298 (1993), "G–Protein Effects On Retrograde Axonal Transport".

T.J. Nelson et al., *Science*, vol. 247:1479 (1990), "Isolation of G Protein That is Modified by Learning and Reduces Potassium Counts in Hermissenda".

R. Etcheberrigaray et al., *Science*, vol. 264:276 (1994), "Soluble β–Amyloid Induction of Alzheimer's Phenotype for Human Fibroblast K+ Channels".

Lederhendler, I. Izja, et al. (1990) "Outgrowths From Hermissenda Photoreceptor Somata Are Associated With Activation Of Protein Kinase C" *Brain Research* 534:195–200.

Lederhendler, I. Izja, et al. (1991) "Outgrowths From Hermissenda Photoreceptor Somata Are Associated With Activation Of Protein Kinase C" *Nonmammalian Biochem* 114:451, #Abstract 39648Q.

Etcheberrigaray, et al. (1993) "New Implications Of Memory Mechanism For Alzheimer's Disease" *Neuroscience Research Communications* vol. 13:S7–S10.

Peterson et al. (1986) "Cytosolie Free Calcium and Cell Spreading Decrease in Fibroblasts from Aged and Alzheimer Donors" *Proc. Natl. Acad. Sci.* vol. 83:7999–8001.

Gunnerson et al. (1991) "Preliminary Characterization of a Novel Alzheimer Disease Asociated Protein" vol. 17:1–2 (#271.5).

Database WPI—Derwent Publications Led. London GB, AN 94–146876 JPA 06,009693 (Elken Kagakukk), Jan. 18, 1994 Abstract Only.

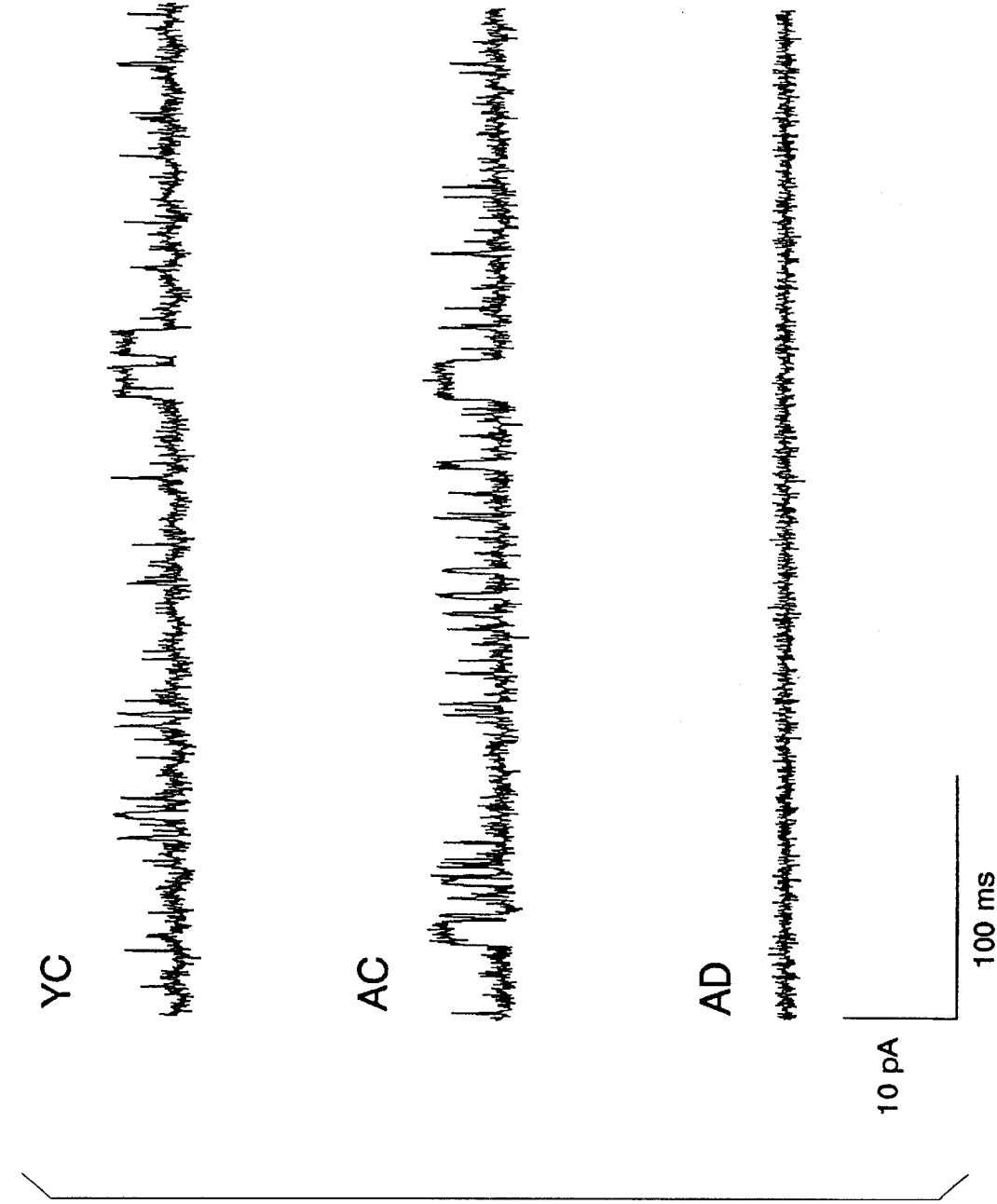

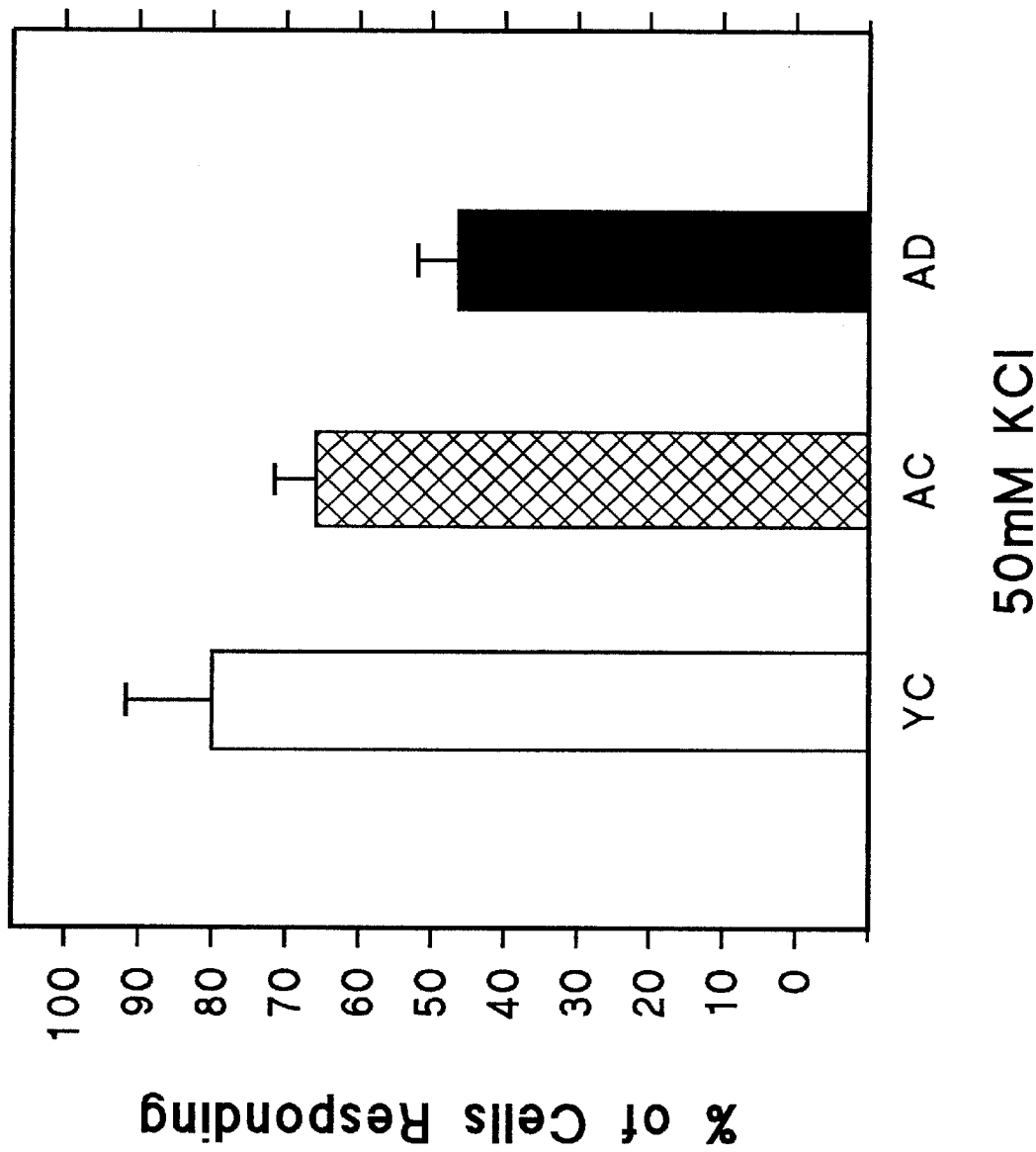

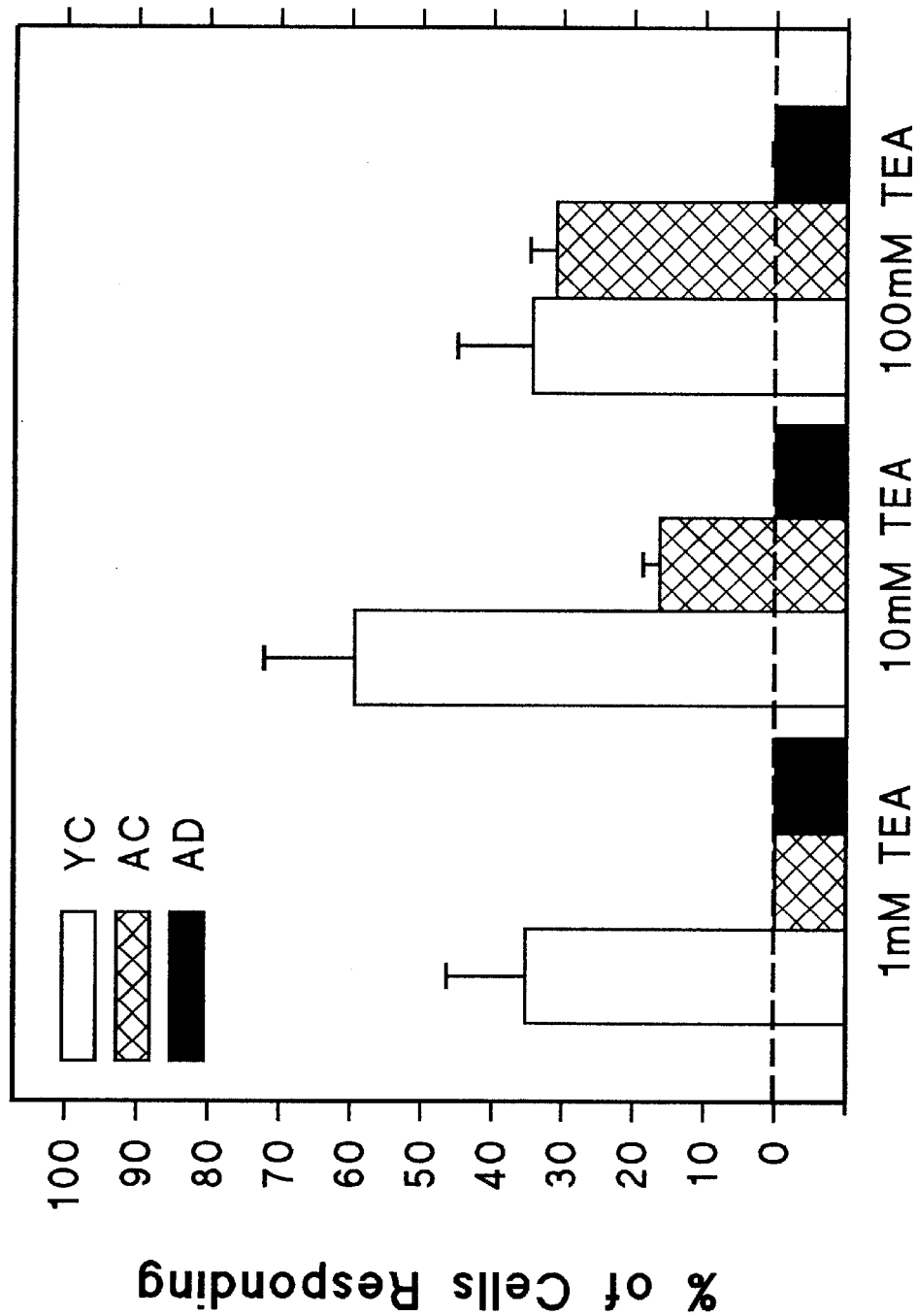

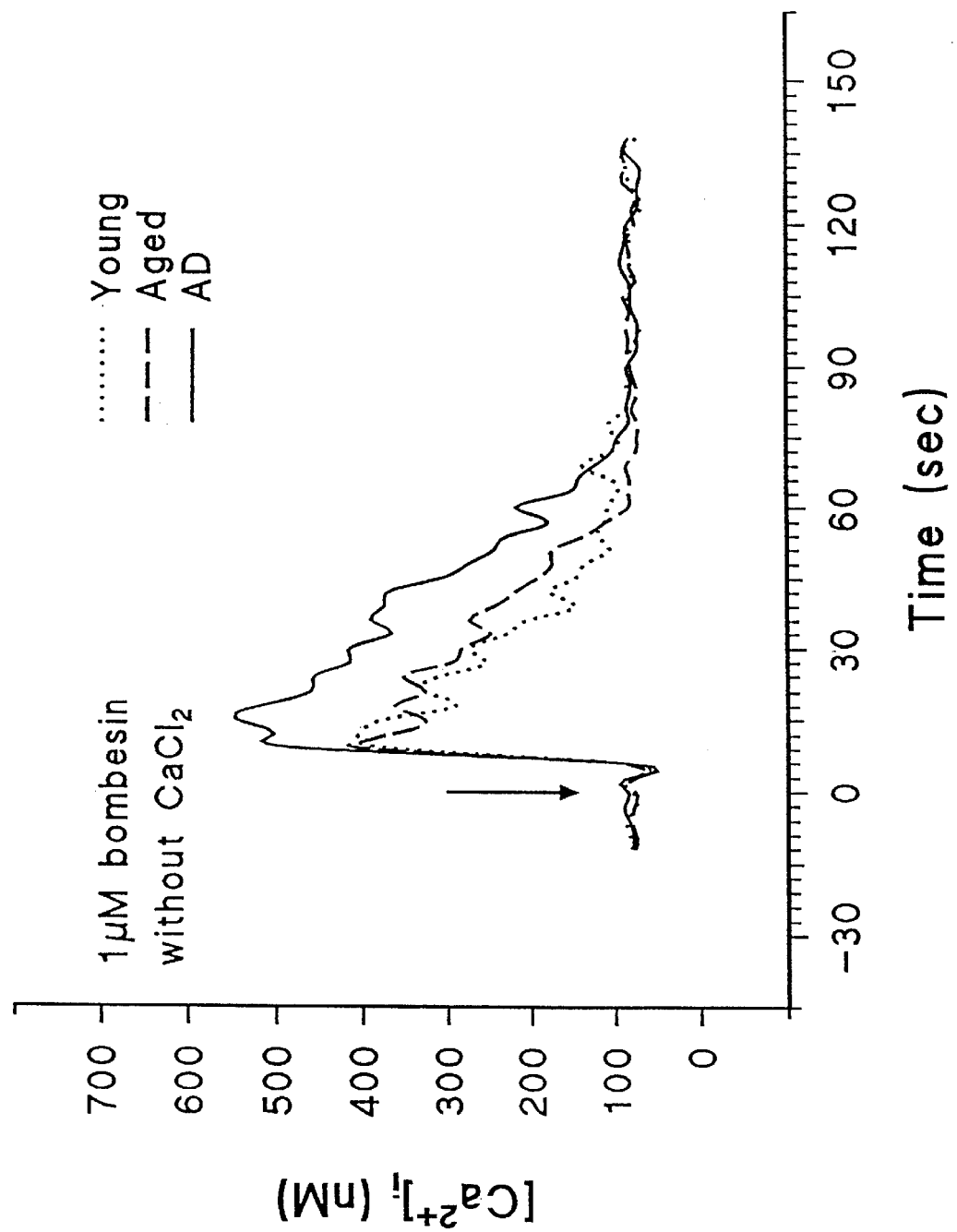

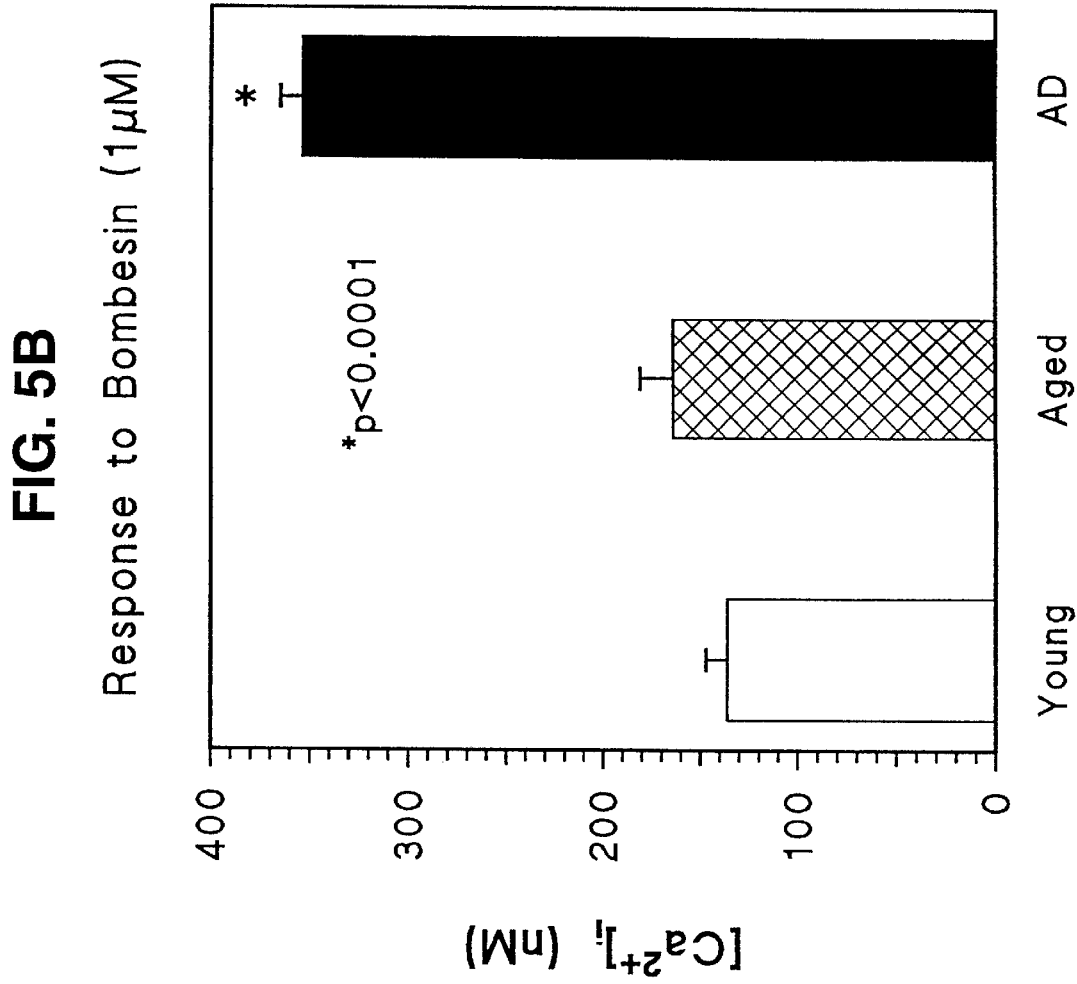

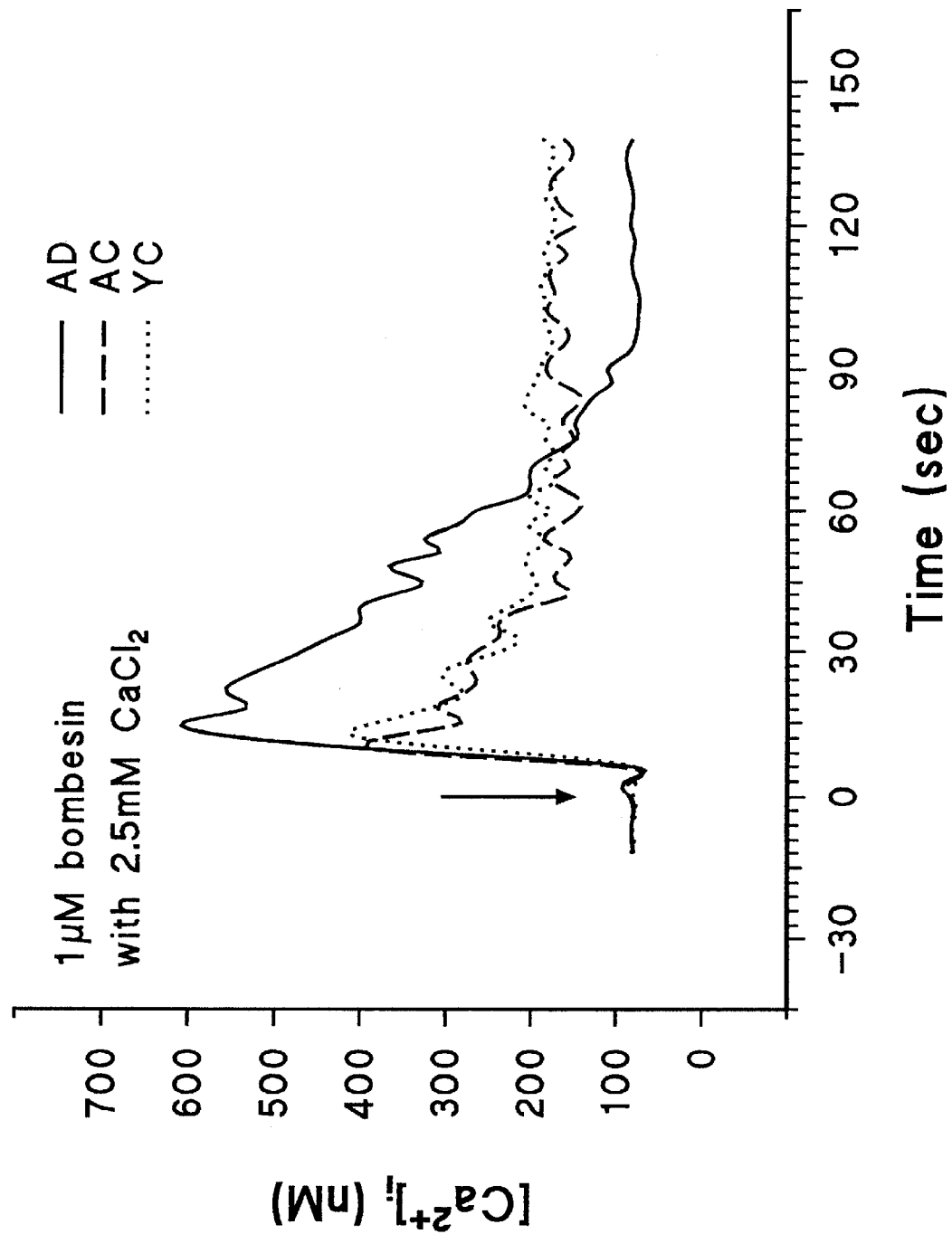

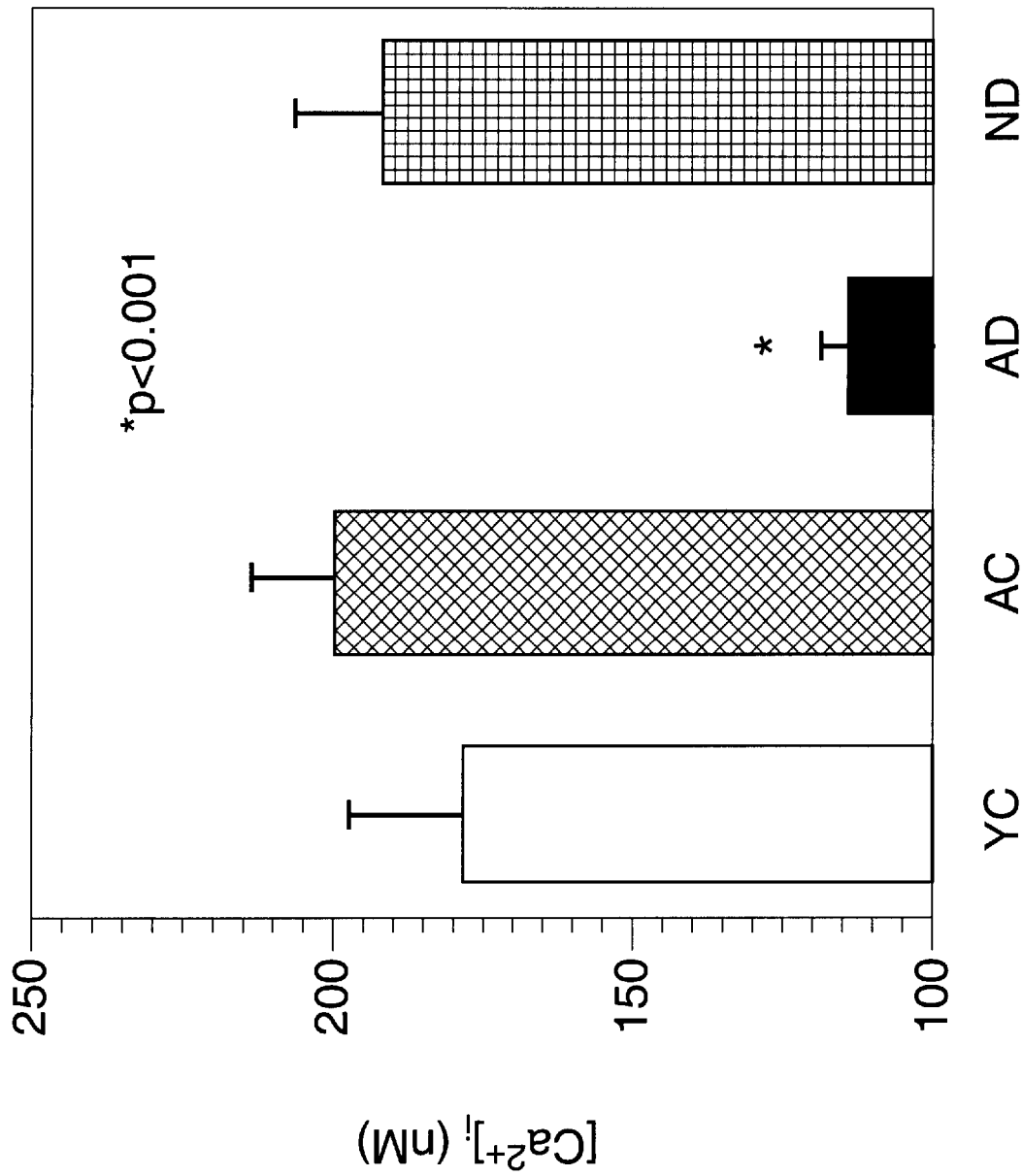

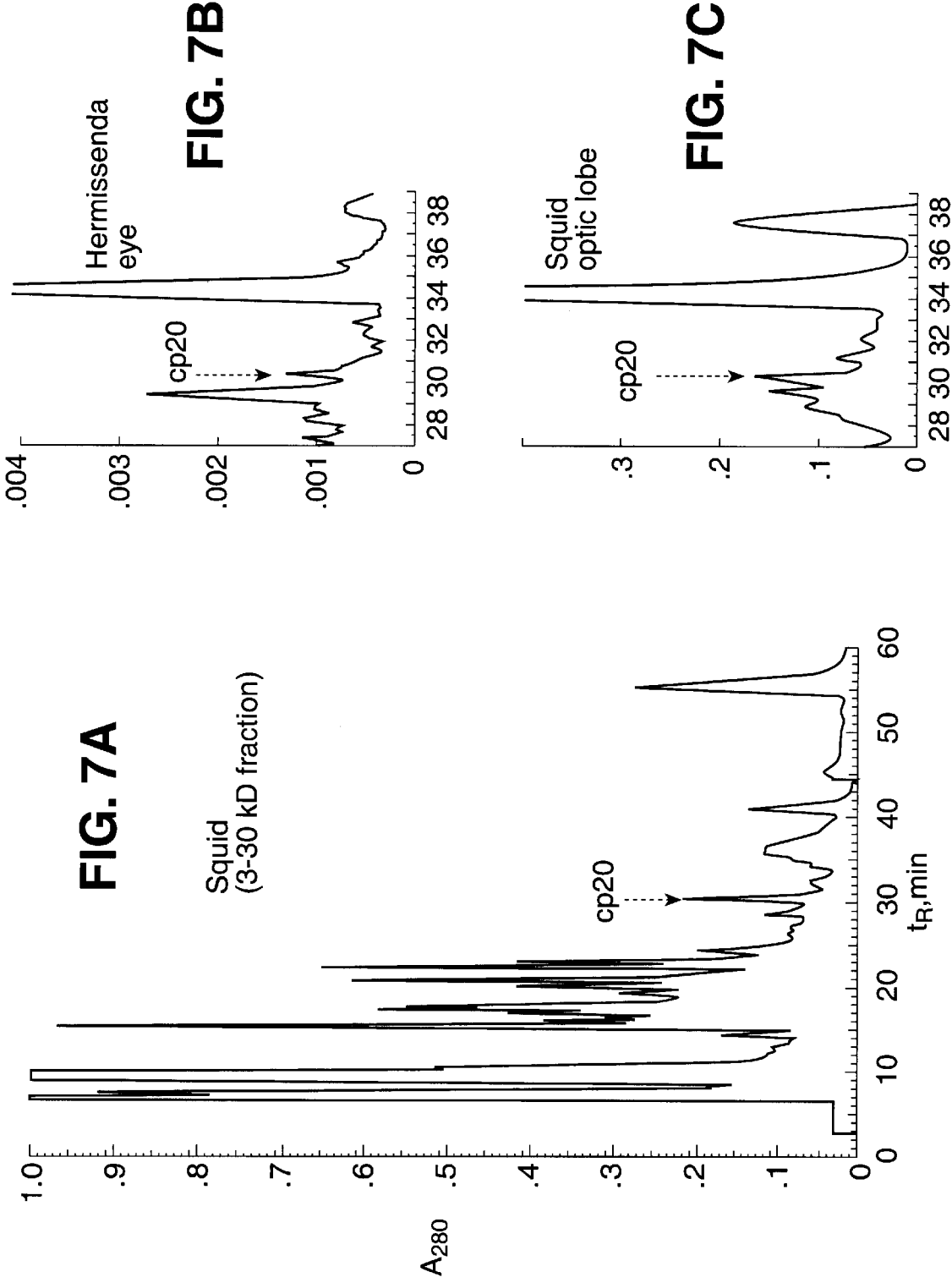

ARF

ARF
(contrasted-
enhanced)

Sar1p cp20

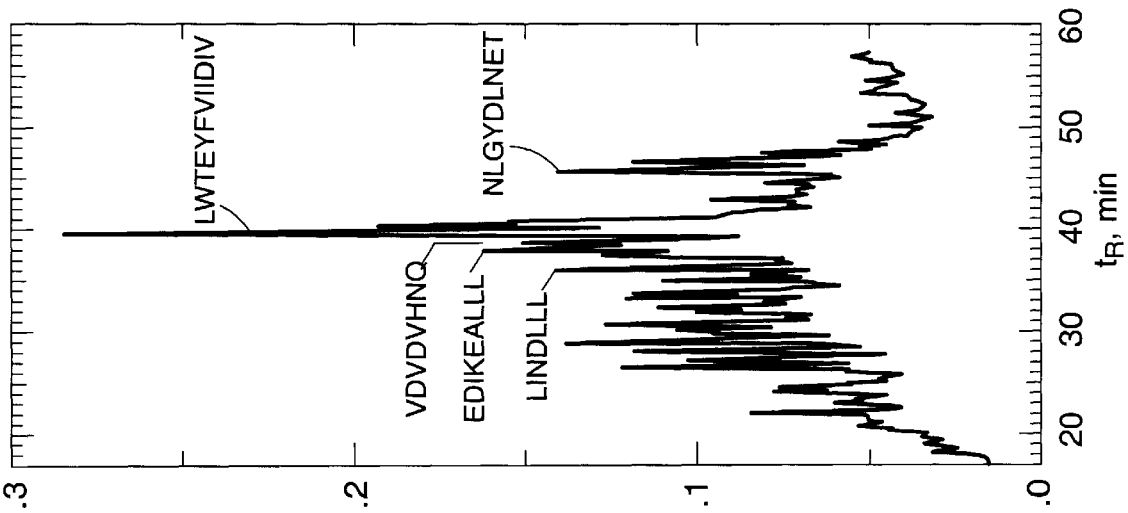

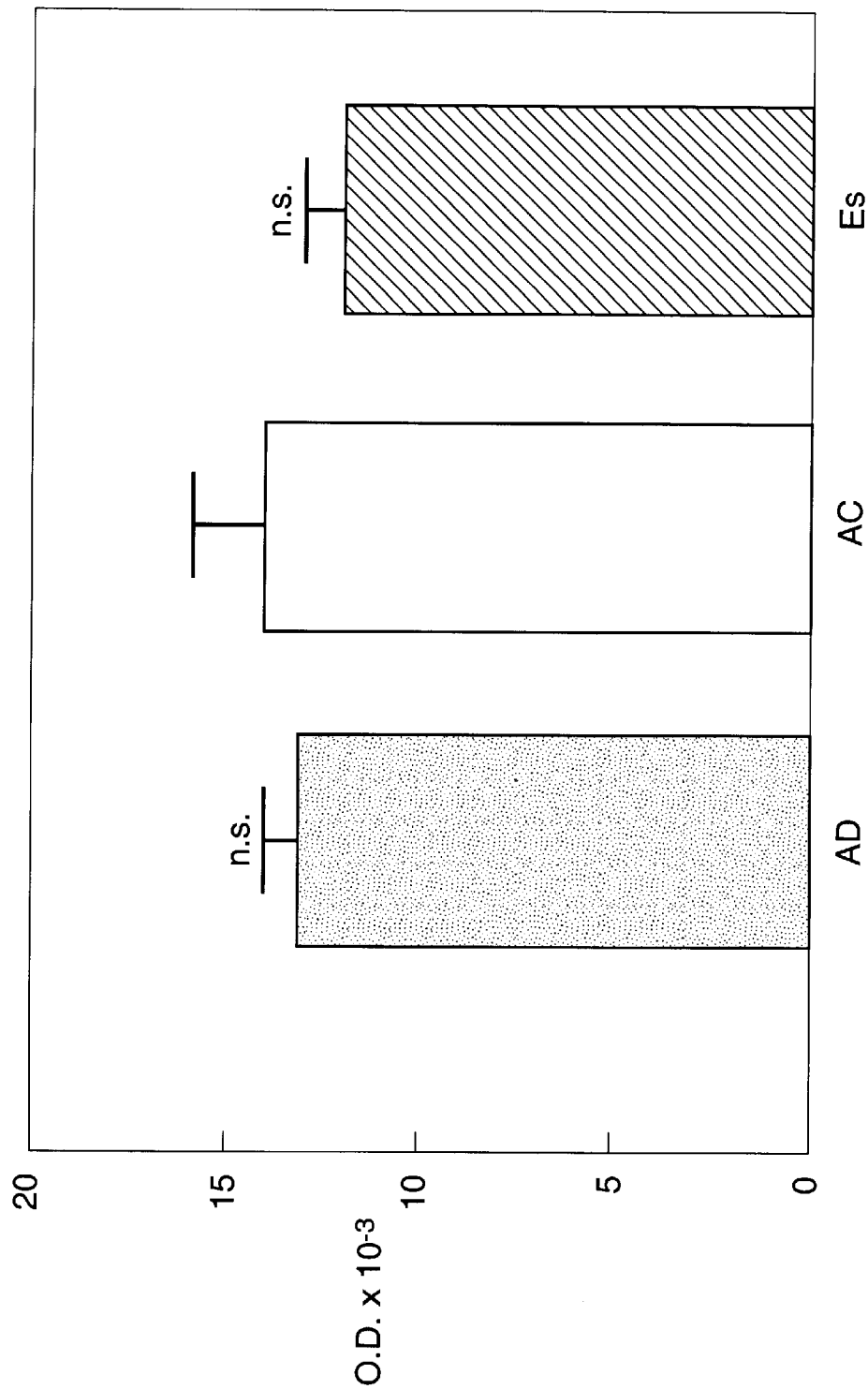

DIAGNOSTIC METHOD FOR ALZHEIMER'S DISEASE

This application is a continuation-in-part of U.S. patent application Ser. No. 08/312,202 filed Sep. 26, 1994, now U.S. Pat. No. 5,976,816 which is a continuation-in-part of U.S. patent application Ser. No. 08/056,456, filed May 3, 1993, now U.S. Pat. No. 5,580,748.

FIELD OF THE INVENTION

The present invention relates to methods for diagnosing Alzheimer's disease. The technique utilizes newly discovered differences between cells from healthy donors and those with Alzheimer's disease. In one method, differences in the existence of functional potassium channels are assessed. In another method, differences in intracellular calcium levels in response to depolarization by a potassium channel blocker are assessed. In yet another method, differences in intracellular calcium levels in response to a chemical known to increase intracellular calcium levels by releasing calcium from intracellular stores are assessed. In another method, differences in the levels of a memory associated GTP-binding protein (Cp20) between cells from healthy donors and Alzheimer's patients are assessed. This invention also relates to the amino acid sequence for the Cp20 protein. In addition diagnostic indexes that distinguish Alzheimer's patients' cells from control cells are also provided.

BACKGROUND OF THE INVENTION

Alzheimer's disease is associated with extensive loss of specific neuronal subpopulations in the brain (Sims, N. R., et al. (1987) *Annals of Neurology* 21:451), with memory loss being the most universal symptom. (Katzman, R. (1986) *New England Journal of Medicine* 314:964). Alzheimer's disease has been linked to a genetic origin. (Schellenberg, G. D., et al. (1992) *Science* 258:668; Li, G., et al. (1991) *Psychiatric Clinics of North America* 14:267; St. George-Hyslop, P. H., et al. (1989) *Neurobiology of Aging* 10:417; St. George-Hyslop, P. H., et al. (1987) *Science* 235:885). Early-onset familial forms of the disease exhibit a genetic defect on chromosome 21. (St. George-Hyslop, P. H., et al. (1987)).

Cellular changes, leading to neuronal loss and the underlying etiology of the disease, remain unknown. Proposed causes include environmental factors, (Perl, D. P. (1985) *Environmental Health Perspective* 63:149; Katzman, R. (1986)), including metal toxicity, (Perl, D. P., et al. (1980) *Science* 208:297), defects in β-amyloid protein metabolism, (Shoji, M., et al. (1992) *Science* 258:126; Joachim, C. L. and Selkoe, D. J. (1992) *Alzheimer Disease Assoc. Disord.* 6:7; Kosik, K. S. (1992) *Science* 256:780; Selkoe, D. J. (1991) *Neuron* 6:487; Hardy, H. and Allsop, D. (1991) *Trends in Pharmacological Science* 12:383), and abnormal calcium homeostasis and/or calcium activated kinases. (Mattson, M. P., et al. (1992) *Journal of Neuroscience* 12:376; Borden, L. A., et al. (1991) *Neurobiology of Aging* 13:33; Peterson, E., et al. (1989) *Annals of New York Academy of Science* 568:262; Peterson, C., et al. (1988) *Neurobiology of Aging* 9:261; Peterson, C., et al. (1986) *Proceedings of the National Academy of Science* 83:7999).

Alzheimer's disease is well characterized with regard to neuropathological changes. However, abnormalities have been reported in peripheral tissue supporting the possibility that Alzheimer's disease is a systemic disorder with pathology of the central nervous system being the most prominent. (Rizopoulos, E., et al. (1989) *Neurobiology of Aging* 10:717; Peterson (1986)).

Potassium channels have been found to change during memory storage. (Etcheberrigaray, R., et al. (1992) *Proceeding of the National Academy of Science* 89:7184; Sanchez-Andrés, J. V. and Alkon, D. L. (1991) *Journal of Neurobiology* 65:796; Collin, C., et al. (1988) *Biophysics Journal* 55:955; Alkon, D. L., et al. (1985) *Behavioral and Neural Biology* 44:278; Alkon, D. L. (1984) *Science* 226:1037). This observation, coupled with the almost universal symptom of memory loss in Alzheimer's patients, led to the investigation of potassium channel function as a possible site of Alzheimer's disease pathology and to the current invention.

The so-called patch clamp technique and improvements thereof, have been developed to study electrical currents in cells. The method is used to study ion transfer through channels. To measure these currents, the membrane of the cell is closely attached to the opening of the patch micropipette so that a very tight seal is achieved. This seal prevents current from leaking outside of the patch micropipette. The resulting high electrical resistance across the seal can be exploited to perform high resolution current measurements and apply voltages across the membrane. Different configurations of the patch clamp technique can be used. (Sakmann, B. and Neker, E. (1984) *Annual Review of Physiology* 46:455).

Currently, there is no laboratory diagnostic test for Alzheimer's disease. Therefore, there is a great need for a method to rapidly and clearly distinguish between Alzheimer's patients, normal aged people, and people suffering from other neurodegenerative diseases, such as Parkinson's, Huntington's chorea, Wernicke-Korsakoff or schizophrenia. Although some investigators have suggested that calcium imaging measurements in fibroblasts were of potential clinical use in diagnosing Alzheimer's disease (Peterson et al. 1986, 1988, supra), other researchers using similar cell lines and techniques, have shown no difference in calcium levels in Alzheimer's and normal control fibroblasts. (Borden et al. 1991, supra). Thus, the latter work refutes the findings of the former work.

The two proteins most consistently identified in the brains of patients with Alzheimer's disease have been β-amyloid and tau, whose roles in the physiology or pathophysiology of brain cells are not fully understood. However, there has been no diagnostic nor prognostic laboratory tests for Alzheimer's disease involving these or other proteins. Further, few other proteins have been identified which have physiological implications for Alzheimer's disease.

The methods for diagnosing Alzheimer's disease of the present invention using cells isolated from patients are needed and will greatly improve the now very complicated clinical diagnostic process for Alzheimer's disease. These methods are especially important because they are able to distinguish patients with Alzheimer's disease from patients with other neurodegenerative diseases.

SUMMARY OF THE INVENTION

The invention provides a method for assaying for Alzheimer's disease using cells isolated from patients. In one embodiment of the invention, the presence or absence of a particular potassium channel is measured. In a cell from a healthy control, potassium channels with slope conductances of 113 pS (picosiemens) and 166 pS are present and functional. In Alzheimer's cells, the 113 pS potassium channel is missing or nonfunctional.

In a second embodiment of the present invention, the effect of potassium channel blockers specific for the 113 pS potassium channel on intracellular calcium levels is assessed. In this method, intracellular calcium levels are found to be elevated in response to potassium channel blockers in normal cells, but not in cells from donors with Alzheimer's disease. The preferred potassium channel blocker is tetraethylammonium ("TEA") at a final extracellular concentration of 100 mM. However, other potassium channel blockers which specifically block the 113 pS potassium channel may also be used. Furthermore, when TEA is used, other final concentrations of TEA may be used as long as the level of TEA causes intracellular calcium levels to be elevated in normal cells, but not in cells from donors with Alzheimer's disease.

In a third embodiment of the invention, sample cells from a patient are contacted with an activator of intracellular calcium release, in an amount sufficient to release calcium from intracellular storage sites, and the resulting increase in intracellular calcium levels is measured. In this embodiment, both normal cells and cells from Alzheimer's patients exhibit an increase in intracellular calcium; however, the increase in Alzheimer's patients is much greater. When an inositol-1,4,5,-trisphosphate ($IP_3$) activator is used to increase intracellular calcium levels, the preferred embodiment utilizes bombesin added to a final extracellular concentration of 1 μm. However, other final concentrations can be used.

As shown in the examples, the combination of the second and third embodiments of the invention can be used in series to provide a very accurate method of diagnosing AD, with no false positives or false negatives. Furthermore, these methods are able to distinguish patients with Alzheimer's disease from patients with other neurodegenerative diseases. Cells from patients with Parkinson's disease, schizophrenia, Huntington's chorea, and Wernicke-Korsakoff exhibit responses of normal cells when treated with either TEA or bombesin.

In a fourth embodiment of the invention, the level of the memory associated GTP-binding protein (Cp20) in cells from an Alzheimer's disease patient is assessed. In this method, the Cp20 protein levels are found to be significantly reduced in cells from Alzheimer's disease patients relative to cells from healthy controls. Cp20 protein levels are also reduced in the cells of close relatives of the Alzheimer's disease patients, suggesting a prognostic use for this assay as well.

It is not known at the present time if the defects detected by the methods of this invention appear prior to or concurrently with the clinical onset of Alzheimer's disease. However, if the former is true, it is anticipated that the methods of this invention will have predictive as well as diagnostic utility in the detection of Alzheimer's disease.

The present invention also provides a partial amino acid sequence for the Cp20 protein. Therefore, this invention also extends to products derived using the amino acid sequence and useful for carrying out the Cp20 diagnostic assay, such as nucleic acid probes, or monoclonal or polyclonal antibodies reactive with the Cp20 protein.

This invention also extends to kits comprising products useful for carrying out the Cp20 diagnostic assay such as DNA probes, antibodies, kits and the like.

In yet another embodiment of this invention a diagnostic index utilizing two or more of the diagnostic tests described herein is provided that increases the probability of distinguishing Alzheimer's patient cells from non-AD cells.

BRIEF DESCRIPTION OF THE FIGURES

FIGS. 1A–1B. 113 pS channel. (1A). Cell attached recordings from Alzheimer and control fibroblasts. A potassium channel of ~4.5 pA unitary current size (0 mV pipette potential), with identical kinetics appeared in age-matched control (AC) and young controls (YC) fibroblasts, but was entirely absent in the recording of AD fibroblasts (1A, bottom) Downward deflections represent the open state. (1B). I/V relationships and slope conductances. I/V relationships and slope conductances (determined by linear regression) were almost identical within the voltage range explored, 113.2±0.9 pS (mean±S.D., n=8) for YC and 112.9±3.2 pS (n=7) for AC fibroblasts.

FIGS. 3A–3C. (3A) and (3B). Percent of cells responding to the addition of 50 mM potassium chloride and average $[Ca^{2+}]_i$ (nM) of responding cells. High potassium-induced depolarization caused $[Ca^{2+}]_i$ elevation (at least 100% increase) in all three groups (AD N=13 cell lines; AC N=10, YC N=6). The proportion of responding cells and the $[Ca^{2+}]_i$ peak values were significantly higher in YC (n=183 cells) fibroblasts ($\chi^2$=14.22, p<0.001), as compared to AC (n=299) and AD (n=268) fibroblasts (3A and 3B). (3C). Sample traces of time courses of the $Ca^{2+}$ response in cells after the addition of 50 mM KCl. The $[Ca^{2+}]_i$ peak occurs 10 to 15 seconds after stimulation, returning to basal levels after 100 seconds. No responses were observed if external $[Ca^{2+}]$ was lowered ["nominally $Ca^{2+}$ free" solution, 5 mM EGTA was added (estimated free $Ca^{2+}$=0.04 μM)], or $Ca^{2+}$ channel blockers (0.1 mM $LaCl_3$, 10 mM $CoCl_2$, 10 mM $NiCl_2$, 10 mM $CdCl_2$ or 10 μM nifedipine) were added before stimulation ("0 $Ca^{2+}$").

FIGS. 4A–4C. $[Ca^{2+}]_i$ elevation in response to TEA. (4A) Percentage of cells responding to the addition of TEA and (4B) Average $[Ca^{2+}]_i$ response in the cells after TEA treatment. 1 mM TEA application elevated $[Ca^{2+}]_i$ in YC fibroblasts (n=130 cells) but not in AC (n=184) or AD fibroblasts (n=195). 10 mM TEA elevated $[Ca^{2+}]_i$ in YC (n=176 cells), AC (n=231), but not in AD (n=204) fibroblasts ($\chi$134.00, p<0.001). Similarly, 100 mM TEA elevated $[Ca^{2+}]_i$ in YC (n=532 cells), AC (n=417), but not in AD (n=738) fibroblasts, $X^2$231.44, p<0.001 (also see Table 2). Basal $[Ca^{2+}]_i$ levels were virtually the same (S.E.<2 nM), therefore, standard error bars are not distinguishable from the bar representing the arithmetic mean for those groups. (4C). Time course of $Ca^{2+}$ responses. The $[Ca^{2+}]_i$ peak occurs 20 to 30 seconds after 100 mM TEA addition in YC and AC fibroblasts, returning to basal levels after 100 seconds. Note that no response meeting criterion (10% of cells in a line with ≧100% elevation) was observed in AD cells. Similarly, the response was absent in control cells when external $[Ca^{2+}]$ was lowered.

FIGS. 5A–5B. (5A). $Ca^{2+}$ mobilization induced by 1 μm bombesin in the absence of extracellular calcium. (5B). $Ca^{2+}$ responses at 42 sec after 1 μM bombesin application. The $[Ca^{2+}]_i$ levels in AD cells are much larger than in AC and YC cells. The numbers of cell lines (N) are 9, 8 and 6 for AD, AC and YC, respectively. The values are means±S.E.M.

FIGS. 6A–6B. (6A). $Ca^{2+}$ responses induced by 1 μm bombesin in the presence of extracellular calcium. 1 μm bombesin elicited a fast peak of $[Ca^{2+}]_i$, followed by a sustained phase for YC and AC cells, but not for AD cells, in the presence of extracellular 2.5 mM $CaCl_2$. The arrow indicates drug application. (6B). Bar graph illustrating differences evident 90 seconds after bombesin application. In the presence of normal extracellular calcium (2.5 mM), a sustained calcium entry follows the initial bombesin response in control cells but is completely absent in AD fibroblasts. The difference evident 90 seconds after bombesin application is shown and has a significance level of $p<0.001$.

FIGS. 7A–7D. $A_{280}$ HPLC tracings of proteins from Hermissenda eye (7B), squid optic lobe (7C) and squid 3–30 kDa fraction (7A). 36 eyes from Hermissenda trained to associate light rotation, or 1/10 squid optic lobe were analyzed by anion exchange HPLC as described in the text. In unconditioned Hermissenda, the cp20 peak (arrow) is 3–4 times smaller than the cp20 peak from conditioned animals shown here. (7D) Correlation curve of $t_R$'s from HPLC tracing from squid optic lobe proteins vs. $t_R$'s (retention times) from reference chromatogram of proteins from trained Hermissenda eye.

FIGS. 12A–12B. (12A) Sequence of cp20 (SEQ. ID. NO. 1) tryptic peptides and other proteins. The top sequence is a consensus of sequences of the same peptide from three different batches of cp20. The corresponding regions in the Giα (SEQ. ID.NO. 4) (Michel T., et al. (1986) Proc. Nat. Acad. Sci. USA 7663–7667.), ras (SEQ. ID. NO. 5) (Santos E., Nebreda A. R. (1989) FASEB J. 3, 2151–2163.), rab (SEQ. ID. NO. 6) (Zahraoui A., et al. (1989) J. Biol. Chem. 264, 12394–12301.), sec4 (SEQ. ID. NO. 7) (Salminen A., Novick P. J. (1987) Cell 49, 527–538.), and Drosophila Goα (SEQ. ID. NO. 8) sequence (Schmidt C. J., et al. (1989) Cell Regul. 1, 125–134.) are shown. (12B) RP-HPLC $A_{214}$ profile of a tryptic digest of cp20.

FIGS. 14A–14B. Coomassie stained protein gels of AD, Es, and AC fibroblasts. (14A) SDS-Page gels showing the protein profiles in all three groups studied. Three regions were analyzed in detail in order to detect generalized protein changes in AD and Es fibroblasts, with particular attention to the protein bands with molecular weights similar to Cp20 (≈20 kD). (14B) Quantitative analysis (graph) of the Cp20 region confirmed visual impressions that there are no between group differences around the 20 kD region. Similar analysis also showed no between-group differences of proteins with MW of 66 to 36 kD and in the 200 kD molecular weight region (see Example 6).

DETAILED DESCRIPTION OF THE INVENTION

Figure 1B:
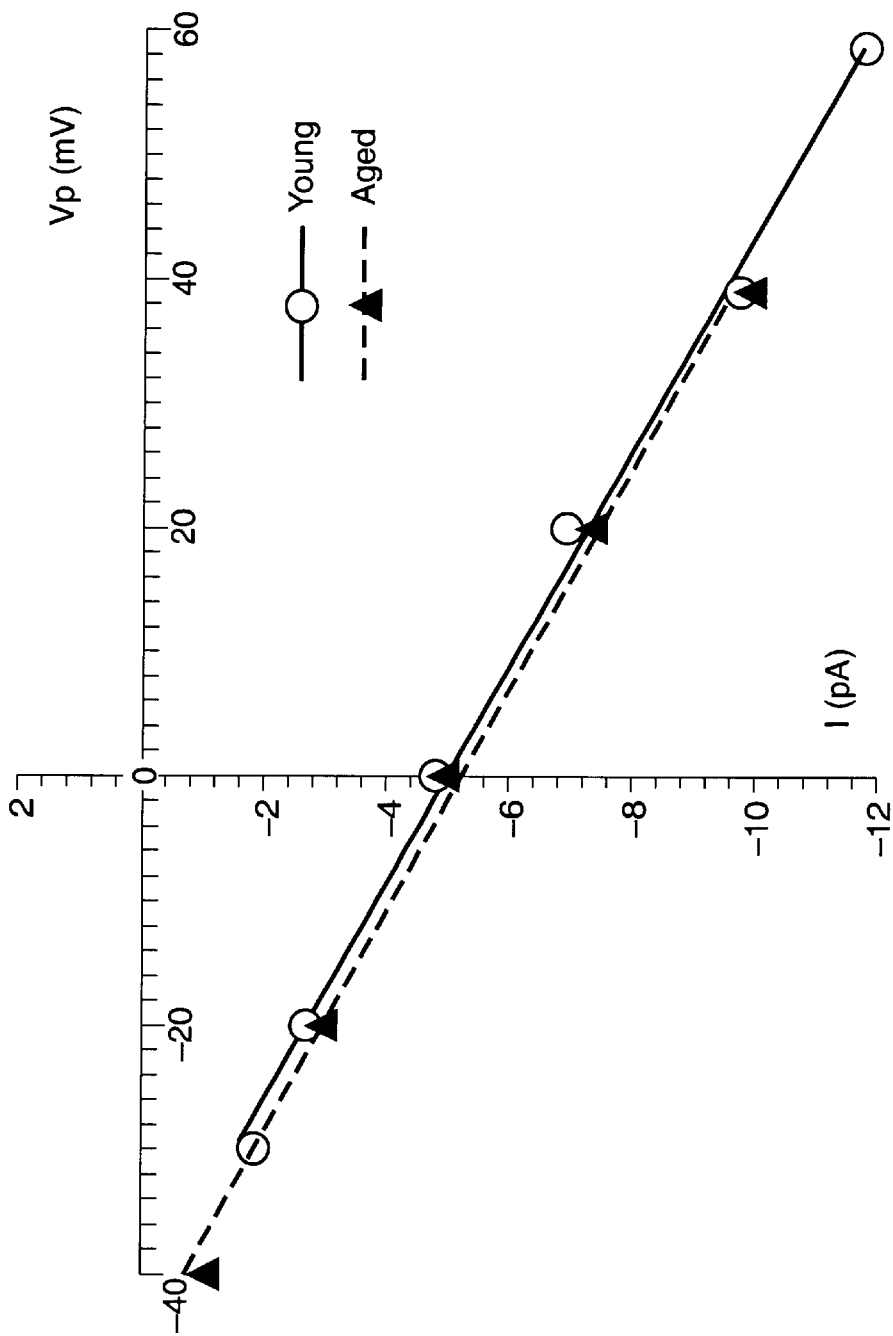

The invention concerns methods of diagnosing Alzheimer's disease (AD). These methods are based upon detecting the absence of a particular potassium ion channel in the cells of an AD patient; upon differences in intracellular calcium ion concentration in AD and non-AD cells in response to potassium channel blockers specific for the potassium ion channel that is absent in the cells of an AD patient; and differences between AD and non-AD cells in response to activators of intracellular calcium release such as activators of inositol-1,4,5-trisphosphate ($IP_3$). This invention also provides additional methods of diagnosing AD based upon detecting a significant reduction in the levels of a memory associated GTP-binding protein (Cp20) in the cells of an A.D. patient.

The first embodiment of the invention is based upon the discovery by the inventors that cells from people not suffering from AD have (at least) two types of functional potassium channels, with conductances of 113 pS (picosiemens) and 166 pS, as measured by the patch clamp technique (see Example 1). The 113 pS channel is either missing or not functioning in people with AD. The first embodiment of the invention involves diagnosing AD by determining whether cells of the patient have a functioning 113 pS potassium channel. The presence of a functioning 113 pS potassium channel indicates that the patient does not have AD. However, the absence of a functioning 113 pS potassium channel indicates that the patient does have AD.

In this embodiment of the invention, a suitable method of recording electrical conductances in the cells must be used to detect functional potassium channels in cells. Any technique which can measure electrical conductances in a cell can be used. Examples include intracellular microelectrode recording (indirect measurement), two microelectrode voltage clamp, and single microelectrode voltage clamp. The patch clamp technique, as described herein, is a preferred method for measuring electrical conductance in small structures. In an embodiment of the invention, the cell attached mode of the patch clamp technique is used to record the existence of potassium channels and the inside-out and outside-out patch configurations are used to record the sensitivity of potassium channels to various chemicals.

The second embodiment of the invention concerns another method for diagnosing AD. In this second embodiment, the cells are contacted with a potassium channel blocker that blocks the 113 pS channel but not the 166 pS channel. This blocker may substantially block the 113 pS channel but not substantially block the 166 pS channel. An example of such a blocker is TEA, or tetraethylammonium. The blocker has the effect in non-AD cells of transiently increasing intracellular $Ca^{2+}$ concentrations. In AD cells, the blocker has substantially no effect, allowing for variation within observational or technical error. In contrast, the intracellular calcium ion concentration increases several fold in non-AD cells after being exposed to 100 mM TEA (see FIG. 4B). The intracellular $Ca^{2+}$ concentration can be measured in various ways, such as by adding fluorescent indicators or absorbance indicators or by using a $Ca^{2+}$ electrode. Preferably, because of ease of operation, fluorescent indicators are used.

Figure 4B:
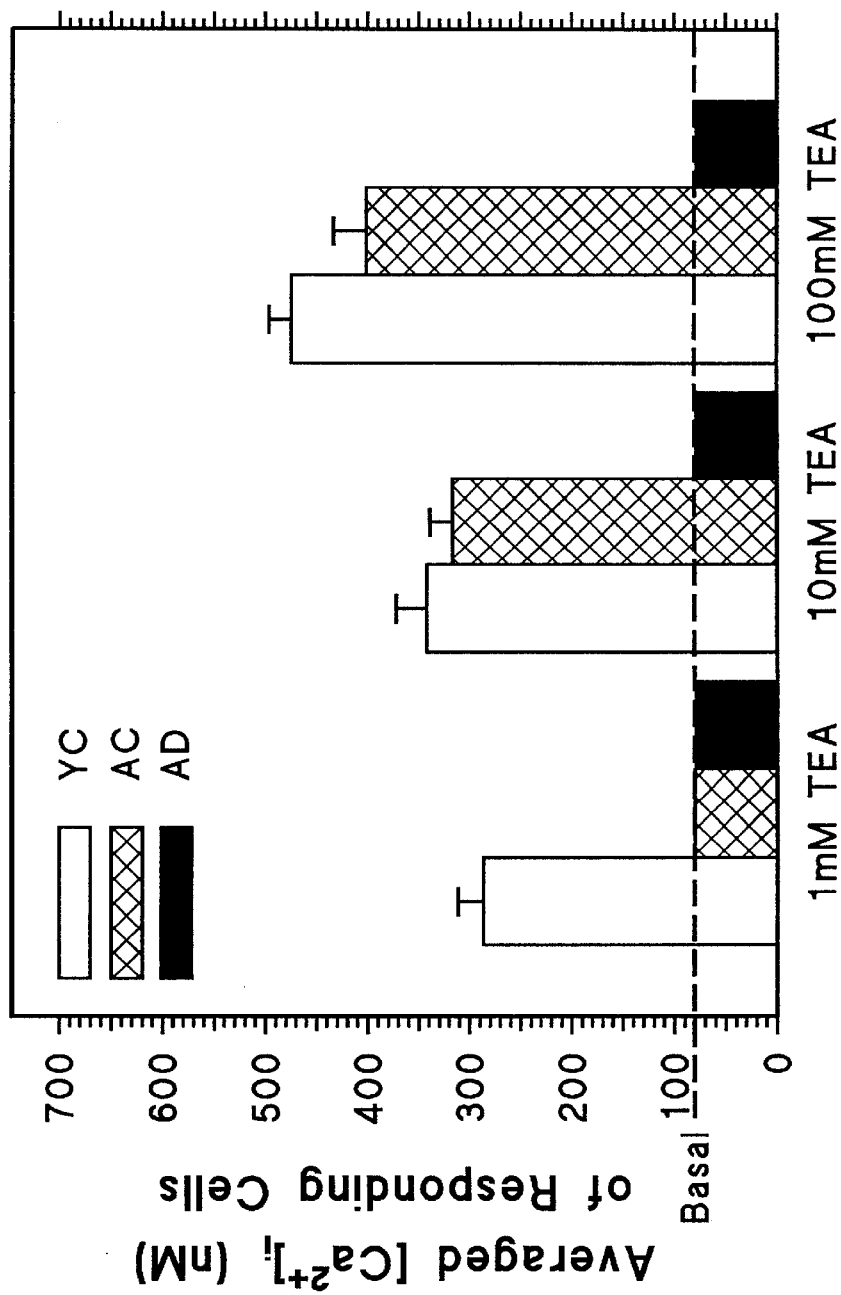
Figure 4C:
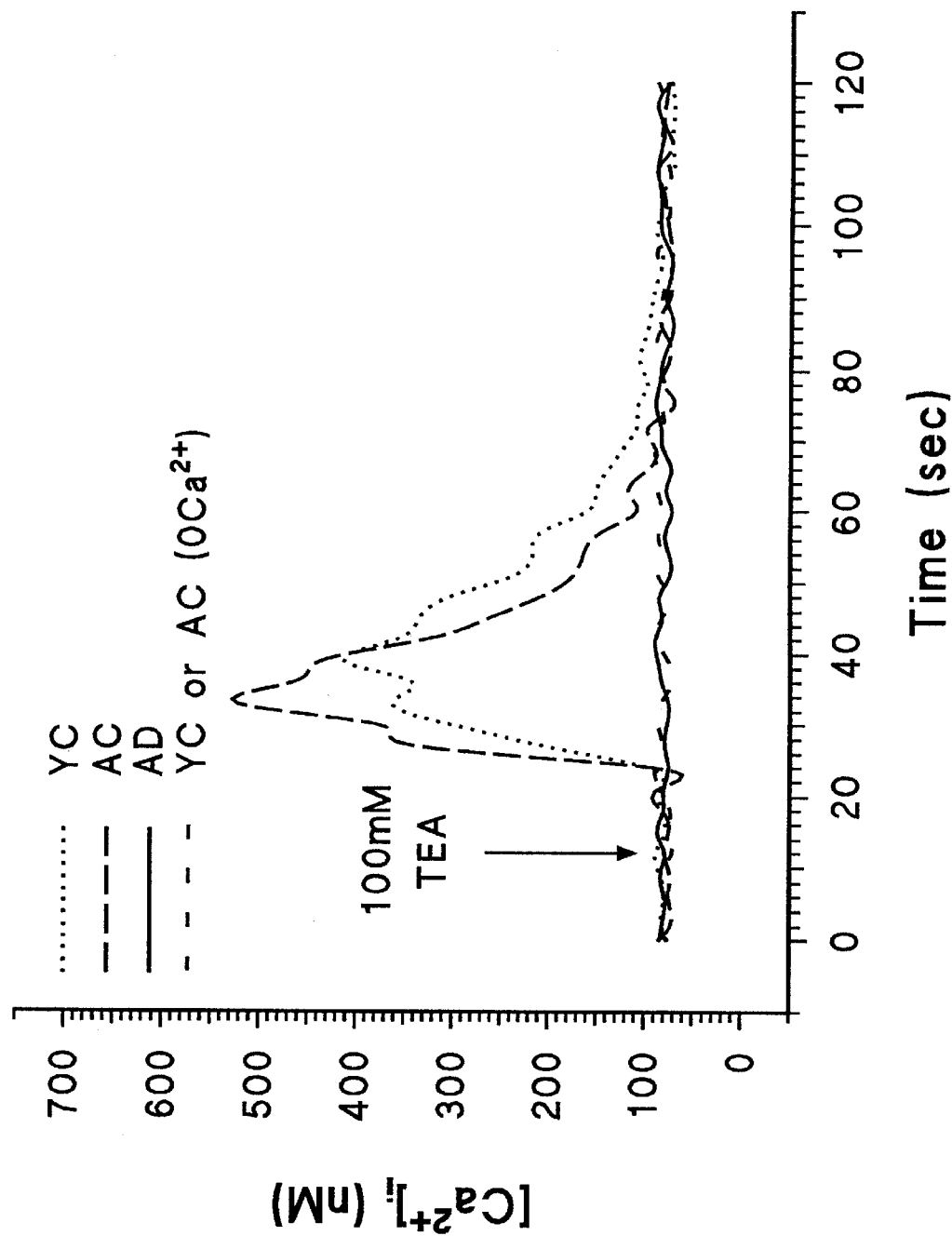

In this embodiment of the invention, the cells are first cultured with a $Ca^{2+}$ indicator, such as quin or fura-2, that fluoresces with an intensity proportional to the calcium concentration. The cells are then contacted with a select potassium channel blocker that has the ability to block the 113 pS channel but not the 166 pS channel. The fluorescence intensity of the cells before and after the addition of the potassium channel blocker is measured. In cells from people not suffering from AD the fluorescence intensity increases rapidly, peaks and then drops back down (FIG. 4C). This shows that the blocker has the effect of increasing, transiently, the calcium ion concentration. In cells from AD patients, the fluorescence intensity is substantially the same before and after the blocker is added. This is a reflection of the fact that the 113 pS channel is missing or non-functional in AD patients and thus potassium ion channel blockers that block the 113 pS channel, but not the 166 pS channel, do not have any effect on AD cells.

As mentioned above, the select potassium channel blocker used in this second embodiment of the invention is one that has the ability to block the 113 pS potassium channel but that has little or no effect on the 166 potassium channel. One example of such a blocker is TEA, with any biologically compatible counter anion. Preferably, the counterion is chloride. Other suitable potassium channel blockers can be easily found using the following method. Using the patch clamp technique described in Example 1, the 113 pS and 166 pS channels are detected in a viable human cell. The candidate potassium channel blocker is added to the culture containing the cells, and the patch clamp technique is used again. If the 166 pS channel is still functional, but the 113 pS channel is not, then the candidate blocker is suitable for use in this invention. Candidate potassium channel blockers include the known potassium channel blockers charybdotoxin, apamin, dendrotoxin, kalidotoxin, MCD-peptide, scyllatoxin, barium, cesium, leiurotoxin I and noxiustoxin. As shown in Example 2, TEA concentrations between 10 mM and 100 mM worked well. It is easy to extend this range of workable concentrations by using AD and non-AD control cells.

Example 2 exemplifies the second embodiment of the invention for diagnosing AD using a select potassium channel blocker, TEA, and measuring the effect on intracellular calcium ion. This method is so simple, with a yes or no answer, that the exemplified sophisticated apparatus is not required to make the diagnosis. Any method which will tell one if the intracellular calcium ion concentrations has increased or not as a result of contact with the select potassium ion channel blocker will suffice to give a diagnosis. In the preferred method, fluorescent calcium ion indicators are used. In this case, any method which will tell one if the fluorescence of the indicator has increased or not as a result of contact of the cells with the select potassum channel blockers will suffice. Any method used must be able to make the measurements in the short time available. The calcium ion influx peaks a short time after contact with the blocker, and then decreases to the baseline value. In Example 2, the time it takes to peak is less than one minute.

A simpler method for detecting a fluorescent calcium ion indicator would involve using a fluorimeter, a device with a light source for exciting the calcium ion indicator and a light meter for measuring the intensity of a the fluorescence. Fluorimeters are well known and commercially available. At the simplest level, the calcium ion indicator is added to the cells taken from the patient (either fresh or expanded in culture). After an hour or so of being in contact with the indicator (at about 2 micromolar concentration) the cells in suspension are placed in the fluorimeter and the fluorescence intensity from the indicator is measured. Then the select potassium channel blocker is added; if TEA is used, it is added to a concentration of about 100 mM. The fluorescence is measured again. If the intensity, within a time period between 20 seconds and 40 seconds, is substantially the same as before the TEA was added (taking account of changes in volume due to the addition of the TEA), then a positive diagnosis of AD is made. If the intensity increases within 30 seconds and subsides after another 30 seconds, then the patient does not have AD.

It is within the skill of the art to improve the simple scheme outlined above. For example, one could use a fluorimeter with dual sample holders, in which the difference in fluorescence from two samples is measured. Starting with identical samples of patient's cells (after incubation with the indicator) in each sample holder, the select potassium channel blocker is added to only one of the samples. If there is no change in the difference signal (that is, it remains as essentially zero), a diagnosis of AD is made. If the difference signal changes significantly, then the patient does not have AD. The advantage of the differences method is that it has a built in control which increases the accuracy of the measurement. It is still within the skill of the art to add the select potassium channel blocker automatically and to make more than one measurement at a time; i.e., to automate the method for a commercial medical laboratory. Before making any diagnoses using the methods taught here, the methods should be optimized for the particular apparatus and conditions in the laboratory by using non-AD and AD control cells, which are commercially available.

The third embodiment of the invention is yet another method of diagnosing AD. This method concerns the effect of agents that activate inositol-1,4,5,-trisphosphate ($IP_3$) or otherwise induce the release of calcium from intracellular storage sites. Such storage sites include the endoplasmic reticulum and other organelles that have receptors for $IP_3$. The preferred $IP_3$ activator is bombesin. Other agents that activate the release of calcium from intracellular stores which are useful in the invention include thrombin, bradykinin, prostaglandin $F_{2\alpha}$ and vasopressin. See, e.g., Berridge, M. J. and Irvine, R. F. (1984) *Nature* 312:135).

It has been discovered that cells from people not suffering from AD and cells from people suffering from AD both transiently release calcium ion in response to bombesin, but the resulting intracellular calcium concentration is much larger in AD cells than in non-AD cells. The determination is easily made using any method of measuring intracellular calcium ion concentration, as discussed above with respect to the second embodiment of the invention. Again, the use of fluorescent calcium indicators is the preferred method. The same experimental setup as described above for measuring fluorescence intensity can be used, i.e., a fluorimeter. In this method, it is also possible to standardize the fluorescence apparatus using non-AD and AD cells as controls. In this way, later measurements of just the patient's cells can provide a diagnosis. Alternatively, the patient's cells can be compared with non-AD cells as a control.

Example 3 exemplifies the third embodiment of the invention concerning the diagnosis of AD using activators of $IP_3$ and measuring their effect on calcium ion release into the cytosol from intracellular storage sites after contact with said activators. The amount of released calcium is larger in AD cells compared to non-AD cells. The increase in intracellular calcium concentration is transient: the concentration peaks soon after contact with the activator and is back to baseline value with 90 seconds. This effect is enhanced when the extracellular calcium ion concentration is zero or near zero (which is generally accomplished by washing the cells with BSS nominally free of calcium, however, other methods of tying up or negating the effect of the extracellular calcium ions can be used, such as adding EGTA, or adding a calcium channel blocker such as nifedipine, respectively). After contact with an $IP_3$ activator, such as bombesin, the intracellular calcium ion concentration in AD cells reaches a higher peak value and takes longer to return to the baseline value than either young or aged control cells (FIG. 5A). In the experimental setup described in Example 3, it was found that 42 seconds after the bombesin was added to the cells that the difference between the intracellular calcium ion concentrations in AD cells and in control cells was at a maximum, and that at that time period, i.e., at 42 seconds after bombesin was applied, the concentration of calcium ions was always greater than 300 nM in AD cells and was always less than 300 nM in control non-AD cells (FIG. 5B). Basal levels of both AD and non-AD fibroblasts were at 80 nM±0.5 nM. However, it should be noted that control values might differ from 80 nM, necessitating a criterion level of calcium signal greater or less than 300 nM. Furthermore, differences in measuring conditions might require a time longer or briefer than 42 seconds to show maximal differences between the calcium signals of AD and non-AD fibroblasts.

Again, it is not necessary to use the sophisticated methods and apparatus exemplified herein. This method of diagnosing AD can be performed more simply. One need not measure the absolute concentration of intracellular calcium; a measurement of its relative value will also work. In Example 3, the basal level of intracellular calcium ion concentrations in resting (i.e., nonactivated) cells was the same for both AD and control non-AD cells, 80 nM±0.5 nM. Thus, at the time where the concentration differences between AD and non-AD cells was maximum (i.e., at 42 seconds using bombesin and the inventors' apparatus, but the time would need to be worked out empirically for different activators and different setups) the intracellular calcium concentration in non-AD cells would be less than (300/80=) 3.75 times the basal level whereas the intracellular calcium concentration in AD cells would be greater than (300/80=) 3.75 times the basal level. Using commercially available AD and non-AD cells, one can easily determine the time at which the calcium concentrations are maximally different between AD and non-AD cells. This involves measuring relative intracellular calcium concentrations for resting cells, adding bombesin or another $IP_3$ activator, following the relative calcium ion concentrations for a minute or so, and finding the time (after the activator is added) at which the difference in relative calcium ion concentrations is at its maximum. Then, for any real sample from a patient, one simply needs to measure the relative basal intracellular calcium concentration by any means known in the art, add the activator to its prescribed concentration (about 1 micromolar for bombesin), wait the predetermined time and again measure the relative intracellular calcium concentration. If the ratio of the intracellular calcium concentration "after" the addition of the activator to the intracellular calcium concentration "before" the addition of the activator is greater than 3.75, the patient has AD; if it is less than 3.75, the patient does not have AD. It is not necessary to determine the time of maximal difference in calcium concentrations—any time where there is a reproducible difference between these ratios can be used. It is only necessary to work out the particular ratios for the time chosen from known AD and non-AD control cells.

The calcium ion indicators used in the second and third embodiments include any compounds which can enter the cell, are biocompatible, and which can bind to calcium ions to produce a species whose concentration is easily measured using any physico-chemical means and is proportional to the calcium ion concentration. Preferably the means is fluorescence or absorbance. Preferable fluorescent indicators are the commercially available indicators fura-2 AM, fura-2 pentapotassium salt, quin-2, and indo-1 from Molecular Probes (Eugene, Oreg.). The Chemical Abstracts name for fura-2, AM is 5-oxazolecarboxylic acid, 2-(6-(bis(2-((acetyloxy)methoxy)-2-oxoethyl)amino)-5-(2-(2-(bis(2-((acetyloxy)methoxy)-2-oxoethyl)amino)-5-methylphenoxy)ethoxy)-2-benzofuranyl)-, (acetyloxyl) methyl ester. The Chemical Abstracts name for fura-2, pentapotassium salt is 5-oxazolecarboxylic acid, 2-(6-(bis(carboxymethyl)amino)-5-(2-(2-(bis(carboxymethyl)amino)-5-methylphenoxy)ethoxy)-2-benzofuranyl)-. Other fluorescent calcium indicators include Fluo-3, Rhod-2, Calcium Green™, Calcium Orange™, Calcium Crimson™ Fura Red™ and Calcium Green Dextran™ (Molecular Probes (Eugene, Oreg.)). Generally, the cells are incubated with the indicators at a concentration of about 2 micromolar for about 60 minutes. An absorbance indicator which may be used is arsenazo. Finally, calcium levels could also be measured for this invention with calcium electrodes inserted into the cells.

In the exemplified embodiment of the invention, fluorescence was measured using an imaging system under the control of a personal computer. For excitation, 340 nm and 380 nm band pass path filters with a neutral-density filter were used. Images of fluorescence were obtained using a dichroic mirror, barrier filter and objective lens. The whole image can be recorded or portions thereof. A Hamamatsu Photonics Argus 50 Calcium Imaging system imaging 60 cells in a microscopic field at 10× magnification was used. Fluorescence from the cells was quantified in ¼ of the field at 10× magnification. Such an imaging system (and other similar currently available systems) with its microscope could be custom designed for everyday clinical laboratory analysis of cells' calcium signals. Other instrumentation and/or measurements would have to be adapted for the use of other calcium indicators.

In the methods of the invention, the cells that are taken from the patient can be any viable cells. Preferably they are fibroblasts; buccal mucosal cells; blood cells such as erythrocytes, lymphocytes, and lymphoblastoid cells; or nerve cells such as olfactory neurons. The cells may be fresh or may be cultured (as described in the examples). The fibroblast potassium channel dysfunction and resulting absence of TEA-induced calcium signals described herein suggest that AD, which primarily affects brain cells, is likely to alter potassium channel function in many different types of cells in the body. Similarly, AD is likely to alter calcium released by bombesin and related agents in many different types of cells in the body. The methods described herein to measure potassium channel function and calcium release, therefore, should be applicable for AD diagnosis using other cell types.

A punch skin biopsy could be used to obtain skin fibroblasts from a patient. These fibroblasts might be analyzed directly with the techniques described herein or be introduced into cell culture conditions. The resulting cultured fibroblasts would then be analyzed as described for the cultured fibroblasts obtained from the Coriell Cell Repositories described below. Other steps would be required to prepare other types of cells which might be used for analysis such as buccal mucosal cells, nerve cells such as olfactory cells, blood cells such as erythrocytes and lymphocytes, etc. For example, blood cells can be easily obtained by drawing blood from peripheral veins. Cells can then be separated by standard procedures (e.g., by using a cell sorter, centrifugation, etc.) and later analyzed in suspension or on a solid support (e.g., in petri dishes).

The fourth embodiment of this invention concerns yet another method for diagnosing Alzheimer's disease. This embodiment is based upon a discovery by the inventors that the memory associated GTP protein Cp20 is significantly reduced in the cells of Alzheimer's disease patients relative to the cells of healthy controls. Cp20, a high-affinity substrate for protein kinase C (PKC) (D.L. Alkon et al., *J. Neurochem.* 51, 903 (1988)), shows specific differences of phosphorylation in neurons of mollusks and mammals that undergo associative learning(J. T. Neary, T. Crow, D. L. Alkon, *Nature* 293, 658 (1981); T. J. Nelson, J. V. Sanchez-Andres; B. G. Schreurs, D. L. Alkon, *J. Neurochem.* 57, 2065 (1991); T. J. Nelson, C. Collin, D. L. Alkon, *Science* 247, 1479 (1990).). This GTP-binding protein, which induces a number of memory-specific neuronal changes [e.g. $K^+$ current reduction, increased synthesis of mRNA, and focusing of synaptic terminal branches-T. J. Nelson, C. Collin, D. L. Alkon, *Science* 247, 1479 (1990); T. J. Nelson and D. L. Alkon, USA 85, 7800 (1988); ibid 87, 269 (1990); D. L. Alkon et al. *Proc. Natl. Acad. Sci.* USA 87, 1611 (1990)], also regulates retrograde axonal transport(S. Moshiach, et al. *Brain Research* 605, 298 (1993)) and is a member of the adenosine diphosphate ribosylation factor (ARF) -protein family that has been implicated in the trafficking of particles between the Golgi and the endoplasmic reticulum (see Example 5). Here it is demonstrated that Cp20 is consistently and significantly reduced in the fibroblasts of both Alzheimer's patients and non-affected close relatives of Alzheimer's Disease patients, but not in aged-matched controls who are not members of families with hereditary Alzheimer's disease. Incubation of normal fibroblasts with low concentrations of soluble β-amyloid induced the Alzheimer's disease phenotypes for Cp20.

Any immunoassay method which will tell one if the Cp20 protein level has changed will suffice. In this method antibodies that recognize the Cp20 protein are contacted with a protein sample isolated from the cells of patients being diagnosed by this assay. The formation of a complex between the Cp20 protein and antibody is detected and the change in the level of Cp20 protein between the individual being tested relative to one or more control samples is assessed.

The Cp20 diagnostic assay for Alzheimer's disease will greatly improve the complicated clinical procedure used for Alzheimer's disease because of its strong positive correlation with a diagnosis of Alzheimer's Disease. It is preferred that this assay be used in conjunction with clinical diagnosis of Alzheimer's disease or other known methods of diagnosing Alzheimer's disease. By way of example, patients or individuals who may be diagnosed as having Alzheimer's disease by this assay include individuals who have received a clinician's tentative diagnoses of Alzheimer's disease, individuals with few clinical Alzheimer's disease symptoms, individuals who have been diagnosed as having atypical dementias, and in individuals who are members of families with Alzheimer's disease. A statistically significant reduction in the level of Cp20 protein relative to control samples (healthy age-matched individuals with no familial history of Alzheimer's disease) is reasonably predictive that the patient does have Alzheimer's disease. A normal level of Cp20 protein as determined by comparison to control protein samples isolated from age matched healthy individuals with no familial history of Alzheimer's disease, indicates that the patient does not have Alzheimer's disease. One of skill in the art will appreciate that the level of Cp20 protein in the cells of a patient to be diagnosed by this assay is assessed relative to control protein samples. Control protein samples should be isolated from an adequate population sample of healthy age matched controls with no history of Alzheimer's disease in their family. By way of example, a reduction of about 40% to 60% or higher, from the control levels of Cp20, as determined by an adequate control population sample size, is indicative of Alzheimer's disease. One of skill in the art will appreciate that the sample from the patient to be diagnosed is assessed against control protein samples from healthy aged matched controls and that a significant reduction in the Cp20 level in the patient's protein sample is determined based on comparison to the controls used in the given assay.

Immunoassays of the present invention may be radioimmunoassay, Western blot assay, immunofluorescent assay, enzyme immunoassay, immuno-precipitation, chemiluminescent assay, immunohistochemical assay, dot or slot blot assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Detection may be by colormetic or radioactive methods or any other conventional methods known to one skill in the art. Standard techniques known in the art for ELISA are described in *Methods in Immunodiagnosis,* 2nd Edition, Rose and Bigazzi, eds., John Wiley and Sons, New York 1980 and Campbell et al., *Methods of Immunology,* W. A. Benjamin, Inc., 1964, both of which are incorporated herein by reference. Such assays may be a direct, indirect, competitive, or noncompetitive immunoassay as described in the art (In "Principles and Practice of Immunoassay" (1991) Christopher P. Price and David J. Neoman (eds), Stockton Pres, New York, N.Y.; Oellirich, M. 1984. *J. Clin. Chem. Clin. Biochem.* 22: 895–904 Ausubel, et al. (eds.) 1987 in *Current Protocols in Molecular Biology*, John Wiley and Sons, New York, N.Y.

In this embodiment the cells taken from the patient being diagnosed may be any cell. Examples of cells that may be used include, but are not limited to, fibroblasts, buccal mucosal cells, blood cells, such as erythrocytes, lymphocytes and lymphoblastoid cells, and nerve cells and any other cell expressing the Cp20 protein. Necropsy samples and pathology samples may also be used. Tissues comprising these cells may also be used. The cells may be fresh, cultured or frozen. Protein samples isolated from the cells or tissues may be used immediately in the diagnostic assay or frozen for later use. In a preferred embodiment fibroblast cells are used. Fibroblast may be obtained by a skin punch biopsy as described above.

Proteins may be isolated from the cells by conventional methods known to one of skill in the art. In a preferred method, cells isolated from a patient are washed and pelleted in phosphate buffered saline (PBS). Pellets are then washed with "homogenization buffer" comprising 50 mM NaF, 1 mM EDTA, 1 mM EGTA, 20 µg/ml leupeptin, 50 µg/ml pepstatin, 10 mM TRIS-HCl, pH=7.4, (see Example 6) and pelleted by centrifugation. The supernatant is discarded, and "homogenization buffer" is added to the pellet followed by sonication of the pellet. The protein extract may be used fresh or stored at −80° C. for later analysis.

In this method the antibodies used in the immunoassay may be monoclonal or polyclonal in origin. The Cp20 protein or portions thereof used to generate the antibodies may be from natural or recombinant sources or generated by chemical synthesis. Natural Cp20 proteins can be isolated from biological samples by conventional methods. Examples of biological samples that may be used to isolate the Cp20 protein include, but are not limited to, tissues such as squid optic lobe, Hermissenda nervous system, skin cells, such as, fibroblasts, fibroblast cell lines, such as Alzheimer's disease fibroblast cell lines and control fibroblast cell lines which are commercially available through Coriell Cell Repositories, (Camden, N.J.) and listed in the National Institute of Aging 1991 Catalog of Cell Lines, National Institute of General Medical Sciences 1992/1993 Catalog of Cell Lines [(NIH Publication 92–2011 (1992)].

By way of example, the Cp20 may be isolated from squid optic lobe by first homogenizing the tissue using standard methodologies. A preferred homogenization buffer is 10 mM Tris-HCl, pH 7.4, 20 ug/ml leupeptin, 20 ug/ml pepstatin, 50 mM NaF, 1 mM EDTA, 1 mM EGTA, 0.1 mM PMSF (phenylmethylsulfonyl-fluride) supplemented with 200 mM DTT. (See Example 5). Isolation and purification of the protein from the homogenate can be performed by conventional chromatography techniques such as high performance liquid chromatography (HPLC) (see Example 5). Preferably, both anion and cation exchange HPLC columns are used in the purification. Additional purification steps, such as, size exclusion chromotography, ammonium sulfate precipitation, or dye affinity chromotography or any other conventional methods may also be used. Alternatively, the Cp20 protein may be purified by immunoaffinity chromatography using antibodies which recognize the Cp20 protein. Recombinant Cp20 proteins or peptides may also be used in generating Cp20 antibodies and are produced and purified by conventional methods.

Synthetic Cp20 peptides may be custom ordered or commercially made or synthesized by methods known to one skilled in the art (Merrifield, R. B. (1963) *J. Amer. Soc.* 85:2149) based on the partial amino acid sequence of the Cp20 protein provided herein (see FIG. 12A). Alternatively, the isolated Cp20 protein may be subjected to enzymatic digestion and the resulting peptides used to generate antibodies. By way of example, trypsin may be used to digest the Cp20 protein and generate peptides. One of skill in the art will appreciate that the specific trypsin digestion conditions will be dependent on the quantity of Cp20 present, and the preparation method of the Cp20 (i.e., whether it is bound to nylon membrane, nitrocellulose, or in solution, and if so what other substances are present). One skilled in the art will also know how to perform a tryptic digest of the protein and purify the fragments by HPLC or other means prior to sequence determination. An exemplary tryptic digest fragment for Cp20 is shown in FIG. 12A. If the peptide is too short to be antigenic it may be conjugated to a carrier molecule to enhance the antigenicity of the peptide.

Examples of carrier molecules known to workers on the field include, but is not limited to human albumin, bovine albumin and keyhole limpet hemo-cyanin ("Basic and Clinical Immunology" (1991) Stites, D. P. and Terr A. I. (eds) Appleton and Lange, Norwalk Conn., San Mateo, Calif.).

Exemplary antibody molecules for use in the methods of the present invention are intact immunoglobulin molecules, substantially intact immunoglobulin molecules or those portions of an immunoglobulin molecules that contain the antigen binding site, including those portions of an immunoglobulin molecules known in the art as F(ab), F(ab'); F(ab')$_2$ and F(v). Polyclonal or monoclonal antibodies may be produced by methods known in the art. (Kohler and Milstein (1975) Nature 256, 495–497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in E. Coli is the subject of the PCT patent applications: publication number WO 901443, WO 901443 and WO 9014424 and in Huse et al. (1989) Science 246:1275–1281. Alternatively, the Cp20 protein or peptides or portions thereof may be forwarded to a company for generation of antibodies.

The antibodies of this invention may react with native or denatured Cp20 protein or peptides. The specific immunoassay in which the antibodies are to be used will dictate which antibodies are desirable.

By way of example, the isolated Cp20 or portions thereof may be injected into the spleen cells of mice for generating monoclonal antibodies. The spleens are fused to hybridoma cells, the desired clones selected and the monoclonal antibodies generated and purified by methods known to one skilled in the art. (Ausubel et al. (eds) 1987". Current Protocols in Molecular Biology" John Wiley and Sons, New York, N.Y.).

Polyclonal antibodies may also be generated using the Cp20 protein or portions or peptides thereof by standard methods. By way of example, peptides derived from the Cp20 partial amino acid sequence shown in FIG. 12A (single letter code) may be used. For example, the peptide ARLW-TEYFVIIDDDC (SEQ. ID. NO. 9), derived from the partial amino acid sequence (FIG. 12A) may be synthesized by standard methods. Using conventional methods, rabbits may be immunized with this Cp20 peptide preferably conjugated with hemo-limpet hemocyanin. One skilled in the art will appreciate that if a synthetic peptide is used, a cysteine group is added to the C-terminal to facilitate conjugation. Preferably about 0.2 to 1.0 milligrams (mg) of the peptide-antigen in Freund's complete adjuvant is used for the initial injection. The animal receives similar booster doses in incomplete adjuvant thereafter and antisera titer is assessed by ELISA assay. Satisfactory levels of antisera are obtained when the antipeptide antibody titer reaches a plateau. This antibody can be used in the diagnostic immunoassay described above. Alternatively, shorter peptide sequences derived from the Cp20 amino acid sequence presented in FIG. 12A, or the entire Cp20 amino acid sequence shown in FIG. 12A, may also be used to immunize animals for the generation of both monoclonal and polyclonal antibodies.

In a preferred embodiment antibodies that recognize the Cp20 protein are used to detect the protein in Western Blot Analysis comparing protein samples isolated from the cells of the patient to be diagnosed by the assay and protein samples from healthy age-matched control individuals with no history of Alzheimer's disease in their family. The levels of Cp20 protein in the patient samples versus the control samples can be assessed visually or by using standard densitometric scanning techniques. Commercially available computer programs are available for densitometric analysis. Control cell lines are also commercially available through Coriell Cell Repositories (Camden, N.J.).

The predicted Cp20 is about a 20 kilodalton protein with structural and biochemical features that identify it as a member of the ARF family of proteins. The Cp20 protein also exists in the form of a dimer of about 40 kD and depending on the conditions used in an assay can appear as a monomer or dimer. A partial amino acid sequence for Cp20 is shown in FIG. 12A. This invention therefore also relates to a Cp20 protein comprising the amino acid sequence shown in FIG. 12A and more specifically relates to the Cp20 peptide sequence shown in FIG. 12A. This invention is also intended to encompass protein or peptides substantially homologous to the Cp20 protein and having substantially the same function as the Cp20 protein of this invention.

This invention also relates to expression vectors for producing recombinant Cp20 protein comprising a nucleic acid sequence for Cp20 and a vector for expressing all or part of the Cp20 protein. Standard methodology can be used to derive nucleic acid sequences based on the partial amino acid sequence shown in FIG. 12A for incorporation into such expression vectors. One skilled in the art will know how to utilize currently extant cDNA library screening techniques or various techniques involving PCR (polymerase chain reaction) for obtaining the corresponding DNA sequence from the partial amino acid sequence shown in FIG. 12A, and for incorporating the DNA sequence into a suitable expression vector. Further, one of skill in the art will know the correct combination of operational elements to incorporate into such vectors and that such vectors are easily constructed using conventional methods (Ausubel et al. (1987), in "Current Protocols in Molecular Biology" John Wiley and Sons, New York). The Cp20 amino and sequence provided herein can also be used to obtain homologs of Cp20 from other species by methods known to one skilled in the art.

This invention also relates to kits which can be utilized in performing the diagnostic assay. Such a kit would comprise antibodies which recognize the Cp20 protein. Such antibodies may be polyclonal or monoclonal. The kit may also contain instructions relating to the use of these antibodies in diagnostic assays. The kit may also contain other reagents for carrying out the assay such as buffers, secondary antibodies and the like.

In yet another embodiment of this invention a diagnostic index for diagnosing Alzheimer's is provided which integrates two or more tests for diagnosing Alzheimer's diseases thereby providing a scoring system to be used in distinguishing AD cells from non-AD cells. Examples of the diagnostic tests that may be integrated to generate the diagnostic index include, but are not limited to, the diagnostic methods described herein, including detecting the absence of the 113 ps potassium ion channel in the cells of an Alzheimer disease patient, detecting differences in intracellular calcium ion concentration in AD and non-AD cells in response to potassium channel blocker specific for the potasium ion channel that is absent in AD cells, differences between AD and non-AD cells in response to activators of intracellular calcium release and reduction in the levels of a memory associated GTP-binding protein(cp20) in the cells of an AD patient. Preferably at least two diagnostic tests an used in generating the index, most preferably three diagnostic tests are used in generating the index. The two or more diagnostic tests used in generating the index can assess the same alteration in AD versus non AD cells or different alterations in AD versus non-AD cells. By way of example the diagnostic tests used to generate the scoring system for the index may comprise three diagnostic tests: one test may assess the differences in intracellular calcium ion concentration in AD versus non AD cells in response to a potassium ion channel blocker, and two tests may assess the differences in intracellular calcium release in AD versus non AD cells in response to two different activators of intracellular calcium release. By way of example TEA can be the potassium ion channel blocker and the activators of intracellular calcium release may be bombesin or bradykinin.

One of skill in the art recognizes that for an individual test statistical analysis could be performed on a reference or normative population sample of cells to determine confidence levels of having Alzheimer's disease based on the results of that test. Accordingly for each test, a scale can be arbitrarily partitioned into regions having scores such that a correct combination of the scores provides a diagnositc index having a certain degree of confidence. The partioning can be performed by conventional classification methodology including, but not limited to, histrogram analysis of the cells or cell lines used in performing the test multivariable regression or other typical analysis or other classification techniques. For example, one skilled in the art recognizes that multi-variable regression analysis may be performed to perform this partitioning or analyze empirical/arbitrary partitioning in order to determine whether the composite clinical index has a higher degree of significance than each of the individual indices from respective tests.

It is preferable that each test be performed to maximize the differences between AD verus non-AD cells being assessed. By way of example parameters that can be manipulated to maximize differences between AD versus non-AD cells include, but are not limited to, concentration of the drug or reagent being used in the test, latency of the response, amount of the Cp20 protein or the phosphorlylation state of the protein.

By way of example a diagnostic index can be generated by integrating the scored results, values or signals from a test assessing release of intracellular calcium levels in AD versus non AD in response to bradykinin, a test assessing release of intracellular calcium in AD versus non-AD cells in response to bombesin, and a test assessing potassium channel function in AD versus non-AD cells after exposure to TEA (See Examples 2, 3 and 7). By way of example, the partitioning or classification of the response may be based on the percentage or cells responding in the given test and/or the magnitude of the integrated area of the response. By way of example, in a diagnostic test utilizing bombesin, if the time-integrated calcium ($Ca^{2+}$) concentration is <23000 nanomolar (nM)-seconds (sec) then zero is assigned as the score. For each test a reference or normative sample population was evaluated, partioned to maximize confidence levels and scored. A sample clinical index is provided below:

| Treatment | Response | Score |
|---|---|---|
| Bradykinin (0.1 nm) | <1.5% responding cells | 0 (no response) |

| Treatment | Response | Score |
|---|---|---|
| (Latency of the onset ≦ 135 sec) TEA (100 mM) | ≧1.5% responding cells | −0.5 |
| | ≧4.0% responding cells | −1.0 |
| | <5% responding cells | 0 (no response) |
| (Latency of the onset ≦ 60 sec) Bombesin* (1 μm) | ≧5% responding cells | 0.5 |
| | ≧16% responding cells | 1.0 |
| | <50% responding cells or area <23000 nM-sec | 0 (no response) |
| (Latency of the onset ≦ 40 sec) | ≧50% responding cells and area ≧23000 nM-sec | −0.5 |
| | ≧50% responding cells and area ≧30000 nM-sec | −1.0 |

*Calcium free media

If the above sample diagnostic index is used, it is preferable that a 0.1 nM concentration of bradykinin be used in the given diagnostic test, and that the response be measured within a period of 135 seconds or less. For TEA it is preferable that a 100 mM concentration be used in a given test and that the response be measured within a period of 60 seconds or less. For bombesin it is preferable that a 1 μM concentration be used in a given test and that the response be measured in a period of 40 seconds or less. For bombesin the integrated area is in units of nanomolar (nM) calcium concentration-seconds (sec.).

A net positive score is indicative of non-AD, whereas a net negative score is indicative of AD. One of skill in the art will appreciate that the scoring numbers may be scaled or biased.

This invention also includes a sample scoring system for Alzheimer's disease and a means for providing a signal corresponding to the first diagnostic test, the second diagnostic test and any additional tests. This invention further provides a means for combining the respective signals into a composite score. These means may be implemented in accordance with known signal or data acquisition apparatus and techniques indicating software operating on a conventional computer.

All books, articles, or patents referenced herein are incorporated by reference. The present invention will now be described by way of examples, which are meant to illustrate, but not limit, the scope of the invention.

EXAMPLE 1
Patch-clamp Diagnostic Test

Cultured skin fibroblasts (described in Table 3) from the Coriell Cell Repositories (Camden, N.J.) were grown under highly standardized conditions. Cristafallo, V. J. and Chapentier, R. J. (1980) *Tissue Culture Methods* 6:117. The following cell lines were used for the experiments: Young Control Fibroblasts ("YC") 3652, 3651, 2987, 4390, 3377, 8399 (21.5±2.8 years, Mean±S.D); Age-matched Control Fibroblasts ("AC") 3524, 6010, 6842, 7603, 9878 (65.2±6.0 years); and Alzheimer's Disease Fibroblasts ("AD") 6848, 7637, 5809, 8170, 6840, 8243, 6263 (60.6±6.8 years). Five AD lines were from familial patients. Some of the lines (2 AC and 4 AD) were from Canadian kindred.

In agreement with the literature, the data indicate the time to phase out does not vary between the AD and control lines (YC and AC). Cells were seeded (approximately 5 cells per $mm^2$) in 35 mm Nunc petri dishes in Dulbecco's Modified Eagle Medium (DMEM, Gibco), supplemented with 10% fetal calf serum and used when cell density was equivalent for all cell lines, between days 2 and 4 after plating. On average, fibroblasts from AD patients and controls took the same time to reach erosion density (50 cells/$mm^2$).

Patch-clamp experiments were performed at room temperature (21–23° C.), following standard procedures set forth in Sakmann, B. and Neher, E. (1983) *Single Channels Recordings* (Plenum N.Y.) and Kukuljan, M., et al. (1991) *J. Membrane Biol.* 119:187. Before recordings, culture medium was replaced with the following solution: 150 mM NaCl, 5 mM KCl, 2 mM CaCl$_2$, 1 mM MgCl$_2$, 10 mM HEPES (NaCl) pH=7.4. Pipettes were made from Blue Tip capillary tubes (I.D. 1.1–1.2 mm) using a BB-CH Mecanex puller, and then filled with a high potassium solution of 140 mM KCl, 2 mM CaCl$_2$, 1 mM MgCl$_2$, 10 mM HEPES (NaOH), pH=7.4. Pipette resistances were approximately 6 MΩ. Records were obtained using an Axopatch-1C amplifier (dc-10 kHz), stored on tape (Toshiba PCM-video recorder), and later transferred to a personal computer using an Axolab interface. Only recordings lasting for at least 3 minutes were considered for final analysis. The pClamp suite of programs was used for single-channel data acquisition and analysis. Amplifier, interface and software were obtained from Axon Instruments (Foster City, Calif.).

In the cell-attached mode, two types of potassium channels were recorded from human skin fibroblasts. Since pipettes were filled with a high potassium solution, potassium currents were inward as expected, and their reversal potential approximately corresponded to the cell resting potential. A potassium channel (113 pS) of approximately 4.5 pA unitary current size (0 mV pipette potential), with identical kinetics appeared in YC and AC fibroblasts, but was entirely absent in the recording of AD fibroblasts (FIG. 1A). Downward deflections represent the open state. I/V relationships of the same channels in FIG. 1A (FIG. 1B) and slope conductances (determined by linear regression) were almost identical within the voltage range explored, 113.2±0.9 pS (Mean±S.D., n=8)) for YC and 112.9±3.2 pS (n=7) for AC fibroblasts.

Figure 2A:
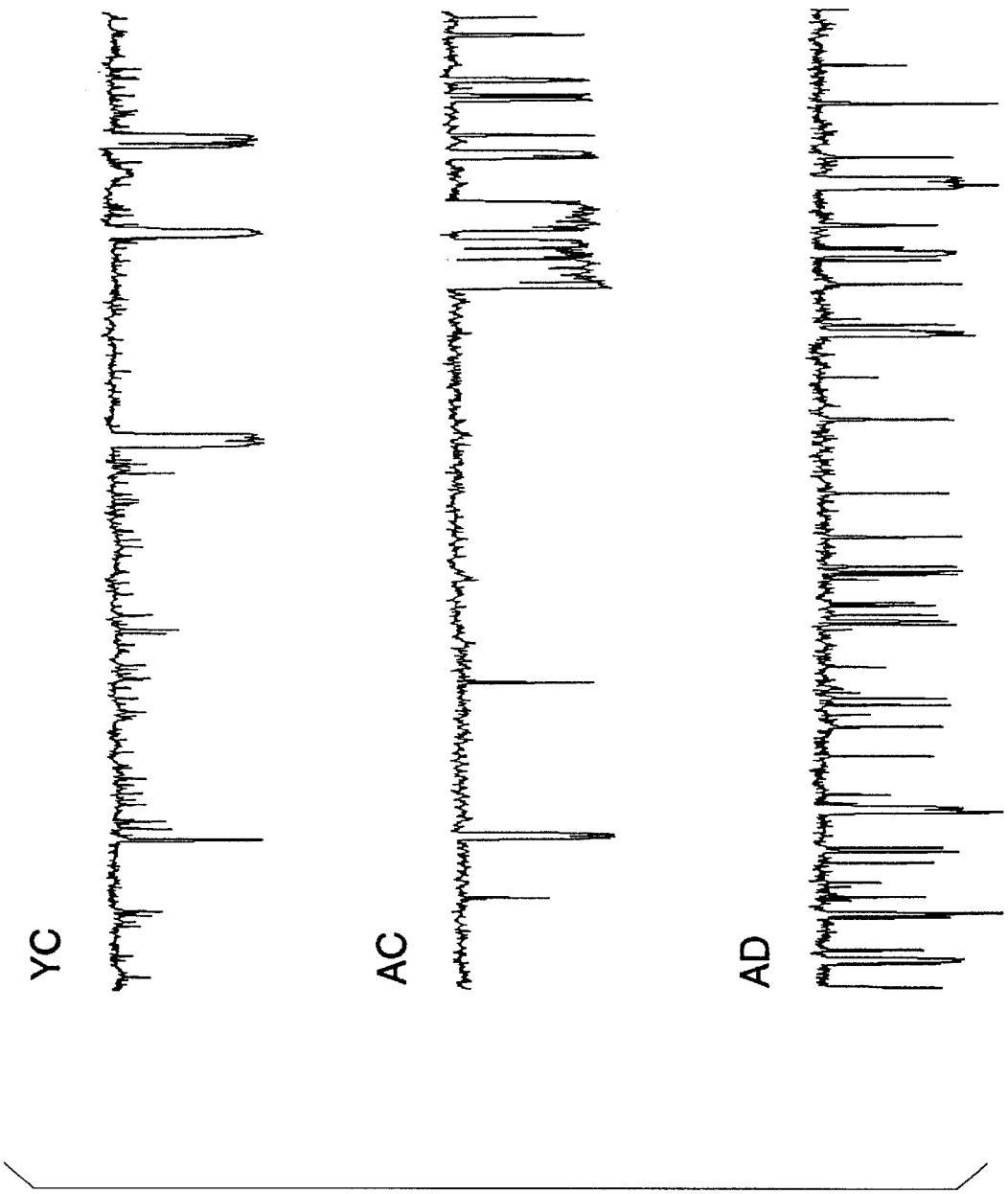
FIGS. 2A–2B. 166 pS channel. (2A). Cell attached recordings from Alzheimer and control fibroblasts. A second channel (166 pS) was recorded under the same conditions from fibroblasts of all three groups (AD, YC and AC). (2B). I/V relations and slope conductances. I/V relations as well as slope conductances [YC=174±5.7 pS, n=4; AC=169.2±2.8 pS, n=4; AD=157.6±4.7 pS, n=6 (Mean±S.D.)] were approximately the same across groups. Membrane potential was similar in control (−42.6±5.4, Mean±S.D., n=7) and in AD (−45.4±6.9, n=3) fibroblasts.
Figure 2B:
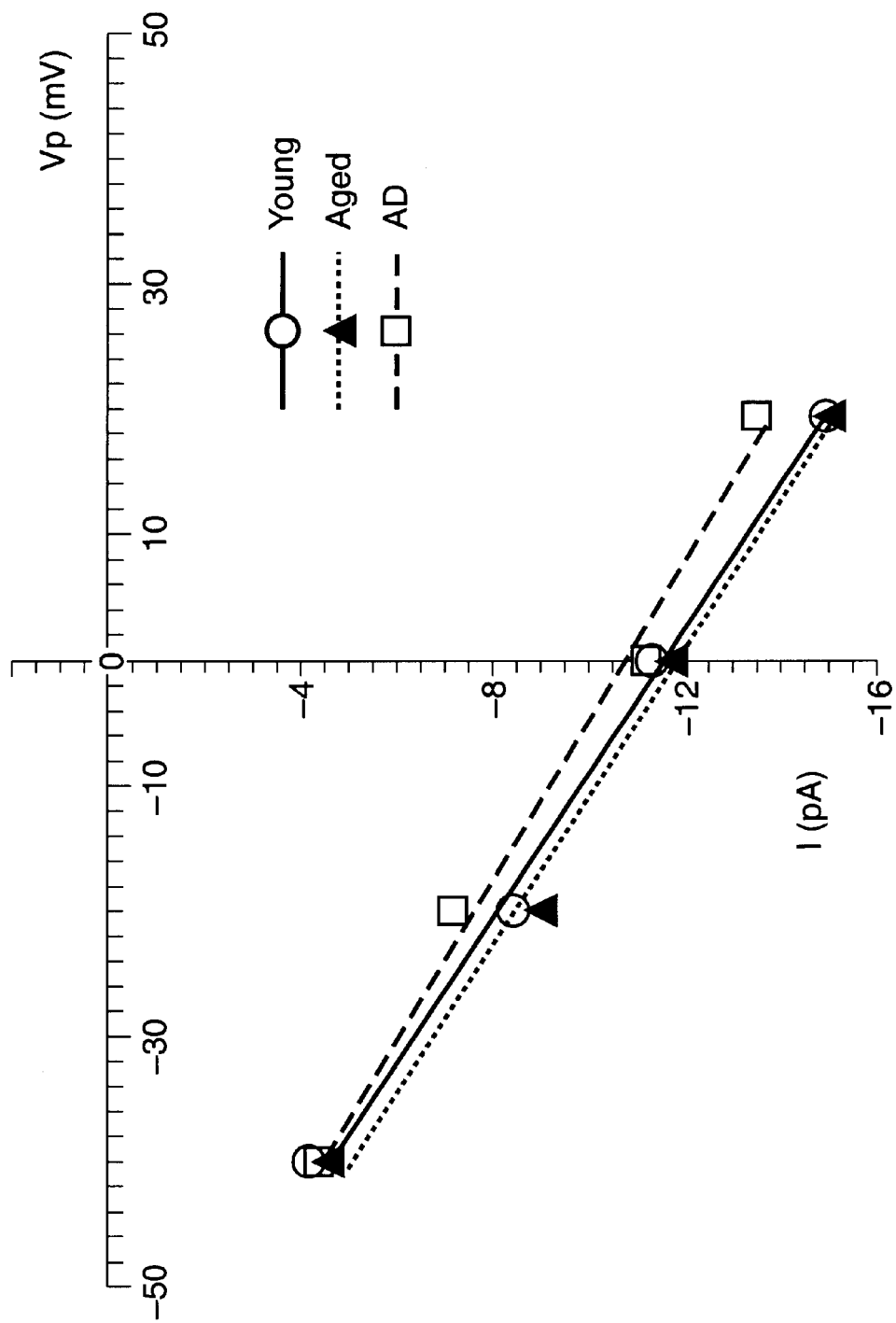

A second channel (166 pS) was recorded under the same conditions from fibroblasts of all three groups (FIG. 2A). I/V relations (FIG. 2B) as well as conductance (YC=173.4±5.7 pS, n=4; AC=169.2±2.8 pS, n=4; AD=157.6±4.7 pS, n=6 (Mean±S.D.)) were approximately the same across groups. Membrane potential was similar in control (−42.6±5.4, Mean±S.D., n=7) and in AD (−45.4±6.9, n=3) fibroblasts.

Both channels had linear voltage-current relationships, with slope conductances of 113 pS and 166 pS respectively (FIGS. 1A–1B and 2A–2B). At 0 mV pipette potential, the channels could easily be identified by their unitary current size (FIGS. 1A and 2A) and by their percentages of open time, approximately 60% for the 113 pS K$^+$ channel and approximately 10% for the 166 pS K$^+$ channel. For both channels, the percentages of open time showed no significant voltage-dependence (+60 to −40 mV pipette potential). The 113 pS K$^+$ channel was found in 47% of YC cells (n=30) and 94% of the AC cells (n=17), while it was never found in AD fibroblasts (n=24) ($\chi^2$ =18.96, p<0.001 (Table 1)). There were no AD cell lines (N=6) that had fibroblasts with an observable 113 pS channel. By contrast, all AC cell lines (N=5) and three of six YC cell lines had fibroblasts with observable 113 pS channels ($\chi^2$=11.93, p<0.005 (Table 2)). The 166 pS channel found was similar frequency in all three groups ($\chi^2$=0.89, N.S. (Tables 1 and 2)).

The 113 pS channel found to be "absent" in the AD fibroblasts, could be present but not functional. Such dysfunction could involve structural changes in the channel and/or alteration in processes involved in channel activity regulation.

Using cell-free patches, following the method described above, it was observed that both channels were sensitive to 50 mM Ba$^{2+}$ (inside-out, n=4 for each channel), but only the 113 pS channel was sensitive (outside-out, n=4 YC, n=3 AC) to the K$^+$ channel blocker tetraethylammonium (TEA). The TEA-blockade of the 113 pS channels (possibly together with other channels) significantly affects membrane potential since control cells (n=4) depolarized 13–20 mV after 100 mM TEA addition.

TABLE 1

Number of Cells

| Condition | Total | 113 pS K$^+$ Channel | 166 pS K$^+$ Channel |
|---|---|---|---|
| Young Controls | 30 | 14(47%) | 6(20%) |
| Aged Controls | 17 | 16(94%) | 6(35%) |
| Alzheimer Patients | 24 | 0(0%) | 8(33%) |

TABLE 2

Number of Cell Lines

| Condition | Total | 113 pS K$^+$ Channel | 166 pS K$^+$ Channel |
|---|---|---|---|
| Young Controls | 6 | 3 | 4 |
| Aged Controls | 5 | 5 | 3 |
| Alzheimer Patients | 7 | 0 | 4 |

When using control cells, it is best to use age-matched control cells.

EXAMPLE 2

TEA-Ca$^{2+}$ Diagnostic Test

Cultured skin fibroblasts (described in Table 3) from the Coriell Cell Repositories (Camden, N.J.) were grown as described in Example 1.

Thirteen AD, ten AC, and six YC were used for the calcium-imaging experiments. Culture medium was replaced and washed three times with basal salt solution ("BSS") consisting of 140 mM NaCl, 5 mM KCl, 2.5 mM CaCl$_2$, 1.5 mM MgCl$_2$, 5 mM glucose, 10 mM HEPES (NaOH), pH 7.4. Nominally Ca$^{2+}$ free BSS was prepared as BSS without adding CaCl$_2$.

Fura-2 (acetyloxymethyl ester) (Fura-2AM) was purchased from Molecular Probes (Eugene, Oreg.) and stored as a 1 mM solution in dimethylsulfoxide. Fura-2AM was added to a final concentration of 2 $\mu$M and cells were incubated at room temperature (21°–23° C.) for 60 minutes. After incubation, cells were washed at least three times with BSS at room temperature before [Ca$^{2+}$]$_i$ determinations. Fluorescence was measured with a Hamamatsu ARGUS 50 imaging system (Hamamatsu Photonics, Japan) under the control of a personal computer (Hamamatsu imaging software package). Excitation at 340 nm and 380 nm was attenuated with neutral density filters. Fluorescent images were obtained with a 400 nm dichroic mirror and a 510 nm long-pass barrier filter. The objective lens was an X10 Nikon UV fluor. Fluorescence was measured within a uniformly illuminated fraction (¼) of the whole image.

The averaged Ca$^{2+}$ responses within 15×15 pixels in cytosolic and in nuclear cellular compartments obtained were quantified with ratios between emitted 510 nm fluorescence activated at 340 nm and fluorescence emitted at 510 nm with activation at 380 nm. These ratios were transformed to absolute values of [Ca$^{2+}$]$_i$ after calibration based on the following equation:

$$R = R_{max} + (R_{min} - R_{max})/(1 + ([Ca^{2+}]_i/Kd)^b).$$

Here R denotes fluorescence intensity illuminated by 340 nm divided by fluorescence intensity illuminated by 380 nm (F340/F380), and $R_{max}$ and $R_{min}$ are the values of R when the concentration of calcium is at a maximum and a minimum (i.e., the maximum and minimum value measurable by the machine under the measuring conditions), respectively. Kd is a dissociation constant of fura-2 for $Ca^{2+}$ and was determined as 240 nM. The value of b, which determined the degree of asymmetry, was 1.2. TEA application caused a minimum of 100% $[Ca^{+2}]_i$ elevation in at least 18% of cells in every control cell line except one young control. A response of 100% $[Ca^{+2}]_i$ elevation in at least 10% of cells in a line was, therefore, considered to be a conservative criterion for a positive response. Only one AD cell line had cells with any response (100% $[Ca^{+2}]_i$ elevation in 4% of cells), well below the criterion).

Figure 3B:
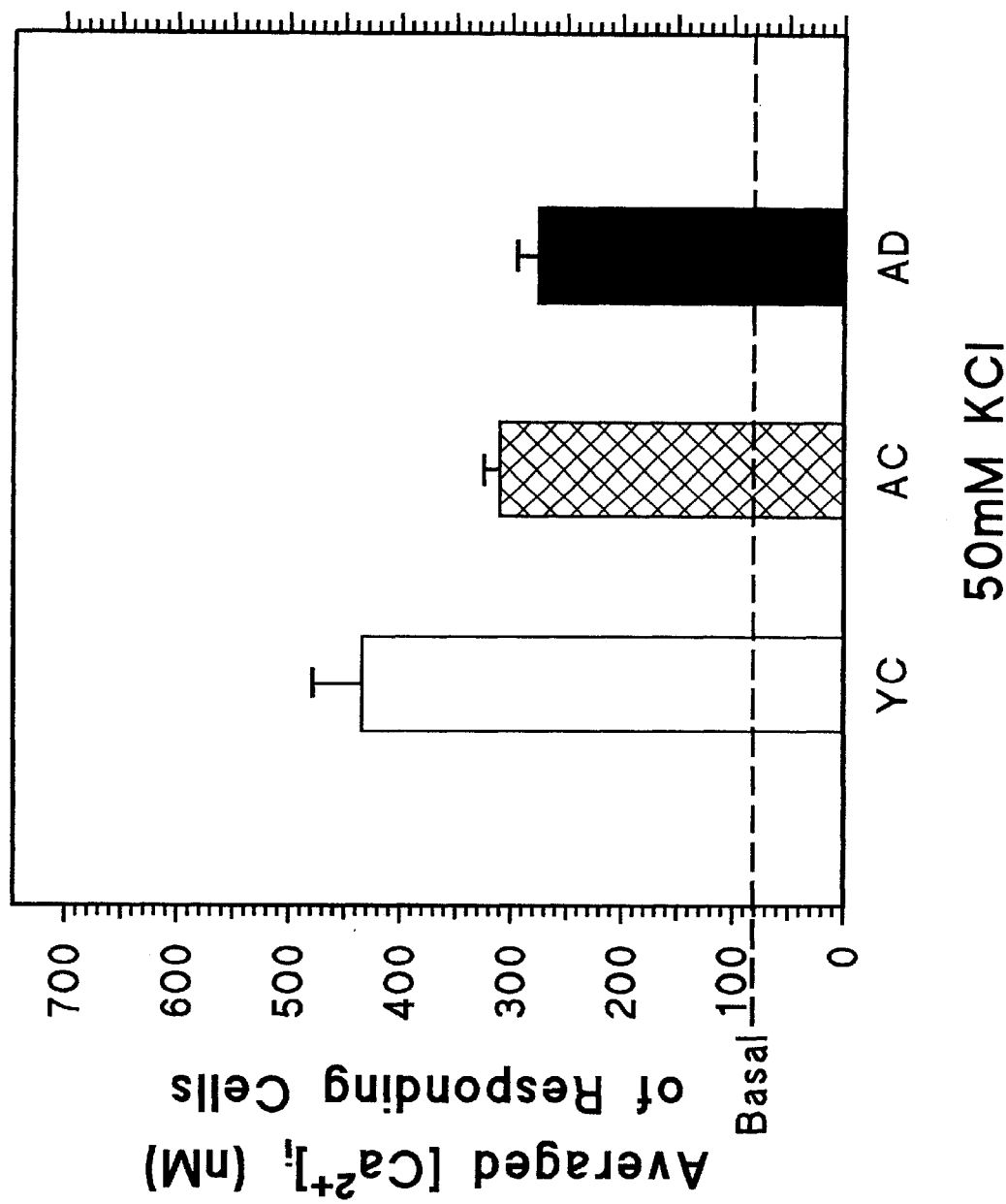
Figure 3C:
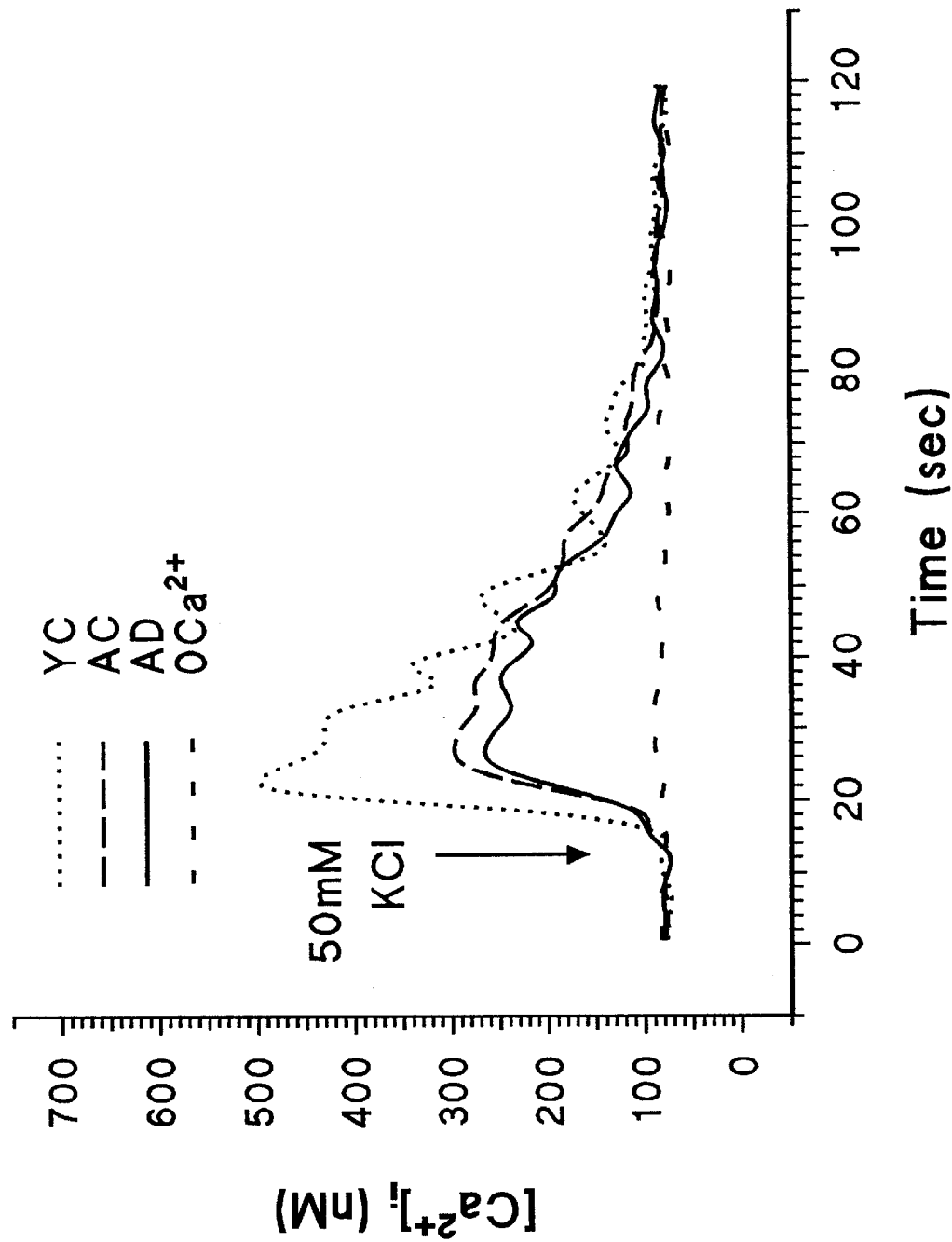

Depolarization of the fibroblasts by perfusion in elevated external potassium caused greater elevation of intracellular $Ca^{2+}$ ($[Ca^{2+}]_i$) in YC as compared to AC and AD cells (FIG. 3A–3C). This depolarization-induced $[Ca^{2+}]_i$ elevation was eliminated by lowering external calcium or by adding calcium channel blockers (FIG. 3C). High $K^+$-induced depolarization caused a marked $[Ca^{2+}_i]$ elevation (at least 100% increase) in all three groups (AD, n=13 cell lines; AC, n=10; YC, n=6). The proportion of responding cells and the $[Ca^{2+}]_i$ peak values were significantly higher in YC (n=183 cells) fibroblasts ($\chi^2$=14.22, p<0.001), as compared to AC (n=299) and AD (n=268) fibroblasts. The $[Ca^{2+}]_i$ peak occurs 10 to 15 seconds after stimulation, returning to basal levels after 100 seconds. No responses were observed if external calcium was lowered by addition of "nominally $Ca^{2+}$ free" solution or 5 mM EGTA (estimated free $Ca^{2+}$=0.04 μM) or $Ca^{2+}$ channel blockers (0.1 mM $LaCl_3$, 10 mM $CoCl_2$, 10 mM $NiCl_2$, 10 mM $CdCl_2$ or 10 μM nifedipine) before stimulation.

Depolarization of control fibroblasts by TEA also caused $[Ca^{2+}]_i$ elevation, that was eliminated by lowering external calcium or by adding calcium channel blockers. AD fibroblasts, however, only showed $[Ca^{2+}]_i$ elevation in elevated external potassium and had no $[Ca^{2+}]_i$ response with addition of even 100 mM TEA. Every AC cell line (N=10) and all but one YC cell line (N=6) had cells responding to TEA, while none of the thirteen AD cell lines examined had cells responding to 100 mM TEA ($X^2$=25.66, p<0.001) (Tables 3 and 5).

TABLE 3

Number of Cell Lines

| Condition | Total | Increase in $[Ca^{+2}]_i$ with 100 mM TEA |
|---|---|---|
| Young Controls | 6 | 5 |
| Aged Controls | 10 | 10 |
| Alzheimer's Patients | 13 | 0 |

1 mM TEA application elevated $[Ca^{2+}]_i$ in YC fibroblasts (n=130 cells) but not in AC (n=184) or AD (n=195) fibroblasts. 10 mM TEA elevated $[Ca^{2+}]_i$ in YC (n=176) and AC (n=231) but not in AD fibroblasts (n=204). Similarly 100 mM TEA elevated $[Ca^{2+}]_i$ in YC (n=532) and AC (n=417), but not in AD fibroblasts (n=738) ($X^2$=231.44, p<0.001). At least 417 cells were explored in each experimental group (Table 4). The $[Ca^{2+}]_i$ values of the responding cell were similar in YC and AC cells after 10 and 100 mM TEA addition. Basal $[Ca^{2+}]_i$ levels were virtually the same (S.E.<0.5 nM), therefore standard error bars are not distinguishable from the bar representing the arithmetic mean for those groups (FIG. 4B). Time courses of $Ca^{2+}$ response shows that the $[Ca^{2+}]_i$ peak occurs 20 to 30 seconds, after 100 mM TEA addition in YC and AC fibroblasts, returning to basal levels after 100 seconds. No response was observed in AD cells (10% of cells in a line with ≧100% elevation). Similarly, the response was absent in control cells when external $[Ca^{2+}]$ was lowered (FIG. 4C).

TABLE 4

Number of Cells

| Condition | Total | Increase in $[Ca^{+2}]_i$ with 100 mM TEA |
|---|---|---|
| Young Controls | 532 | 145 (27%) |
| Aged Controls | 417 | 119 (29%) |
| Alzheimer's Patients | 738 | 4 (0.5%) |

TEA-induced $[Ca^{2+}]_i$ elevations were repeated using a coded subsample that included Alzheimer's and control fibroblasts. Experiments and analyses were conducted without the experimenter's knowledge of the cell lines identity. The results were in complete agreement with the non-blind sample. None of the blindly examined AD cell lines (N=11) showed $[Ca^{2+}]_i$ elevation in response to TEA and all but one of the control cell lines (4 AC and 6 YC) had TEA responses ($X^2$=17.33, p<0.001 (Table 5)).

Since $[Ca^{2+}]_i$ elevation in response to high potassium was virtually the same for AC and AD cells, the lack of AD cells response to TEA is almost certainly due to dysfunction of $K^+$ channels and not to $Ca^{2+}$ channel dysfunction.

The $[Ca^{2+}]_i$ measurements are in agreement with the patch-clamp measurements insofar as they both indicate potassium channel dysfunction in the AD fibroblasts. See Table 5.

TABLE 5

| | | | | | | TEA Response | |
|---|---|---|---|---|---|---|---|
| Line # | Age | Gender | Race | Diag. Criteria | 113 $K^+$ Channel | Non Blind | Blind |
| Alzheimer's Disease Fibroblasts | | | | | | | |
| AG06840+[1] | 56 | M | W | Clinical - Fam. H. | – | – | – |
| AG06848+[2] | 55 | F | W | Clinical - Fam. H.* | – | – | N.T. |

TABLE 5-continued

| | | | | | | TEA Response | |
|---|---|---|---|---|---|---|---|
| Line # | Age | Gender | Race | Diag. Criteria | 113 K$^+$ Channel | Non Blind | Blind |
| AG07637+ | 55 | F | W | Clinical - Fam. H. | − | − | − |
| AG08170+ | 56 | M | W | Clinical - Fam. H. | − | − | − |
| AG06844+ | 39 | M | W | Clinical - Fam. H.* | N.T. | N.T. | − |
| AG04400† | 61 | F | W | Clinical - Fam. H. | N.T. | N.T. | − |
| AG04401† | 53 | F | W | Clinical - Fam. H.* | N.T. | − | − |
| AG05809 | 63 | F | W | Clinical - Fam. H. | − | − | N.T. |
| AG08243 | 72 | M | W | Clinical - No Fam. H. | − | − | − |
| AG07375 | 71 | M | W | Clinical - No Fam. H. | N.T. | − | − |
| AG07376 | 59 | M | W | Clinical - No Fam. H. | N.T. | − | − |
| AGO6263 | 67 | F | W | Clinical - No Fam. H. | − | − | − |
| AGO7377 | 59 | M | W | Clinical - No Fam. H. | N.T. | N.T. | − |
| Age-Matched Control Fibroblasts | | | | | | | |
| GM03524 | 67 | F | B | Normal | + | + | N.T. |
| AG06010 | 62 | F | W | Normal | + | + | + |
| AG06842+ | 75 | M | W | Normal-Fam. H. | + | N.T. | N.T. |
| AG07603+ | 61 | F | W | Normal-Fam. H. | + | + | N.T. |
| AG09878 | 61 | F | B | Normal | + | + | + |
| AG08044 | 58 | F | B | Normal | N.T. | + | N.T. |
| AG6241 | 61 | M | W | Normal | N.T. | + | N.T. |
| AG4560 | 59 | M | W | Normal | N.T. | + | N.T. |
| GM04260 | 60 | M | W | Normal | N.T. | + | N.T. |
| AG07141 | 66 | F | W | Normal | N.T. | N.T. | + |
| AG11363 | 74 | F | W | Normal | N.T. | N.T. | + |
| Young Control Fibroblasts | | | | | | | |
| GM03652 | 24 | M | W | Normal | + | + | + |
| GM03651 | 25 | F | W | Normal | + | + | + |
| GM02987 | 19 | M | W | Normal | − | − | − |
| GM04390 | 23 | F | W | Normal | + | + | + |
| GM03377 | 19 | M | W | Normal | − | + | + |
| GM08399 | 19 | F | ? | Normal | − | + | + |

Alzheimer's fibroblasts were from familial (N=8) and non-familial cases (N=5). Five (+) are members of the Canadian family 964, only 1 and 2 are immediate relatives (sibs). "‡" are members (sibs) of family 747. Autopsy confirmed Alzheimer's disease in three cases (*). Two of the age-matched control (N=11) cell lines are unaffected members of the Canadian family (964). All young control lines (N=6) are from normal and without AD family history individuals. Criterion $[Ca^{2+}]_i$ responses (to 100 mM TEA), indicates as +, were observed in all AC lines used and in all but one of the YC lines. The presence of the 113 pS K$^+$ channel is indicated by the "+" sign. None of the AD lines exhibited "positive" response. A blind protocol was conducted to measure TEA responses in Alzheimer's (N=11) and control (YC=6, AC=4) fibroblasts. The results exactly reproduced those of the non-blind sample: no AD cells line exhibited TEA responses and 9 out 10 control cells showed TEA responses, $x^2$=17.33, p<0.001. The notation "N.T." indicates cell line/conditions that were not tested.

EXAMPLE 3

Bombesin—$Ca^{2+}$ Diagnostic Test

Human skin fibroblasts listed in Table 3 were used. The average age for the AD cell lines used is 60.5±5.9 years; for the AC cell lines is 62.3±9.6 years; and for the YC cell lines is 21.5±2.2 years. The method of maintenance for the cells was described in Example 1, i.e., maintained 3–5 days at 37° C. in $CO_2$/air (5%/95%) to reach a density of 50, cells/mm$^2$ before calcium measurements. The number of culture passages were less than 19.

Bombesin was purchased from Calbiochem (San Diego, Calif.). Bombesin was stored as a 1 mM solution in distilled water. Fura-2 (acetyloxymethyl ester), fura-2 (pentapotassium salt) and omega-conotoxin (ω-CgTX) GVIA were from Molecular Probes (Eugene, Oreg.). Fura-2 AM was stored as a 1 mM solution in dimethylsulfoxide; fura-2 pentapotassium salt was stored as a 6 mM solution in potassium acetate, and ω-CgTX was stored as a 100 μM solution in distilled water. All of the chemicals except for phenytoin were maintained at −20° C. and protected from light.

The cells were incubated with 2 μM fura-2 AM in BSS (described in Example 1) at room temperature (21–23° C.) for 60 min. After being washed at least three times with BSS, the cells were used for measurement of $[Ca^{2+}]_i$ at room temperature. Cell fluorescence was measured as described in Example 2. Absolute calcium values were calculated as shown in Example 2.

Bombesin was added to the cells at a final concentration of 1 μM. Calcium mobilization levels were measured from −30 seconds to 150 seconds after bombesin treatment. (FIG. 5A) The particular experimental set up resulted in a maximum difference in $[Ca^{2+}]_i$ between AD cells and control cells at a time of 42 seconds after bombesin was added.

Forty two (42) seconds after bombesin treatment, in the absence of extracellular $Ca^{2+}$, the $[Ca^{2+}]_i$ levels in Alzheimer's disease cells are much larger (p<0.000) than in age-matched and young controls. The numbers of cell lines (N) are 10, 8, and 6 for Alzheimer's disease, age-matched and young cells, respectively. The values are means± S.E.M. (FIG. 5B)

Bombesin stimulated IP$_3$-induced $Ca^{2+}$ release from intracellular storage sites in fibroblasts from all groups, but it caused a larger and more prolonged response in AD fibroblasts. This larger and prolonged response in AD cells was independent of extracellular $Ca^{2+}$. On the other hand, the IP$_3$-mediated Ca$^{2+}$ responses in AC and YC cells were followed by Ca$^{2+}$ entry. When this Ca$^{2+}$ entry was diminished by removal of extracellular Ca$^{2+}$, or blocking with inorganic Ca$^{2+}$ blockers, the bombesin-elicited Ca$^{2+}$ responses in control cells were found to return to the basal level faster than in AD cells (FIG. 5A). The results shown in FIG. 5A are for cells washed with BSS nominally free of Ca$^{2+}$.

Since Ca$^{2+}$ influx induced by bombesin was not observed in AD cells, this pathway of Ca$^{2+}$ entry following the decrease of stored calcium seems to be altered. This test independently confirmed the diagnoses made by the previously described test based on potassium channel dysfunction. In particular, the Ca$^{2+}$ responses at 42 sec after 1 μM bombesin stimulation in AD fibroblasts in the absence of extracellular Ca$^{2+}$ were always higher than 300 nM. In contrast, the [Ca$^{2+}$]$_i$ in AC and YC were less than 300 nM and 200 nM, respectively (FIG. 5B).

In a variation on the above experiment, Ca$^{2+}$ responses were induced by 1 μm bombesin in the presence of extracellular calcium. In the presence of 2.5 mM extracellular CaCl$_2$, 1 μm bombesin elicited a fast peak of [Ca$^{2+}$]$_i$, followed by a sustained phase for YC and AC cells, but not for AD cells. (FIG. 6A). This difference was evident 90 seconds after bombesin application and with a significance level of p<0.001. (FIG. 6B). This difference in response of AD and non-AD cells to bombesin in the presence of extracellular calcium can be used to provide a "yes or no" diagnosis of AD. Detection methods similar to those described above with respect to the second embodiment of the invention involving the diagnosis of AD by detecting differences between non-AD and AD cells in response to select potassium channel blockers (e.g., TEA) may be used. Furthermore, the combination of this diagnostic test with any one of the above diagnostic tests further increases the confidence level of a correct diagnosis as AD or non-AD.

EXAMPLE 4

Responses In Neuropathological Non-AD Fibroblasts

Using the techniques described in Examples 2 and 3, cells from donors with other diseases were measured for intracellular calcium levels in response to either TEA or bombesin.

Fibroblasts from a Parkinson's disease donor had normal TEA (indicated as +) and bombesin responses ("N"), and did not significantly differ from responses observed in the age-matched control group. Fibroblasts from two schizophrenic patients also had normal TEA and bombesin responses. In addition, normal TEA responses were observed in five out of seven cases of Huntington's disease, and the bombesin response was normal in all Huntington's cases. Furthermore, normal TEA and bombesin responses were observed in four out of four cases of Wernicke-Korsakoff disease (Table 6). These responses are significantly different from those of AD fibroblasts to the level of p<0.0001 (Fisher's exact test). "*" indicates autopsy confirmation.

TABLE 6

| Line # | Age | Gender | Race | Condition | TEA | Bombesin |
|---|---|---|---|---|---|---|
| AG08395 | 85 | F | W | Parkinson's* | + | N |
| GM01835 | 27 | F | W | Schizophrenia | + | N |
| GM02038 | 22 | M | W | Schizophrenia | + | N |
| GM06274 | 56 | F | W | Huntington's | + | N |
| GM02165 | 55 | M | W | Huntington's | + | N |

TABLE 6-continued

| Line # | Age | Gender | Race | Condition | TEA | Bombesin |
|---|---|---|---|---|---|---|
| GM00305 | 56 | F | W | Huntington's | − | N |
| GM01085 | 44 | M | W | Huntington's | + | N |
| GM01061 | 51 | M | W | Huntington's | + | N |
| GM05030 | 56 | M | W | Huntington's | − | N |
| GM04777 | 53 | M | W | Huntington's | + | N |
| 7504 | 50 | M | W | Wernicke-Kors. | + | N |
| 7505 | 52 | F | W | Wernicke-Kors. | + | N |
| 7507 | 63 | M | W | Wernicke-Kors. | + | N |
| 7508 | 64 | M | W | Wernicke-Kors. | + | N |

Every reference cited hereinbefore is hereby incorporated by reference in its entirety.

EXAMPLE 5

Characterization of Cp20 Protein

Materials & Methods

Animal tissue. Optic lobes from fresh squid (*Loliog pealei*, Calamari, Inc.) were dissected and frozen on liquid nitrogen and stored at −80°. *Hermissenda crassicornis* were obtained live from Sea Life Supply, Sand City, Calif.

Purification of cp20. 150 squid optic lobes were added to 100 ml buffer (10 mM Tris-HCl pH 7.4 20 μg/ml leupeptin, 20 μ/ml pepstatin, 50 mM NaF, 1 mM EDTA and 1 mM EGTA). PMSF and dithiothreitol (DTT) were added to 0.1 mM and 200 mM, respectively, and the optic lobes were homogenized at 4° in a high-speed homogenizer followed by sonication. The homogenate was centrifuged (100,000 g×90 min) and the supernatant was filtered through an 0.22 μm filter and passed through an Amicon filter (30 kDa cutoff). The low MW fraction was then concentrated on a second filter (3 kDa cutoff) followed by concentration of 100 μl in Centricons (Amicon Corporation) pretreated with BSA. Use of untreated Centricons led to complete loss of protein.

The retained fractions were injected onto an AX-300 anion-exchange HPLC column (1×25 cm, Synchropak. The column was eluted at 2 ml/min and 10° C. with a gradient of 0–0.6M buffer (1M KAc, pH adjusted to 7.4 with HAc) for 20 min. followed by 0.6M buffer for 40 min. Each chromatogram was statistically analyzed by creating a correlation curve with the $t_R$ of each peak plotted against the $t_R$ of all the peaks in a reference chromatogram, a chromatogram of proteins from 5 eyes dissected from a group of Hermissenda conditioned in a previous experiment, as described previously (Nelson T., et al. (1990). *Science* 247, 1479–1483.). Briefly, Hermissenda conditioning consist of 75 pairings of a 3 sec light, which terminated with 2 sec rotation. These sessions of this training were concluded on successive days. The animals demonstrate associate learning when the conditional stimulus, light, elicits the response elicited before only by the unconditioned stimulus, rotation. A candidate cp20 peak was considered to match only if its $t_R$ fit within±0.2% to the expected $t_R$ and if 10 or more other peaks could also be matched with the same precision. If the cp20 peak could not be unequivocally identified, or a unique correlation curve could not be constructed, the preparation was discarded. Fractions were collected in polypropylene tubes containing Triton X-100 at a final concentration of 0.2 mM.

A portion of each HPLC fraction surrounding the final cp20 peak was analyzed by SDS gel, blotted, stained with colloidal gold (CG) and enhanced with silver (IntenSE BL, Amersham). If densitometry of the blot indicated less than 85% purity, the preparation was re-purified or discarded.

Cation-exchange HPLC. In several experiments, the cp20 was further purified by cation-exchange HPLC (S-300, 4.6×250 mm, Synchropak). The column was eluted at 0.5 ml/min for 10 min with 0.2M LiCl pH 6.0, followed by a gradient of 0.02 to 0.7M LiCl over 60 min. Each fraction was analyzed for GTPase and analyzed by SDS gel. Some samples were analyzed by CM300 HPCL (Synchropak) with a gradient of 0–1M KAc over 30 min.

Reversed-phase HPLC. The C18 column (Macrosphere 300, 5 μ) was eluted at 0.35 ml/min with 20–100% ACN/ 0.1% TFA over 90 min followed by 100% ACN/0.1% TFA for 90 min.

GTPase was measured as described previously (Nelson T., et al. (1990). *Science* 247, 1479–1483.). Briefly, fractions were incubated for 120 min with $-^{32}$P-GTP in the presence of 100 mM Tris-HCl, pH 7.4 and 10 mM $MgCl_2$. The $^{32}$P-(P-$^{32}$ inorganic phosphate) released was extracted into benzene after reaction with silicotungstic acid and the amount of radioactivity was measured in a scintillation counter. Peptides and proteins were quantitated using colloidal gold reagent (Aurodye, Amersham) (Hunter J., Hunter S. (1987). *Anal. Biochem.* 164, 430–433.) as modified in (Nelson T., et al. (1990). *Science* 247, 1479–1483.).

Photoaffinity labeling. Samples were incubated in closed 0.5-ml tube for 30' at 25° with α-$^-$P-GTP, irradiated with UV light and analyzed by SDS gels as described previously (Nelson T. J., et al. (1991). *J. Neurochem.* 57, 2065–2069) followed by autoradiography.

Monoclonal antibodies. Cp20 from 20 squid optic lobes was injected into mouse spleen. A single injection of approximately 50 nanograms (ng) of protein bound to nitrocellulose was administered. The spleen lymphocytes were fused with mouse myeloma cells X63-Ag8-653 (American Type Tissue Culture Collection). Hybridoma cells were selected by ELISA using plates coated with optic lobe extract. Squid optic lobe extract was made by homogenation of squid optic lobes in water and centrifugation at 5–10,000 g for 10–20 min. Elisa plates were coated by filling each well with 0.1 ml of optic lobe extract and incubating at room temperature for >1 hour. The hybridoma was cloned by limiting dilution and cultivated in serum free media (Modified Eagle Medium). The IgM fraction was purified by precipitation with $(NH_4)_2SO_4$ and dialyzed against PBS.

Polyclonal Antibody. A synthetic peptide corresponding to ARLWTEYFVIIDDDC (SEQ ID NO. 9) (with 2 glutamates for solubility and cysteine for conjugation to KLH) was synthesized, conjugated with keyhole limpet hemo-cyanin (KLH) and suspended in Freunds adjuvant. Approximately 0.1 mg peptide was injected intraperitonally into one rabbit biweekly, over 4 months. Test bleeds were obtained every two weeks and tested for efficacy at recognizing squid Cp20 in Western blots of crude optic lobe homogenate.

Figure 7D:
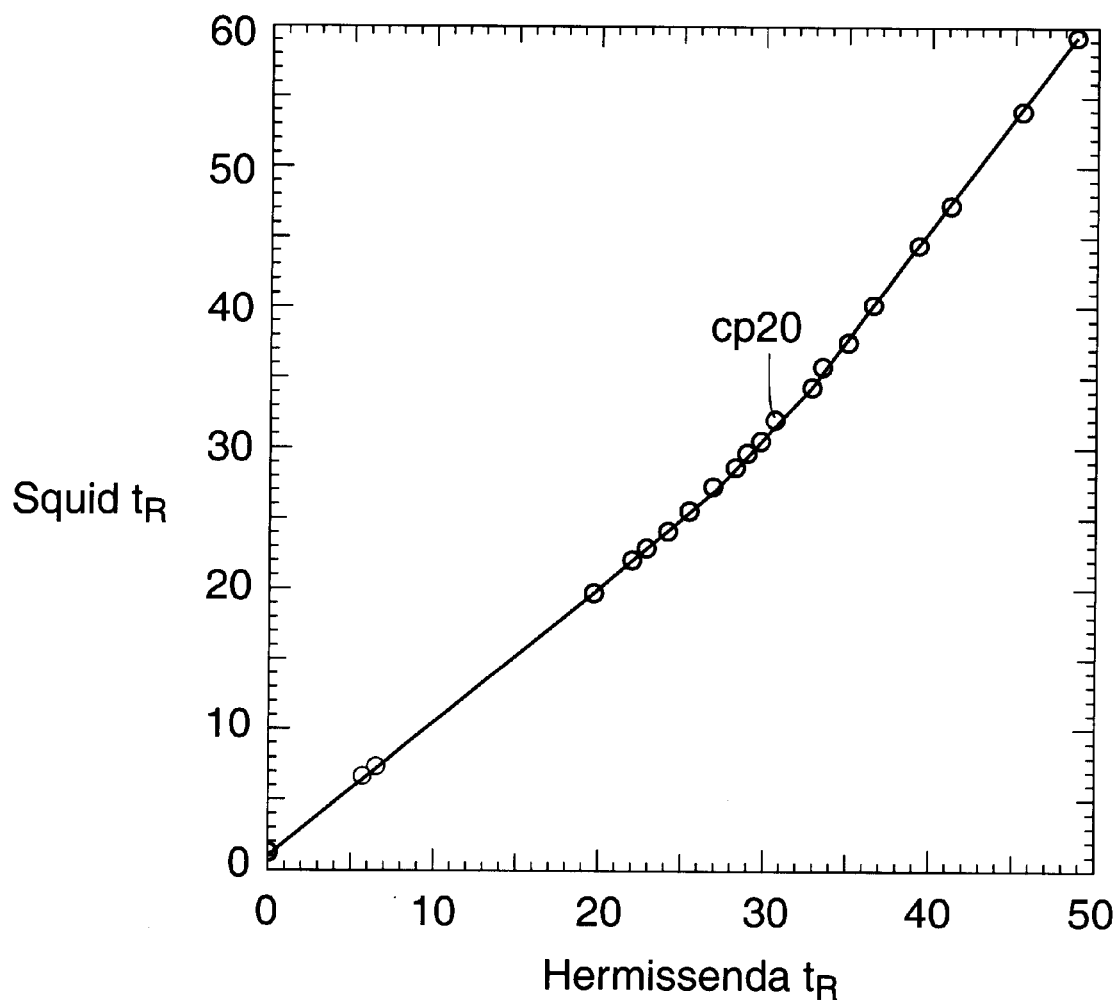

Western Blot Analysis. Up to 40 ug (micrograms) protein per lane was applied to 4–20% gradient Tris-glycine polyacrylamide gels (Novex Corp., San Diego, Calif.) and blotted onto reinforced nitrocellulose. After blocking at 4 for 12 hr with BSA, the blots were incubated with polyclonal antiserum at a dilution of 1:600 or with monoclonal antibody (ammonium sulfate fraction) at a dilution of 1:2000 for 2 hr at room temp. Cp20 was visualized using alkaline phosphatase-conjugated rabbit anti mouse (Sigma) or goat anti rabbit second antibodies (Sigma) (1:2000) and developed with NBT (nitro blue tetrazolium chloride)-BCIP. Because a single Hermissenda CNS contains only 8 μg of total protein and subnanogram quantities of cp20, it was necessary to use a different source (squid optic lobe) in order to obtain adequate quantities of cp20 for characterization. Computer-assisted pattern matching of the HPLC profiles demonstrated that the HPLC profiles of cytosolic proteins from squid optic lobe and Hermissenda eye were quite similar (FIGS. 7B, 7C, 7D), with the exception of the cp27 peak (29.5 min), which was much smaller in squid than Hermissenda, and 2–3 other peaks which were larger in squid.

To determine whether the AX-300 HPLC column adequately separates G proteins, squid homogenate was chromatographed on AX-300 and the molecular weights of all GTPases were determined. 84% of the GTPase activity from squid eluted in large unresolved peaks at 12–18 and 19–21 min. Ras, rap and Sarlp, measured by Western blotting of HPLC fractions, eluted at 22.8, 20.5, and 19.4 min, respectively (not shown). Thus, the HPLC column was highly efficient at separating cp20 ($t_R$30 min) from other GTP-binding proteins. Interestingly, no G proteins were detected in the large non-retained peak (6–10 min) (see FIG. 7A).

Figure 8A:
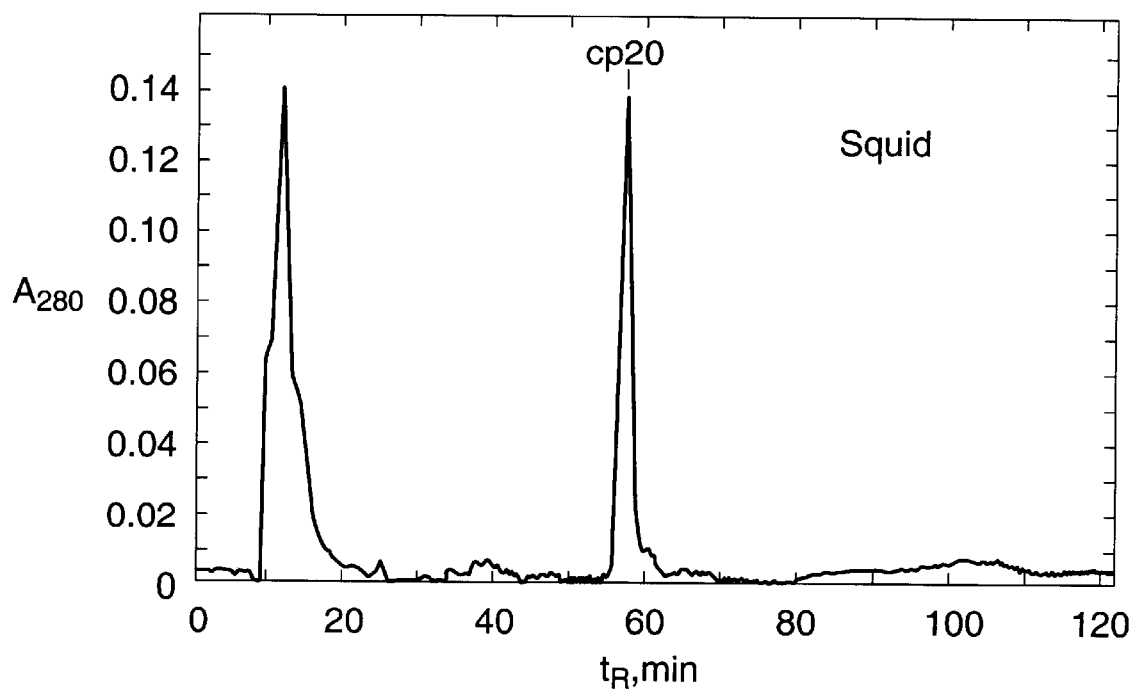
FIG. 8. RP-HPLC $A_{280}$ profile of purified squid cp20 (Upper). The peak at 15' is the non-retained fraction, containing DTT and buffer components. Lower:RP-HPLC rechromatography of a cp20 peak from one Hermissenda CNS from an earlier experiment (Nelson T., et al. (1990). Science 247, 1479–1483.). Peaks at 4, 12, 15, 42, 46, and 78 min are buffer components. Flow rate: 0.5 ml/min.
Figure 8B:
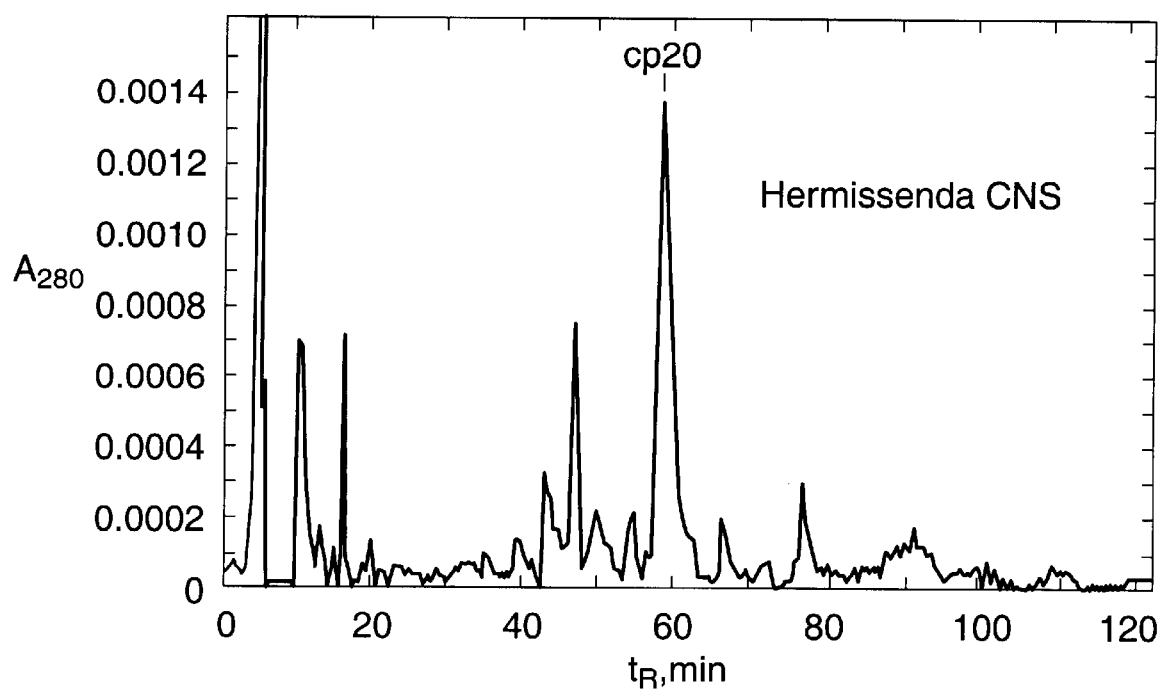

To test the purity of the cp20, squid cp20 was reanalyzed by RP-HPLC. After the large non-retained peak caused by DTT and salts, a single peak was observed (FIG. 8). Its GTPase activity was difficult to measure, presumably due to the harsh conditions (100% ACN/0.1% TFA). No activity was seen at other positions. The tR is comparable to that seen previously with cp20 from Hermissenda eye and CNS (Nelson T., et al. (1990). *Science* 247, 1479–1483.).

Figure 9A:
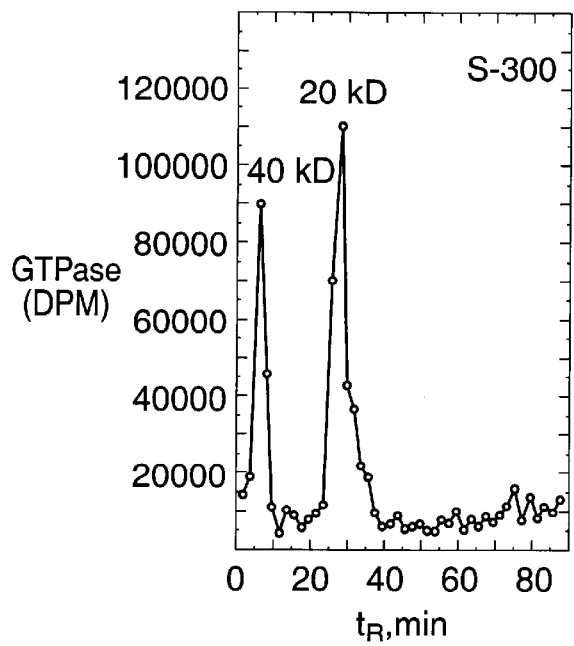
FIGS. 9A–9D. S-300 (9A) and CM-300 (9B) cation exchange HPLC GTPase profile of purified squid cp20. Half of each fraction was analyzed for GTPase activity and half was analyzed on SDS gels. After 18 min in (9B), the GTPase baseline increased dramatically due to interference in the assay by the HPLC solvent. (9C) GPC-100 size-exclusion HPLC GTPase profile of squid cp20 purified in the absence of DTT (dithiothreitol). By this stage, most of the cp20 has dimerized. (9D) Specificity of anti cp20. Supernatant from 10 Hermissenda CNSs was applied to an AX-300 column. Each fraction was blotted, reacted with mouse anti-cp20 and developed with AP (alkaline phosphatase)/BCIP (bromo-4 chloro-3-indolyl phosphate). The blot was scanned, converted to O.D., and integrated by computer. The large peak at 31 min coincided with the cp20 peak in the $A_{280}$ profile.
Figure 9B:
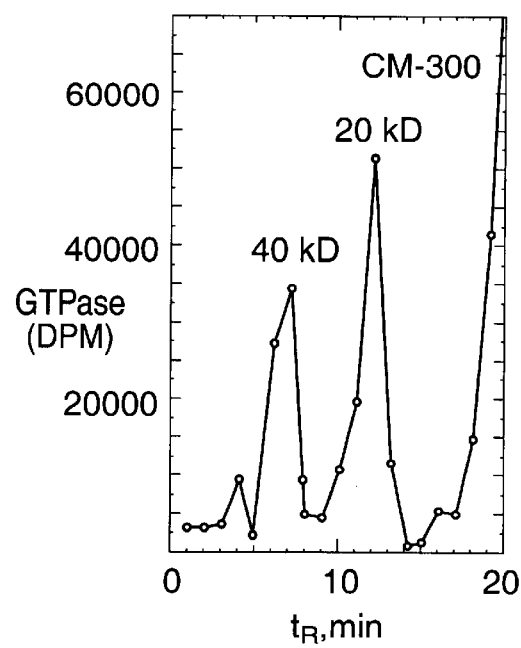
Figure 9C:
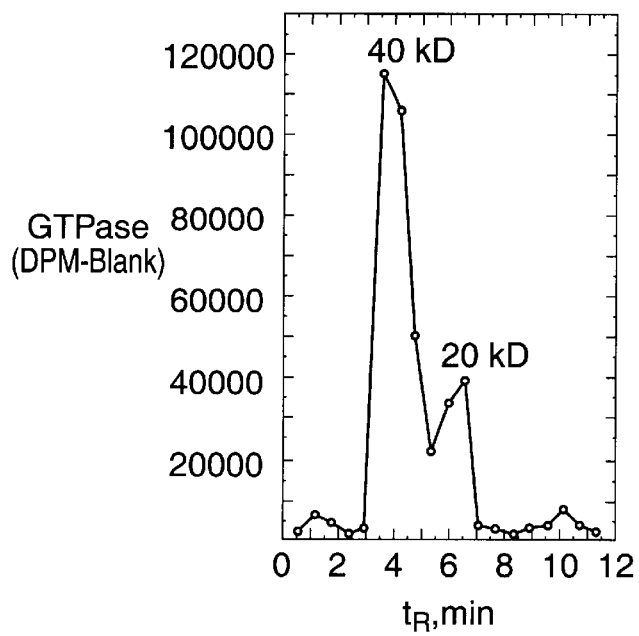
Figure 10A:
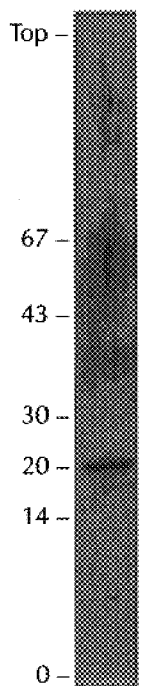
FIGS. 10A–10L. (10A, 10B) Interconversion of the 20 kDa and 40 kDa forms of cp20 by DTT. Cp20 purified by anion-exchange HPLC in the absence of DTT was fractionated on a non-denaturing gel. The 40 kD region of the gel was eluted, reacted with DTT(10A) or water (10B), and analyzed by SDS-PAGE. (10C)SDS gel of purified squid cp20. (10D–10G) Western blots of squid supernatant (10D), Hermissenda supernatant (10E), and rabbit hippocampus particulate (10F) and supernatant fraction (10G), reacted with anti-cp20 monoclonal AB. (10H) Western blot of cross-reaction of purified squid cp20 with anti Giα. (Staining: 10A–10C, CG (colloidal gold); 10D–10G, AP/BCIP; 10H–10L, Horseradish peroxidase (HRP)/ diamino-benzidine (DAB). (10I–10L) Western blots of (10I, 10J), ARF (10K) yeast Sarlp, and (10L) squid cp20 reacted with anti-cp20 polyclonal antibody (Staining: HRP/DAB). (10J) has been contrast-enhanced to more clearly show the ARF band in (10I).
Figure 10B:
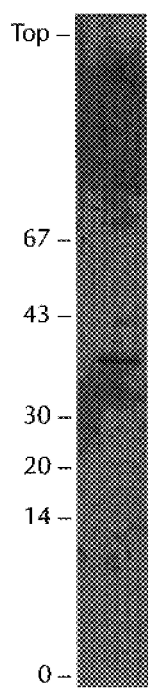

Cp20 form both squid optic lobes and Hermissenda CNS was also rechromatographed by S-300 and CM-300 cation exchange HPLC (FIGS. 9A, 9B). Each fraction was tested for GTPase activity and analyzed on SDS gels. In both cases, two peaks of GTPase activity were detected, with Mr's of 20 and 40 kDa, suggesting a homodimeric structure. In a similar experiment, cp20 purified in the absence of DTT was fractionated on a non-denaturing gel. When the 40 kDa section of the gel was eluted, reacted with DTT, and analyzed by SDS-PAGE, a 20 kDa band was observed. In contrast, in the absence of DTT, only a 40 kDa protein band was observed (FIGS. 10A, 10B). Thus, the 40 kDa protein is not an impurity, but dimerized cp20.

Further evidence of dimerization was obtained by photoaffinity-labeling the 20- and 40-kDa peaks with $^{32}$P-GTP and analyzing by SDS-PAGE. 32p-labeled bands with Mr's of 40 and 20 kD were found in the lanes corresponding to both the 40 and 20 kD HPLC peaks (not shown). Thus, the 40 kD band was not an artifact of photolabeling but is caused by natural dimerization. However, it is not yet known whether dimerization occurs under physiological conditions.

Figure 10C:
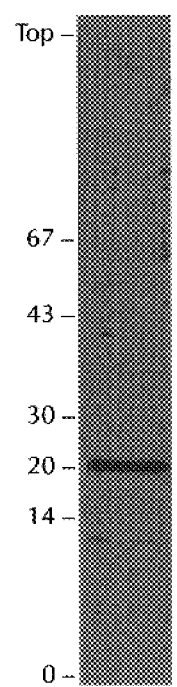
Figure 10D:
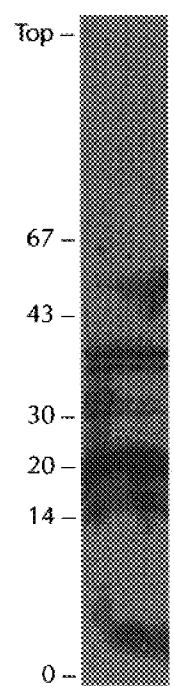
Figure 10E:
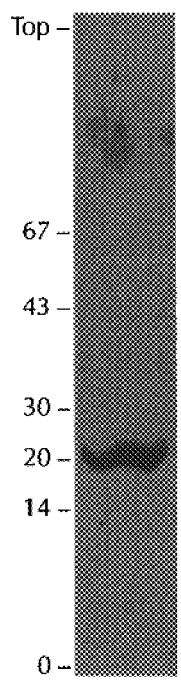
Figure 10F:
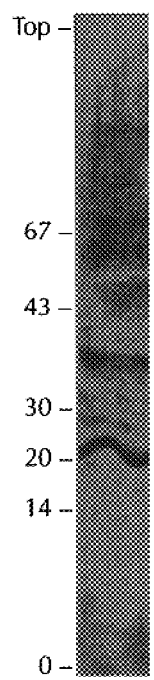
Figure 10G:
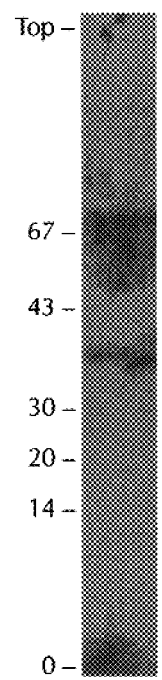

A monoclonal antibody prepared against purified squid cp20 also recognized 20 kD and 40 kD bands in squid supernatant, and a 20 kD band in Hermissenda (FIGS. 10D, 10E). The proportion of staining at 40 kD increased if the samples were allowed to stand at 40° before analysis. Despite the fact that the antibody was raised against squid protein, it reacted more strongly with Hermissenda cp20. Cp20 was also detected in rabbit hippocampus particulate fraction, but not in the supernatant (FIGS. 10F, 10G).

Figure 9D:
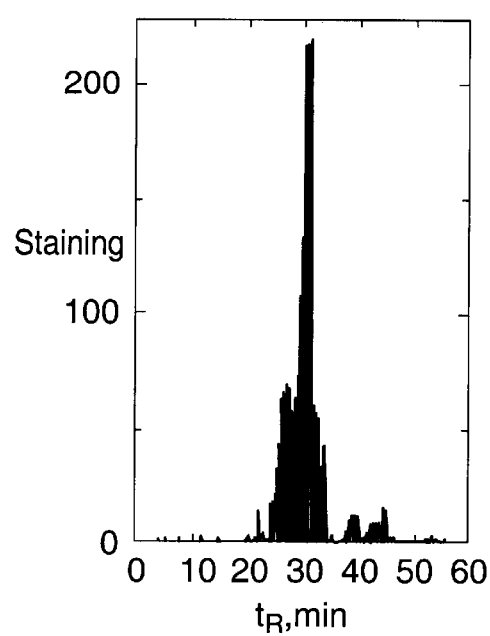

Western blots of HPLC fractions from Hermissenda supernatant revealed a larger peak at 31 min coinciding with cp20, and a smaller peak at 28 min, possibly the dephosphorylated form of cp20 (FIG. 9D).

Figure 10H:
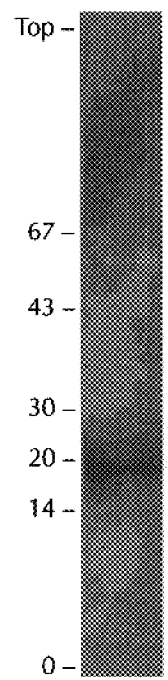
Figure 10I:
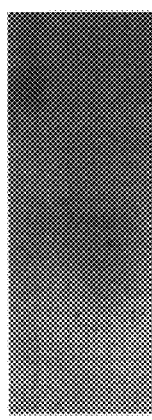
Figure 10J:
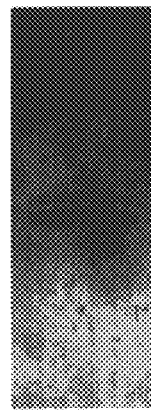
Figure 10K:
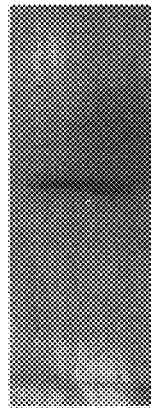
Figure 10L:
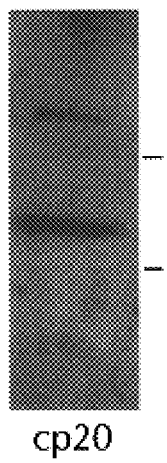

Squid cp20 did not cross-react with pan-ras, anti-ARF or anti-rap monoclonals (not shown). Cp20 weakly cross-reacted with anti-Giα, an antibody against the GTPase active site (Goldsmith P., et al. (1988). *J. Biol. Chem.* 263, 6476–6479.) (FIG. 10H). This antibody did not cross react with a sample of cloned ras, suggesting that cp20 is more closely related to the trimeric G proteins than to ras.

A polyclonal antibody against the peptide ARLWTEY-FVIIDDDC (SEQ ID NO. 9) which is derived from the largest tryptic peptide of Cp20 (tR 40 min in FIGS. 12A and 12B) cross-reacted with Cp20 and Sarlp, and weakly cross-reacted with cloned ARF (FIGS. 10I–10L), but not with ras, also consistent with the conclusion that cp20 is more closely related to ARF-family proteins than to ras.

Figure 11A:
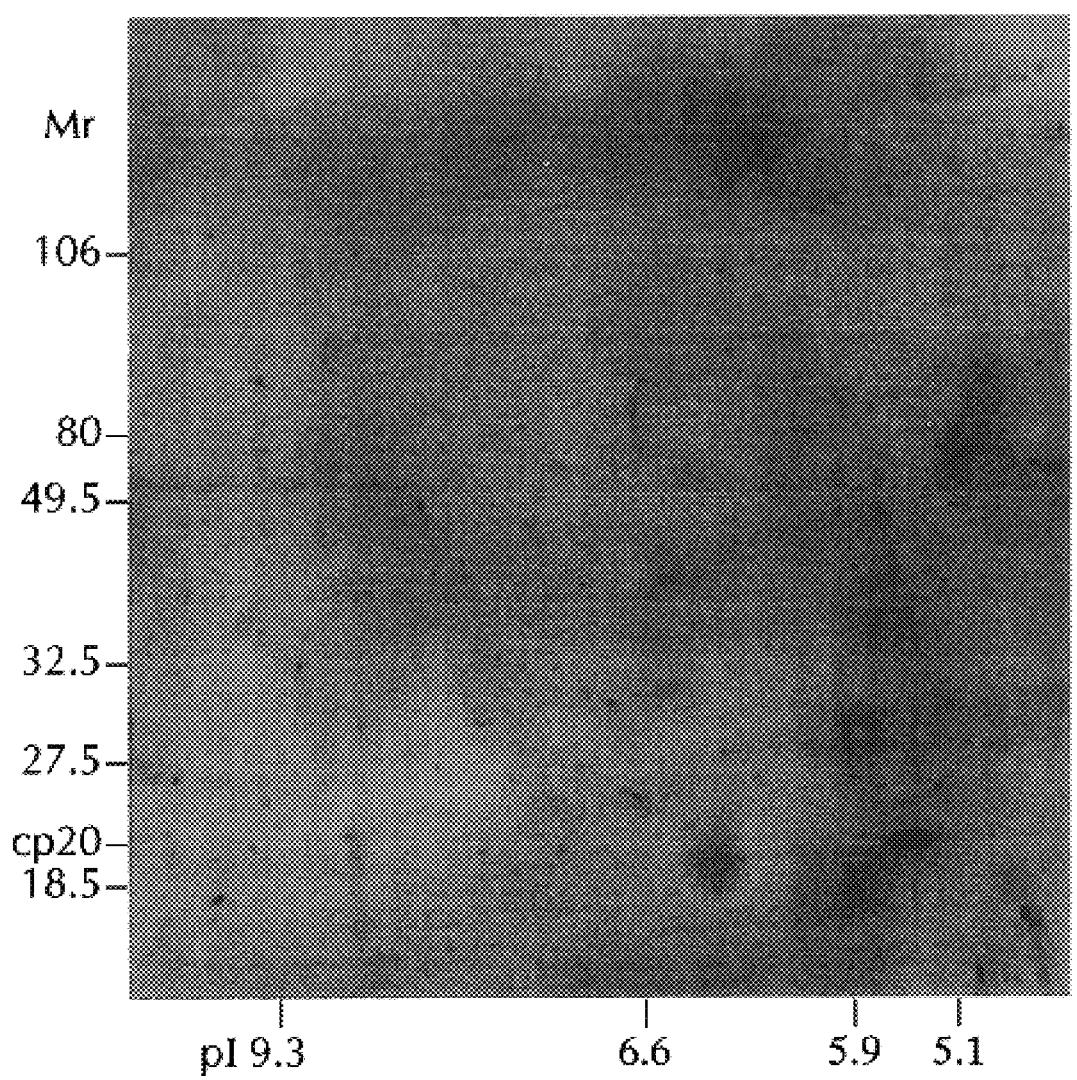
FIGS. 11A–11B. 2D gel of squid cp20 (11A) and Hermissenda cp20 (11B), purified in the presence of DTT (colloidal gold stain).
Figure 11B:
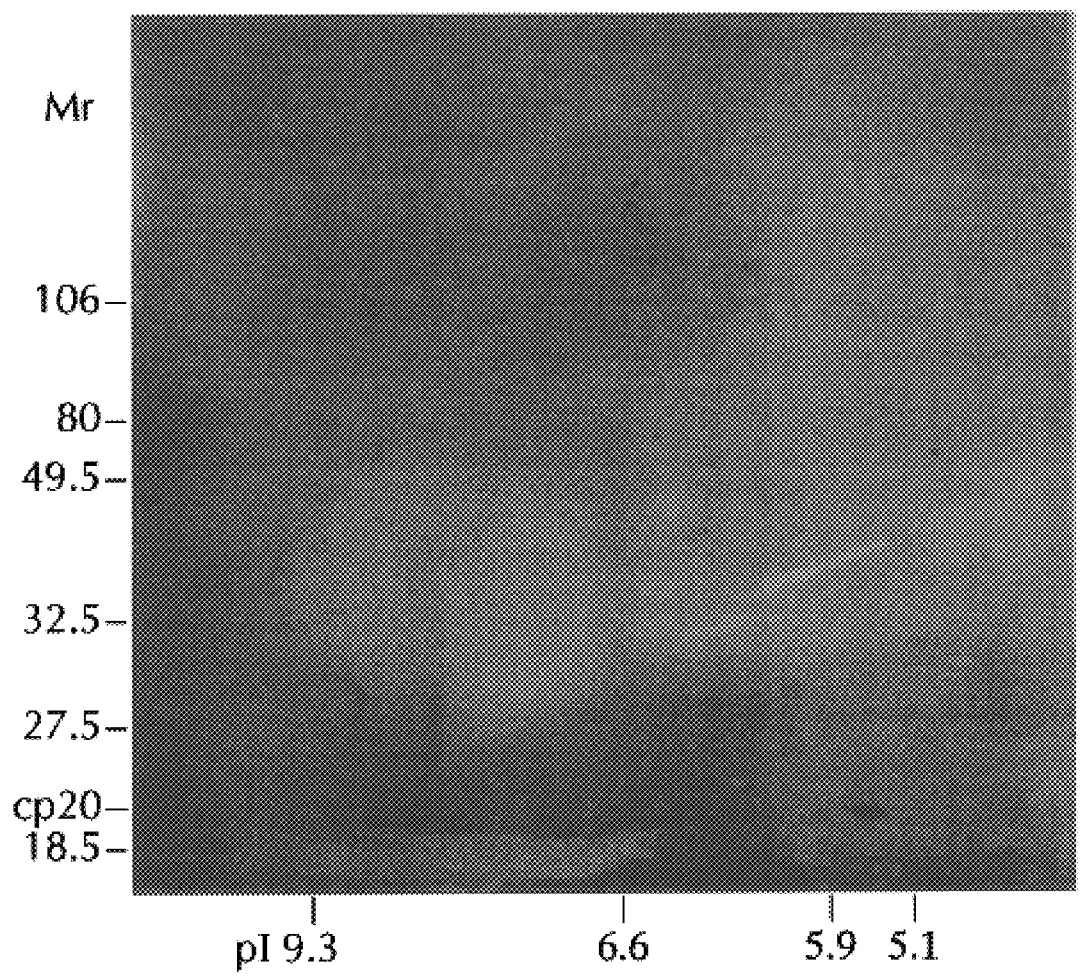

Using the ability of DTT to convert cp20 into monomers, it was possible to purify cp20 to apparent homogeneity with two ultrafiltration steps followed by a single HPLC column step (FIGS. 10C, 11A). The stoichiometry of $^{32}$P-GTP binding to purified squid cp20 in several preparations ranged from 0.90–0.95, indicating that the protein was 90–95% pure. The protein when pure adsorbed to concentrators and polyproplyene test tubes unless Triton X-100 was added. The pI of squid cp20 was 5.2 by electrophoresis, and 5.86 by chromatofocusing. Hermissenda cp20 was identical to squid in both Mr and pI (FIG. 11B).

Sequencing of 5 tryptic peptides from squid cp20 revealed an overall 50% identity (23/46 amino acids) with Sarlp, a 21 kDa GTP-binding protein in the ARF family (Nakano A. Muramatsu J., (1989). *J. Cell Biol.* 109, 2677– 2691.) (FIG. 12A). Several of the non-matching residues in Cp20 and Sarlp are conservative substitutions (e.g., D→E, N→D, A→L). Sarlp is involved in the transport of proteins from ER to the Golgi apparatus (Nakano A. Muramatsu J., (1989). *J. Cell Biol.* 109, 2677–2691; Barlow C., et al. R. (1993). *J. Biol. Chem.* 268, 873–879; Oka T., et al. (1991) *J. Cell Biol.* 114, 671–679.). This sequence is also similar to a lesser degree to ARF and the GIα trimeric G protein but shows little similarity to ras.

Injection of cp20 into Hermissenda photoreceptors causes a marked reduction of the K+ currents $I_A$ and $I_{K+Ca2+}$, both of which are known to be reduced after associative learning (Alkon D. L., et al. (1982) *Science* 221, 1201–1203.). Injection of cp 20 also reproduces the structural changes in neuronal architecture previously observed after associative learning (Collin C., et al., *Biochem. Biophys. Res. Commun.*, in press.).

Several other GTP-binding proteins, including ras (Santos E., et al. (1988) *J. Biol. Chem.* 263, 9853–9858.), are known to form homodimers. In Hermissenda, rap also exists predominantly as a 46 kDa dimer (McPhie, D., personal communication). Because of the homology with Sarlp and ARF, cp20 probably is a member of the ARF family of low-MW GTP-binding proteins. In yeast, these proteins, including Sarlp, ARF, and YPT1, are involved in several steps of vesicle transport (Nakano A. Muramatsu J., (1989). *J. Cell Biol.* 109, 2677–2691. Alkon D. L., et al. (1990). *Proc. Natl. Acad. Sci.* (USA) 87, 1611–1614. Walker M., et al. (1992) *J. Biol. Chem.* 267, 3230–3235. Segev N., et al. (1988) *Cell* 52, 915–924.). A group of low-MW GTP-binding proteins has also been found to be associated with rapid axonal transport (Bielinski D. F., et al. (1989) *J. Biol. Chem.* 264, 18363–18367.). Thus, the similarity between cp20 and ARF-related proteins is consistent with the observed effects of cp20 on regulation of intraaxonal particle movement (Moshiach S., et al. (1993). *Brain Res.* 605, 298–304.). Association with vesicle membranes is also consistent with cp20's strong retention on C18 HPLC, which suggests that it has a lipophilic character. It has not yet been established which of the observed physiological effects of cp20 are directly attributable to cp20 and which are mediated by some other molecule, such as protein kinase C. Ras is also able to produce some of the effects of microinjected cp20, but is only effective at much higher concentrations (Collin C., et al. (1990) *Science* 250, 1743–1745.). Like cp20, ARF is more closely related to the α-subunit of trimeric G proteins than to ras (Sewell J., Kahn R. (1988) *Proc. Nat. Acad. Sci.* (USA) 85, 4620–4624.). The present data show cp20 is not ras but a new protein related to Sarlp and ARF.

The unambiguous classification of cp20 within a category of proteins involved in signalling and regulation of molecules between the ER and Golgi, together with its previously-established impact on neuronal function and structure and its causal implication in memory storage, provide the first evidence suggesting the possibility that memory storage could depend in part on regulation of particle trafficking among intraneuronal organelles.

EXAMPLE 6
Alterations In Cp20 Protein Levels In Alzheimer's Patients

Materials and Methods

Cell lines and procedures for cell culture. Human skin fibroblasts were grown to confluence in 75 cc growing surface culture flasks (Falcon) containing Dulbecco's modified Eagle's medium (DMEM, Gibco), supplemented with 10% fetal calf serum (Gibco). Cells from thirteen AD individuals [AG06840, AG06844*, AG06848*, AG08170, AG7637, AG08527* familiar alzheimer's disease (FAD) # 964, 4 males, 2 females); AG04401 (FAD, # 747, female); AG07376, AG07377, AG06262, AG05770*, AG06263, AG07375 (Non-FAD, 5 males, 1 female), 60.4±6.05 years (Mean±SD), "*"=autopsy confirmation], nine AC [GM04260, GM04560, GM03524, AG07303, AG08044, AG09878, AG07141, AG07310, AG06241 (all apparently normal, without known family history individuals, 3 males, 6 females), 62.89±5.16 years], and four "escapees" [AG06838+, AG06842+, AG07665$^{555}$ (members of family # 964); AG08265+ (member of family # 2090), 67.25±6.85 years, "+"= immediate relative affected (parents and/or siblings), "‡"=uncle affected] were used for Cp20 and total protein assessments. These cells lines are available through National Institute of Aging, 1991 Catalog of Cell Lines (1991); National Institute of General Medical Sciences, 1990/1991 Catalog of Cell Lines (NIH Publication 91-2011, 1990). The same AC cell lines were also grown in duplicate. One set of cells was treated with 10 nM β-amyloid (in DMSO) and the other with DMSO alone for 48 h. The total DMSO was less than 0.1% in both groups. β-amyloid 1–40 peptide (Bachem) was prepared in DMSO (230 μM) and later diluted in distilled water (Picopure®, Hydro) to reach the final incubation concentration of 10 nM. This low β-amyloid concentration has been shown to have specific AD-like effects on a 113 pS K+channel, without altering basal levels of intracellular $Ca^{2+}$ or causing other non-specific cell damage (R. Etcheberrigaray, E. Ito, C.S. Kim, D. L. Alkon, *Science* 264, 276 (1994)).

Procedures for cell homogenization and protein extraction. Culture medium was removed by aspiration and replaced with ≈20 ml of cold (4° C.) PBS. The cells were scraped from the flasks and centrifuged at 10,000 g for 10 min. at (4° C.). Supernatant was discarded, the pellet washed with 1 ml PBS and then inverted to remove any remaining PBS for about 2–3 min. Pellets were washed with 1 ml of "homogenization buffer" (50 mM NaF, 1 mM EDTA, 1 mM EGTA, 20 μg/ml leupeptin, 50 μg/ml pepstatin, 10 mM TRIS-HCl pH=7.4), transferred to Eppendorf tubes and centrifuged (4° C.) for 10 min at 10,000 g. Supernatant was discarded, tubes inverted for 2–3 min., and then 50 to 75 μl of homogenization buffer were added. The pellet was finally sonicated for 10–20 sec (ultrasonic homogenizer, Cole-Parmer Instruments). The crude protein extract was stored at −80° C. for later analysis.

Protein assay, inmunoblotting, and total protein analyses procedures. Protein concentration was determined following an established dye-binding protein assay (R. D. Lane et al. *J. Immunol Methods* 92:261 (1986) for all homogenates. For immunoblots, a SDS-PAGE 4–20% gradient, 1.5 mM thick gel was used (Novex, San Diego, Calif.). Sample volume was adjusted to give a protein concentration of 1 μg/μl. Novex sample buffer (16 μl) was added to 16 μl of sample, the solution was heated to 85° C. for 2 min, loaded into the gel and subjected to 115 mV for ≈1.5 h. The Rainbow™ molecular weight standard (Amersham) was also loaded. The resolved proteins were electrophoretically transferred (51.2 mA for 2 h) to a unmodified 8 by 8 cm nitrocellulose paper (Pierce). Transfer buffers were as follows: anode, 40 mM E-aminoalkanoic acid, 25 mM TRIS, 20% methanol, pH=9.4; cathode, 25 mM TRIS, 20% methanol, pH=10.4, and 300 mM TRIS, 20% methanol, pH=10.4. The nitrocellulose paper was exposed overnight to SuperBlock™ (Pierce) and then incubated at room temperature for 1.5 h with a 10 ml solution containing the Cp20 monoclonal (as described in Materials and Methods, see Example 5) antibody (1:1000 dilution) and SuperBlock™. After rinsing 5 times with SuperBlock™, the nitrocellulose paper was incubated (1 h, room temperature) with 40 ml of protein A alkaline phosphatase conjugated (1:500 dilution, Cappel Organon Teknika) in SuperBlock™. After washes with SuperBlock™ (2 times), PBS (2 times), and 2 times with APS (100 mM TRIS, 100 mM NaCl, 5 mM $MgCl_2$, pH=9.4), the nitrocellulose paper was stained for about 7 to 10 min with a staining solution containing: 40 ml of APS, 3 mg NitroBlue™ Tetrazolium (Pierce), and 5 mg of 5-bromo-4-chloro-3-idolyl phosphate toluidine salt (Pierce). The staining reaction was stopped by rinsing with distilled water. Immunoblots were then digitized on a flat bed scanner and analyzed with imaging software written in the laboratory (TNImage by T. J. Nelson) for quantitative analysis. To correct for any difference in overall staining between gels, the integrated values of the band(s) of interest were normalized to the average background intensity of the blots. To study overall protein composition, an aliquot of each sample was analyzed by SDS-gel electrophoresis and the gel was exposed to the staining solution (0.1% Coomassie Blue R-250, 40% methyl alcohol, 10% acetic acid) for 20 min, and slowly destined (7.5% acetic acid, 15% methyl alcohol) for about 24 h. MW was determined by comparison with Mark12™ standards (Novex). Quantitative analysis of the gel was conducted with similar methods to those used for analyzing the immunoblots. Measurements of the regions of interest were normalized to the total densitometric area per lane.).

Monoclonal antibodies. Cp20 was purified from 20 squid optic lobes as described in the Methods and Materials in Example 5. Briefly, the purified protein was injected into mouse spleen and the spleen lymphocytes were fused with mouse myeloma cells X63-AG8-653 as described in Example 5. Hybridoma cells were selected by ELISA using plates coated with optic lobe extract as described in Example 5. The hybridoma was cloned by limiting dilution and cultivated in serum free media. The IgM fraction was purified by precipitation with $(NH_4)_2SO_4$ and dialyzed against PBS.

Figure 14A:
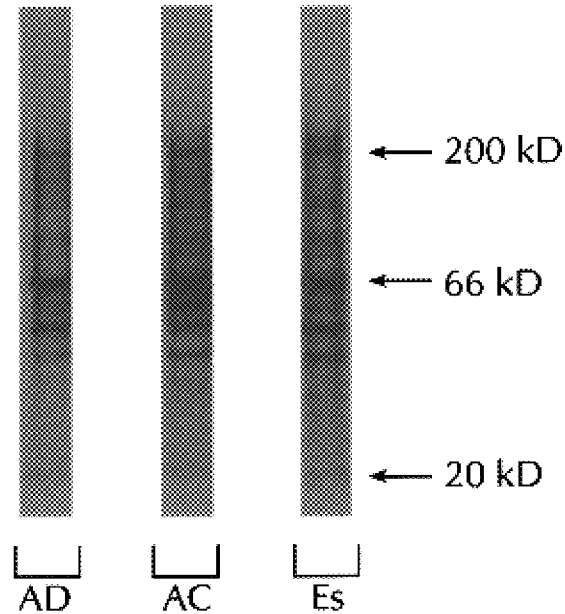
Figure 13A:
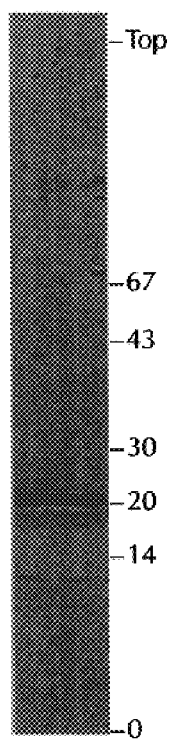
FIGS. 13A–13D. Western blot analyses of Cp20. (13A) Western blot of monoclonal anti-Cp20 reaction with cp20 purified from squid optic lobe (stain: HRP/ diaminobenzidine). (13B) Representative Western blots showing the stained protein band corresponding to Cp20 (index line). Visual inspection indicates a Cp20 reduction in AD (Alzheimer's disease fibroblast) and Es (Escapees, close relatives of Alzheimer's disease patients without symptoms) relative to fibroblasts from aged matched controls (AC). (13C) Graphic representation of quantitative analysis of each cell line shows clearly significant differences, with no overlap, between controls (Δ) as compared to AD (●) and Es (□), p<0.001 (ANOVA, Bonferroni post test). No significant differences were found between AD and Es fibroblasts. (13D) Bar graph representing the group data, further illustrating the significant Cp20 differences between control fibroblasts as compared to AD and Es cell lines.
Figure 13B:
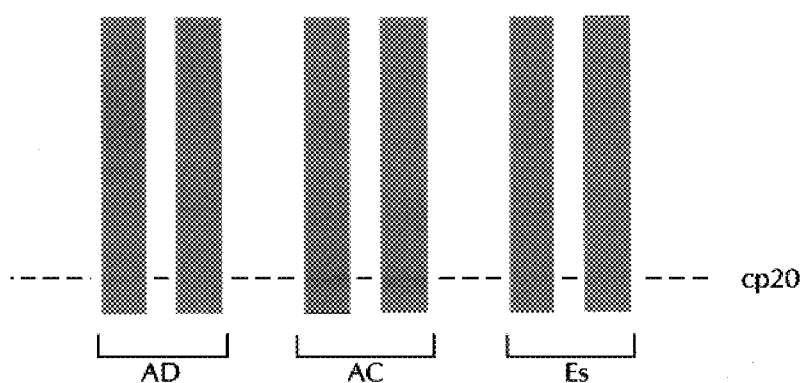
Figure 13C:
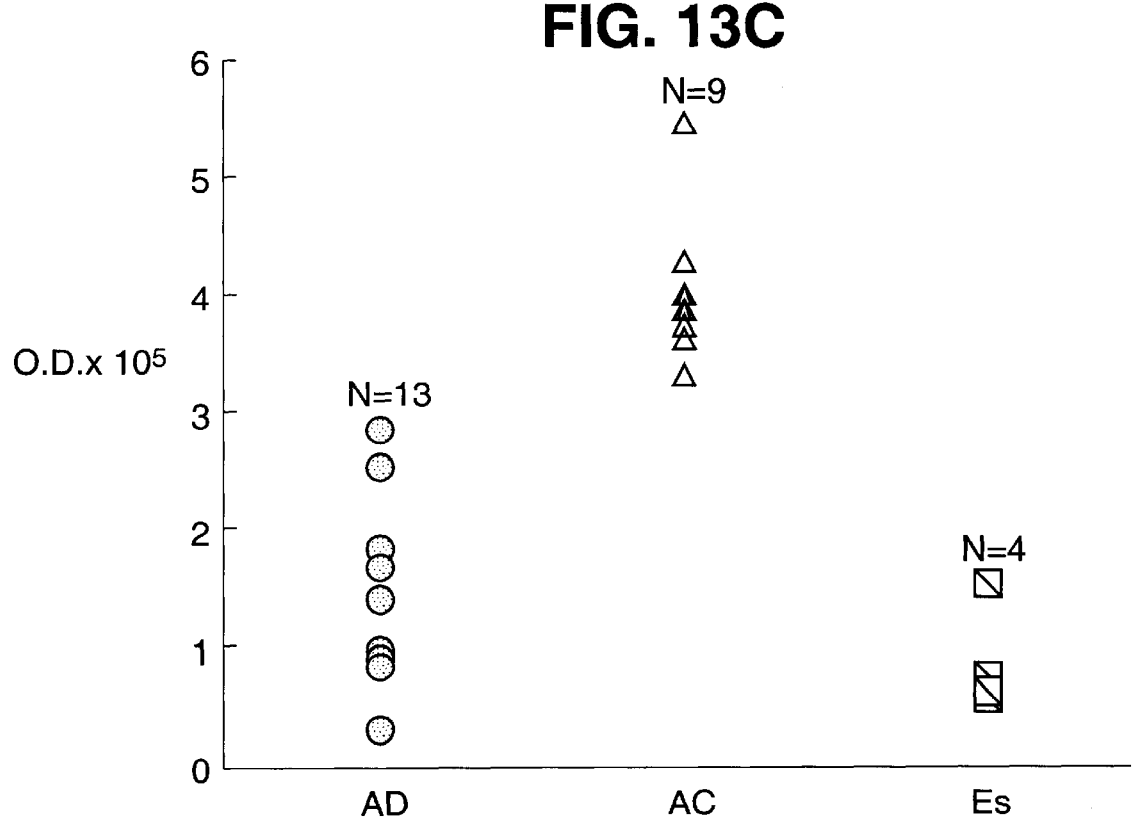
Figure 13D:
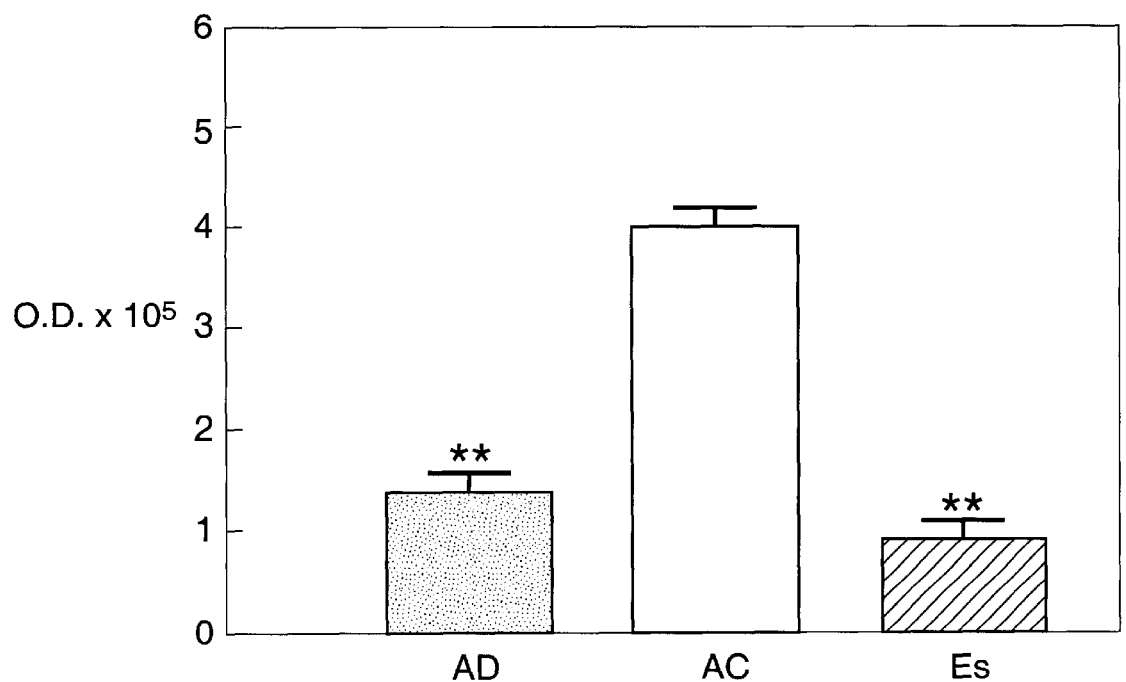

The antibody was previously shown to specifically recognize Cp20 in several species, including Hermissenda, rabbit, rat, sea urchin, and squid, as well as HPLC purified Squid Cp20 (see Example 5, and FIG. 13A) Fibroblasts from AD patients and age-matched (AC) controls were obtained from the Coriell Cell Repositories (Camden, N.J.) and cultured as described in the Methods and Materials. Cp20 was assessed by using the Cp20 monoclonal antibody.(See Methods and Materials Examples 5 and 6) and standard immunoblotting (Western) techniques. A distinct dark band was observed in the 20 kD region of immunoblots of all 9 AC cell lines, while it was almost absent or greatly reduced in all 13 familial and non-familial AD cell lines (FIGS. 13B and 13C). The 20 kD band was also reduced or absent in immunoblots from four clinically normal ("escapees", Es) individuals, who were close relatives of patients with familial Alzheimer's disease (T. D. Bird, *Alzheimer Disease* (Raven, N.Y., 1994; R. D. Terry, R. Katzman, K. L. Bick eds.) pp. 65–74.). Quantitative analysis of the immunoblots (FIGS. 13C–13D) confirmed that Cp20 levels were significantly higher in the controls as compared to AD and Es cell lines, $p<0.001$ (ANOVA, Bonferroni post test). No significant differences were found between AD and escapee's cell lines. In order to rule out a generalized effect on all proteins of ≈20 kD, a total protein analysis was conducted on SDS-PAGE Coomassie blue stained gels. Visual inspection (FIG. 14A) of the 20 kD molecular weight (MW) region, confirmed by quantitative analysis (FIG. 14B), showed no between-group differences, $p>0.05$, n.s. (ANOVA, Bonferroni post-test; instal version 1.15, Graphpad software, San Diego, Calif.). Analysis of the 66 to 33 kD MW region also revealed no between-groups differences, $p>0.05$, n.s. (ANOVA, Bonferroni post-test). Two additional protein bands in the high MW region (≈200 kD) also showed no significant differences between experimental groups, $p>0.05$, n.s. (ANOVA, Bonferroni post-test).

Figure 15A:
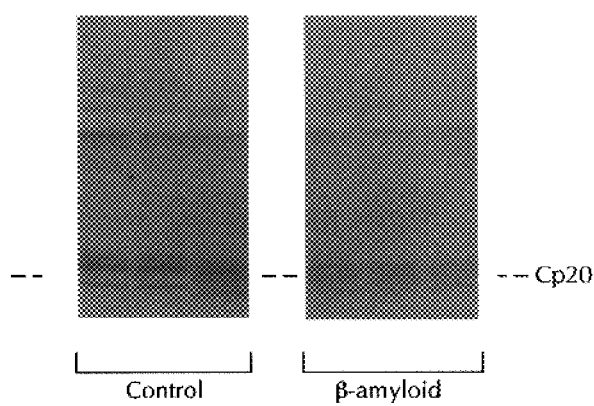
FIGS. 15A–15D. β-amyloid induces a reduction of Cp20 in control fibroblasts. (15A) Western blots of AC fibroblasts treated with β-amyloid for 48 h (right) and the same untreated cell lines (left). A reduction of Cp20 (index line) can be clearly observed in the β-amyloid treated cells as compared to the untreated counterparts. (15B) Bar graphs represent the quantitative analysis showing significant differences (p<0.003, Wilcoxon) between β-amyloid-treated and non-treated cells. (15C) Total protein profiles (Coomassie blue) revealed no differences between treated and non-treated cell lines. (15D) Quantitative analysis of protein bands around 20 kD (Cp20 M.W.) confirmed that β-amyloid did not cause general decrease of 20 kD MW region proteins (bar graph). Analysis of other bands (see Example 6) also showed no β-amyloid effects.
Figure 15C:
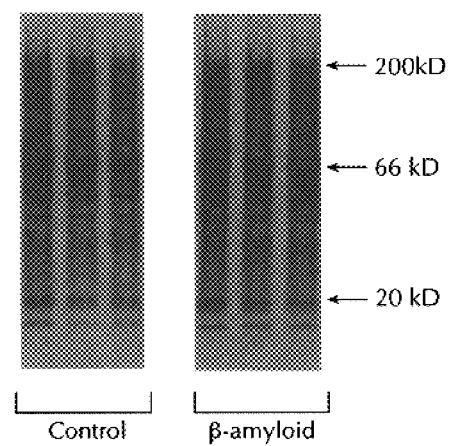
Figure 15B:
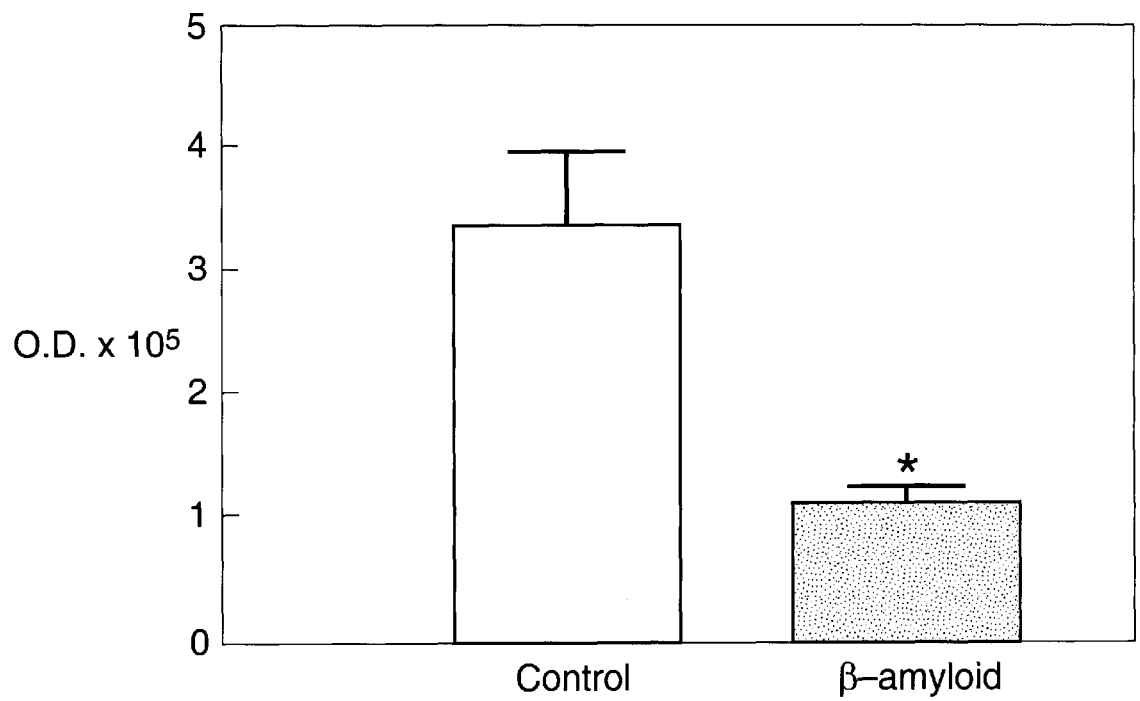
Figure 15D:
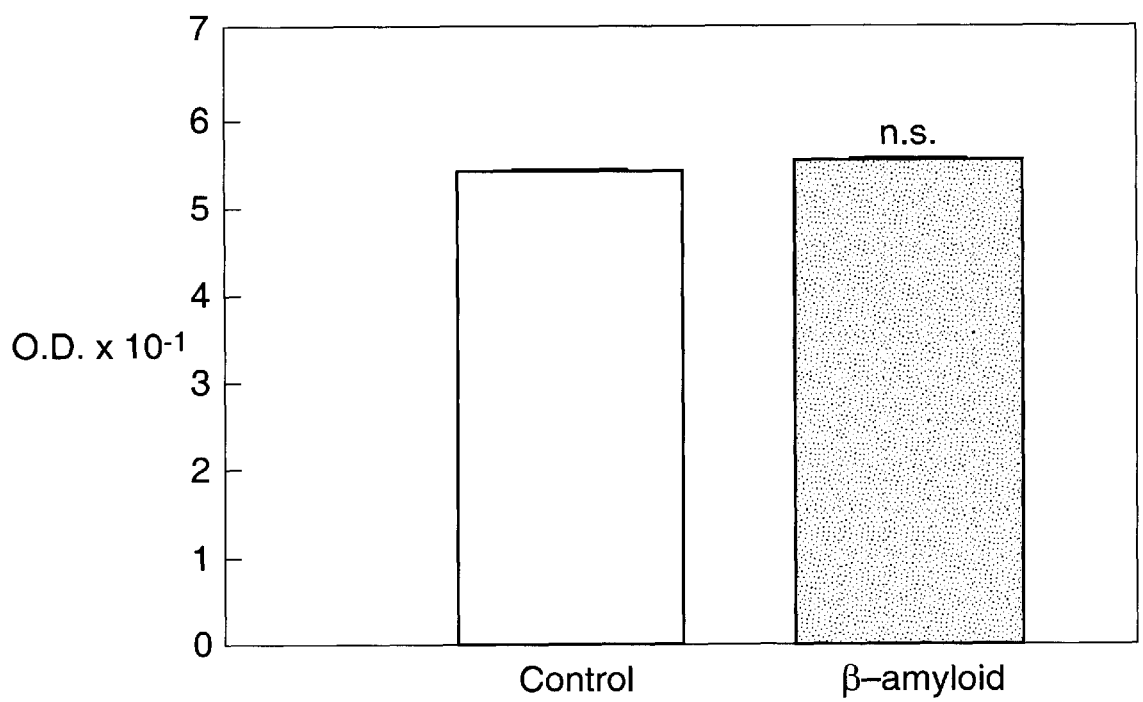

Since previous observations indicated that treatment with low concentrations of β-amyloid induces an AD-like $K^+$ dysfunction in control cells (R. Etcheberrigaray, E. Ito, C. S. Kim, D. L. Alkon, *Science* 264, 276 (1994).), we treated 9 AC cell lines with 10 nM β-amyloid for 48 h. Following the same immunoblotting procedure and analysis we found that Cp20 was significantly reduced in β-amyloid treated cells as compared to their non-treated counterparts, $p<0.003$ (Wilcoxon) (FIGS. 15A–15B). Total protein analysis revealed that the β-amyloid treatment was not a generalized effect on all proteins in the 20 kD region (15C–15D), $p>0.1$ (Wilcoxon). In addition, no between-group differences were observed in the 66–33 and 200 kD regions.

These results clearly demonstrate that Cp20, a memory-associated protein that induces a number of molecular and cellular changes that have been observed during memory acquisition and storage (T. J. Nelson, C. Collin, D. L. Alkon, *Science* 247, 1479 (1990); T. J. Nelson and D. L. Alkon, *Proc. Natl. Acad. Sci.* USA 85, 7800 (1988); ibid 87, 269 (1990); D. L. Alkon et al. *Proc. Natl. Acad. Sci. USA* 87, 1611 (1990); S. Moshiach, T. J. Nelson; J. V. Sanchez-Andres, M. Sakakibara, D. L. Alkon, *Brain Research* 605, 298 (1993); Example 5), is markedly reduced in fibroblasts from Alzheimer's patients. This is a new, specific extension of our previous findings (see Examples 1–4; R. Etcheberrigaray et al., *Proc. Natl. Acad. Sci.* (USA) 90, 8209 (1993); E. Ito et al., *Proc. Natl. Acad. Sci.* (USA) 91, 534 (1994) that have shown that other cellular steps ($K^+$ channel regulation, $Ca^{2+}$ release) in memory storage are altered in Alzheimer's disease. Since Cp20 is an extremely potent regulator of $K^+$ channels (T. J. Nelson, C. Collin, D. L. Alkon, *Science* 247, 1479 (1990).), its absence or reduction in AD could have some relationship to the previously observed differences of K$^+$ channels for AD fibroblasts (R. Etcheberrigaray et al., *Proc. Natl. Acad. Sci.* (USA) 90, 8209 (1993); R. Etcheberrigaray, E. Ito, C. S. Kim., D. L. Alkon, *Science* 264, 276 (1994).) and olfactory neuroblasts (data not shown)). The previously demonstrated regulation by Cp20 of retrograde axonal transport, as well as its sequential homology with the ARF protein Sarlp (involved in vesicle trafficking; see Example 5) suggest that its absence could also influence the predisposition to and/or development of the proteinaceous plaques and neurofibrillary tangles that characterize Alzheimer's Disease pathology in the human brain. These pathological processes, like Cp20, directly or indirectly involve vesicle trafficking (S. Estus et al. *Science* 255, 726 (1992); T. E. Golde, S. Estus, L. H. Younkin, D. L. Selkoe, S. G. Younkin, ibid., 728 (1992); C. Haass, E. H. Koo, A. Mellon, A. Y. Hung, D. J. Selkoe, *Nature* 357, 500 (1992); J. Busciglio, D. H. Gabuzda, P. Matsudaira, B. A. Yankner *Proc. Natl. Acad. Sci.* (USA) 90, 2092 (1993); N. K. Robakis, *Alzheimer Disease* (Raven, N.Y., 1994; R. D. Terry, R. Katzman, K. L. Bick eds.) pp. 317–326.) and, possibly, alterations of microtubule-associated proteins (K. A. Crutcher, B. H. Anderton, S. W. Barger, T. G. Ohm, A. D. Snow., *Hippocampug* 3, 271 (1993). K. S. Kosik and S. M. Greenberg, *Alzheimer Disease* (Raven, N.Y., 1994; R. D. Terry, R. Katzman, K. L. Bick eds.) pp. 335–344). Phosphorylation of tau (a potentially pathological event) by mitogen-activated protein (MAP) kinase, can be promoted by APP (amyloid precursor protein, the protein from which β-amyloid originates) and prevented by inhibition of ras proteins (K. S. Kosik and S. M. Greenberg, *Alzheimer Disease* [Raven, N.Y., 1994; R. D. Terry, R. Katzman, K. L. Bick eds.] pp. 335–344; S. M. Greenberg, E. H. Koo, W. Q. Qiu, A. W. Sandrock, K. S. Kosik, *Soc. Neurosci. Abs.*, 19, 1276(1994); K. S. Kosik, *JAMA* 271, 89 (1994) [in Medical News & Perspectives by P. Cotton]). The ras involvement in this process is intriguing, since ras and Cp20 share functional properties (C. Collin, A. G. Papagorge, D. L. Lowy, D. L Alkon, *Science* 250, 1743 (1990)] and also some degree of homology (see Example 5). Moreover, one of the suggested normal functions for tau is to participate in microtubule elongation and shaping axonal morphology (K. S. Kosik, *Brain Pathology* 3, 39 (1993)), which may be related to dendritic changes induced by Cp20 during memory acquisition (S. Moshiach, T. J. Nelson, J. V. Sanchez-Andres, M. Sakakibara, D. L. Alkon, *Brain Research* 605, 298 (1993).). It is also interesting that G$_o$, a heterotrimeric GTP-binding protein involved in membrane trafficking and axonal transport (M. Bomsel, K. Mostov, *Molec. Biol. Cell* 3, 1317 (1992)), associates with the cytoplasmic domain of APP (Nishimoto, I. et al, *Nature* 362 (1993).). Thus, Cp20 alterations, perhaps linked to β-amyloid metabolism and tau phosphorylation, could affect normal axonal transport and intracellular vesicle trafficking, contributing to Alzheimer's Disease pathology. Since Cp20 was also reduced in Es (i.e. close relatives of individuals with familial Alzheimer's Disease), the observed loss of Cp20 could diagnostically mark Alzheimer's Disease as well as genetic predisposition to Alzheimer's Disease even in the absence of clear clinical symptoms of Alzheimer's disease.

EXAMPLE 7
Diagnostic Index for Alzheimer's Disease

Materials and Methods

Cell Culture Procedures. Cultured fibroblasts were obtained from the Coriell Cell Repositories (Camden, N.J.) and from the Laboratory of Molecular and Cellular Neurobiology, Sacred Heart Hospital of Brescia (Brescia, Italy). Cell lines include AD, age-matched controls, controls suffering from other non-AD neurological and psychiatric conditions, and three cell lines from clinically unaffected members (Es, escapees) of the Canadian AD family 964 (Nee, L. E.; *Arch. Neurol.* 40:203–208; 1983). The Italian cell lines (designated by I in Table 7) are from living patients, the fibroblast preparation as well as diagnostic procedures are previously described (Govoni, S. et al; *Neurology* 43:2581–2586 (1993)). Additional information about the Coriell cell lines can be obtained elsewhere (National Institute of Aging, 1991 Catalog of Cell Lines. 1991; National Institute of General Medical Sciences, 1990/1991 Catalog of Cell Lines (NIH Publication 91-2011, 1990)). Cells were seeded as previously described) (Examples 1–4; Etcheberrigaray, R.; et al., *Proc. Natl. Acad. Sci.* USA 90:8209–8213; 1993) in 35 mm Nunc petri dishes, and used three to four days after seeding, at comparable levels of confluence (≈60 to 80 cells per mm$^2$).

Calcium Imaging. Culture medium was removed and cells were washed at least three times with BSS (in mM: NaCl 140, KCl 5, CaCl$_2$ 2.5, MgCl$_2$ 1.5, HEPES 10, Glucose 5, pH=7.4). The fluorescent probe was loaded by incubating the cells in 2 μM (in BSS) fura 2-AM (Molecular Probes) for 60 min at room temperature. After loading, cells were washed thoroughly with BSS or BSS-0 Ca$^{2+}$ (in mM: NaCl 140, KCl 5, CaCl$_2$ 0.1, MgCl$_2$ 1.5, EGTA 1, HEPES 10, Glucose 5, pH=7.4). After washes, 1 ml of fresh solution was added for intracellular Ca$^{2+}$ baseline measurements. TEA (Sigma) challenge was performed by adding to the dish 3 ml of TEA-modified BSS (TEA-MBSS) solution (in mM: TEA 133.3, NaCl 6.7, KCl 5, CaCl$_2$ 2.5, MgCl$_2$ 1.5, HEPES 10, Glucose 5, pH=7.4). This solution was adjusted in order to introduce no osmolality changes. Bombesin stimulation was accomplished by adding 1 ml of BSS plus bombesin to achieve final bombesin (Calbiochem) concentrations of 1 μM and 100 nM, with and without external Ca$^{2+}$. Bradykinin (Calbiochem) in BSS and BSS-0 Ca$^{2+}$ (1 ml) was also used at concentrations of 100 pM, 1 nM and 10 nM. Fluorescent images at 340 and 380 nm were acquired at a rate of 2.6/sec. for 200 sec, with a Hamamatsu Argus 50 system (Hamamatsu Photonics). The objective lens was a 10× Nikon fluor. Only the 1/4 evenly illuminated area of the whole image was acquired. Individual ratio values were obtained off-line for all cells within the area of interest. Three to five dishes of a given cell line were used for each experimental condition. The number of cells measured per cell line was at least 50. In most cases, experiments for each cell line were repeated on at least one separate occasion (minimum one week interval).

Figure 16A:
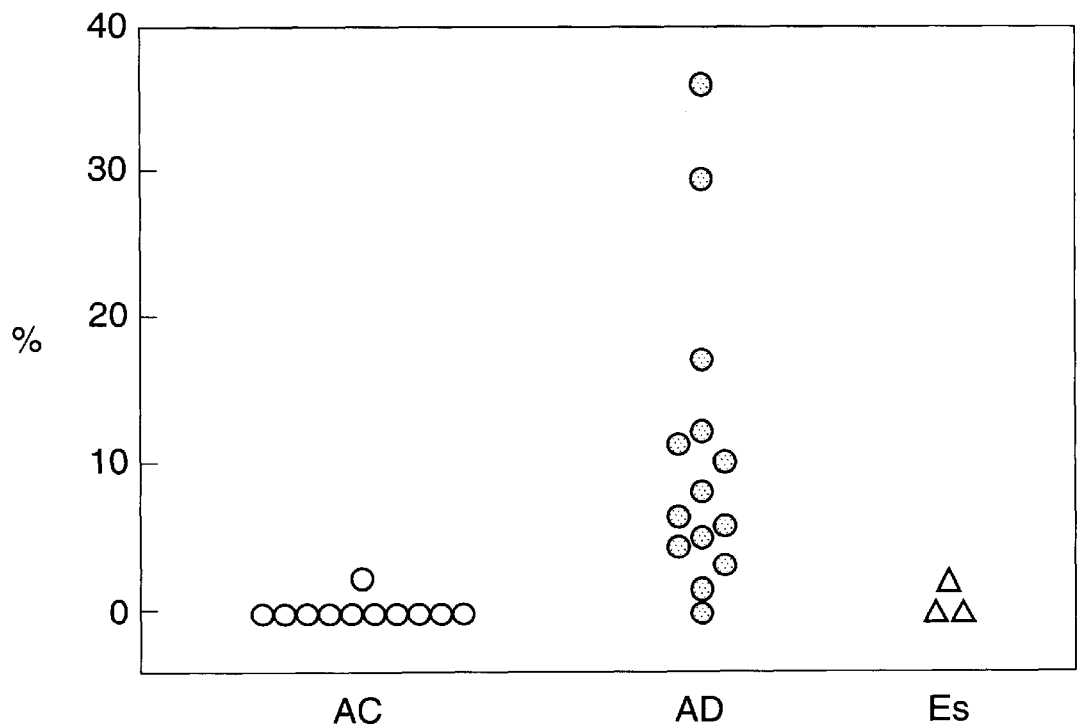
FIG. 16A–16C. Bradykinin-induced responses. Calcium elevations in response to 100 pM bradykinin were almost exclusively observed in AD cell lines. The graph represents each cell line tested (16A). The degree of responsiveness is expressed as % of cells responding to the challenge (no differences in the peak or integrated area were observed among responding cells). All but one (I4) AD cell lines responded, and the vast majority had higher % of responding cells than the one control (AG07141) that exhibited a response. Cell lines from Es have responses comparable to the control group. The highly significant group differences are shown in the bar graph (16B). A representative trace of the response is depicted in 16C. Solid lines are cell from the Coriell Cell Repositories. Broken lines are cell of Italian origin. The arrow indicates drug application.
Figure 16B:
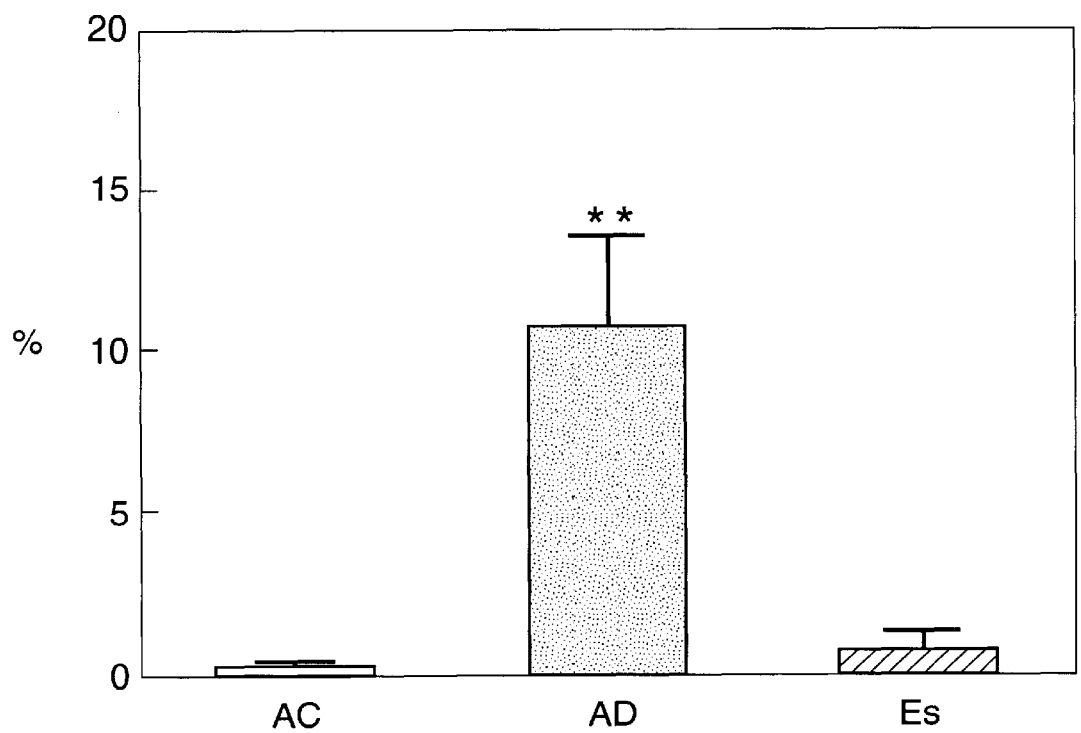
Figure 16C:
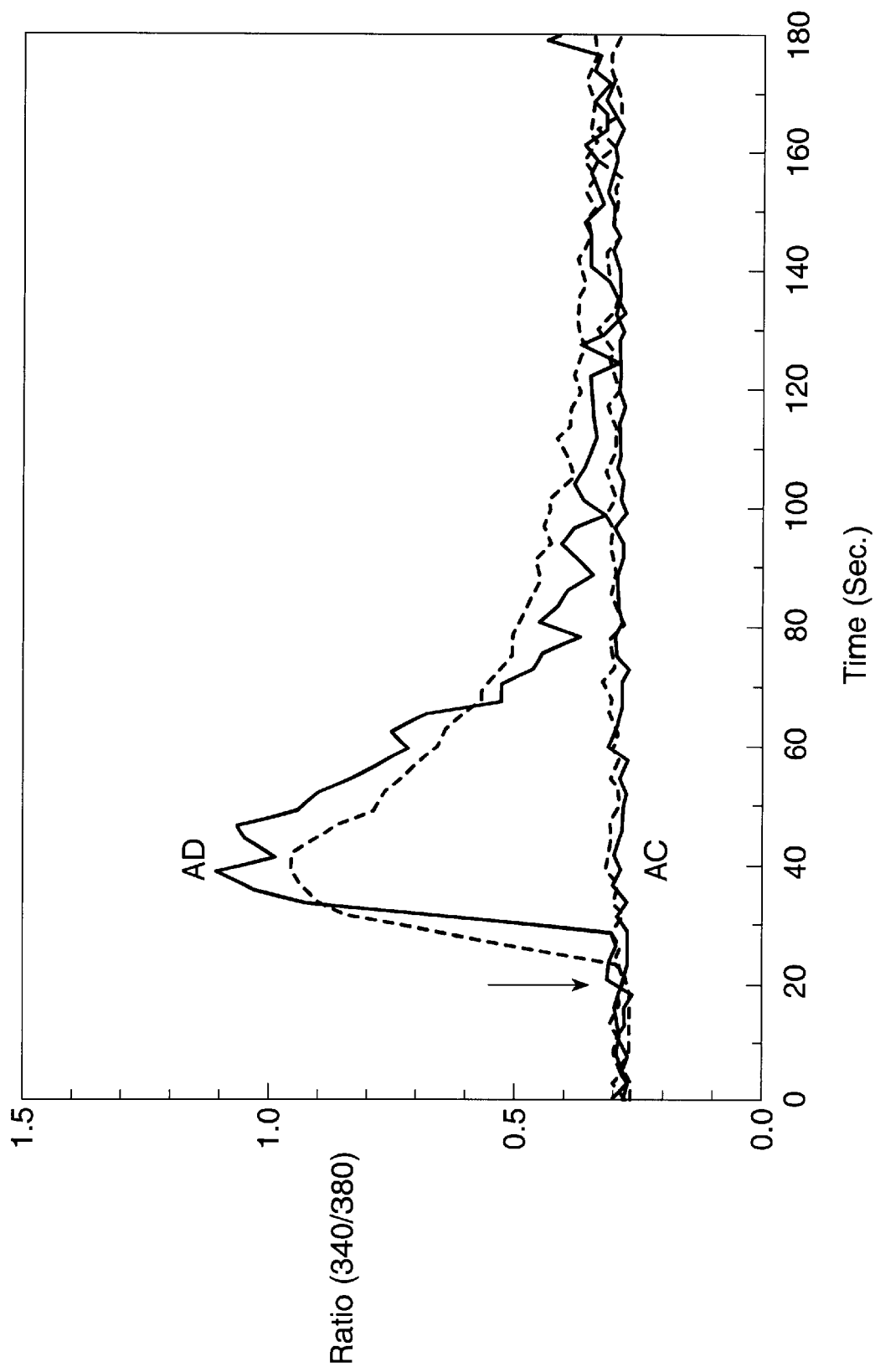

Bradykinin Induced Responses.—Bradykinin-induced release was tested in the present study as measure of IP$_3$-mediated functions. Bath application of 100 pM bradykinin elicited virtually no responses from control cells (N=11 cell lines). Only one cell line (AG07141) exhibited some noticeable responses, that did not reach "criterion" levels (CR, see below). In contrast, 13 out of 14 AD cell lines had clear responses and only one (I4) failed to meet criterion levels. Statistical analysis of percentages of responding cells revealed highly significant differences between AD and controls, p<0.0003 (Mann-Whitney). The difference between the two groups analyzed by contingency table (response/non-response, based on CR) was also highly significant, p<0.0005 (Fisher's exact test). Cell lines from Es showed responses similar to those of control cell lines, p=0.3 (Mann-Whitney, not significant). FIG. 16A illustrates the distribution of bradykinin responses, expressed as % of responding cells. Control and Es cell lines clearly cluster at or near "0% responding cells", while AD cell lines show a wider and higher distribution. FIG. 16B shows the group data differences and 16C illustrates the time course of a typical bradykinin induced response. A comparison between the Coriell and Italian (designated "I") samples showed no differences in terms of responsiveness/unresponsiveness, p=0.23, N.S. (Fisher's exact test). Higher bradykinin concentration ($\geq 1$ nM), elicited responses of similar magnitude, and in comparable number of responding cells in AD and controls, thus obscuring the differences in bradykinin sensitivity between groups.

Bombesin Induced Responses.—As previously reported (Examples 1–4; Ito, E. et al., *Proc. Natl. Acad. Sci.* USA 91:534–538; 1994) addition of 1 $\mu$M bombesin elicited responses in all cell lines, even in the absence of external $Ca^{2+}$. The % of cells responding had a tendency to be greater in AD cell lines but did not reach statistical significance (p=0.08, Mann-Whitney). Following the CR for bombesin listed below, the magnitude of the responses, however, (measured as the integrated area from under the curve for all cells, from the onset to the end of the response) was significantly higher in AD cell lines (26956±4494.7, Mean±SEM) cell lines as compared to controls (5402.3±3606.4), p<0.004 (Mann-Whitney). Using the same CR, a contingency table analysis also shows significant differences between the two groups; all but 3 AD cell lines (N=14 total) had responses, while only 2 out of 10 control cell lines had responses, p<0.007 (Fisher's exact test). Moreover, taking into account all responses, without considering the CR, the magnitude of the responses was still significantly higher in AD cell lines as compared to controls, p<0.005 (Mann-Whitney). As for bradykinin, the magnitude of the bombesin responses was similar for the Italian and Coriell cell lines, p=0.79, N.S. (Mann-Whitney).

Figure 17A:
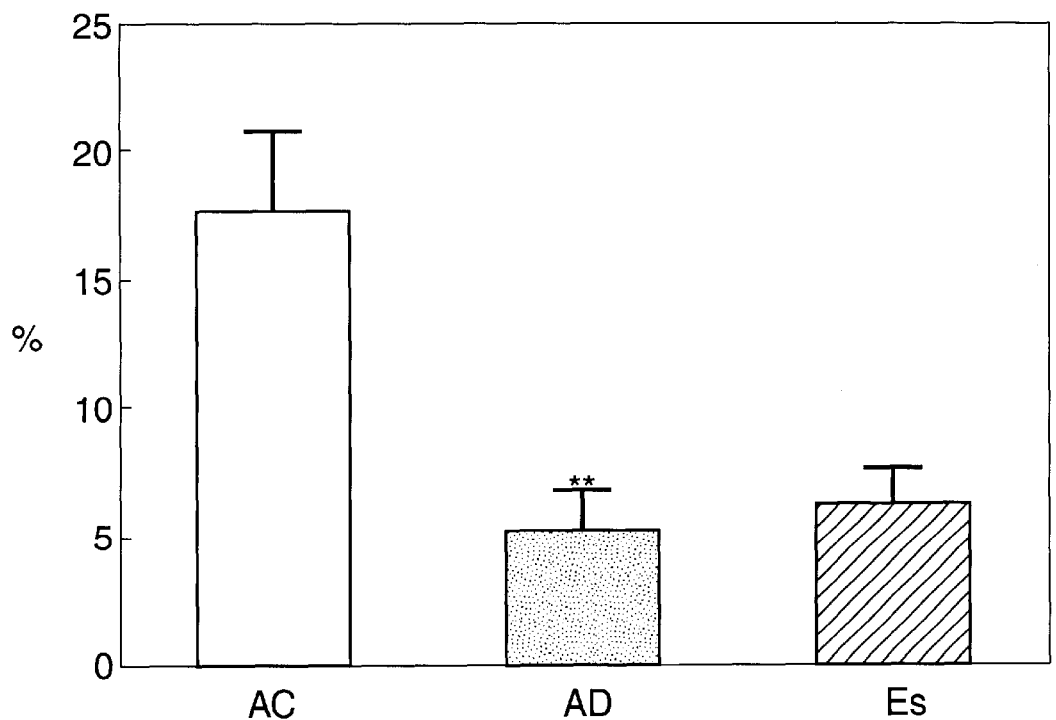
FIGS. 17A–17B. TEA-induced responses. Bars represent the average % of responding cells in each group. The % of responding cells in AD cell lines was significantly reduced as compared to controls, p<0.001. Es from the canadian AD family showed, on average, a % of responding cells similar to AD cell lines, and significantly lower than controls (17A). A typical TEA-induced response is illustrated in (17B). Dotted and solid lines represent cells' origin as in FIGS. 16A–16C.
Figure 17B:
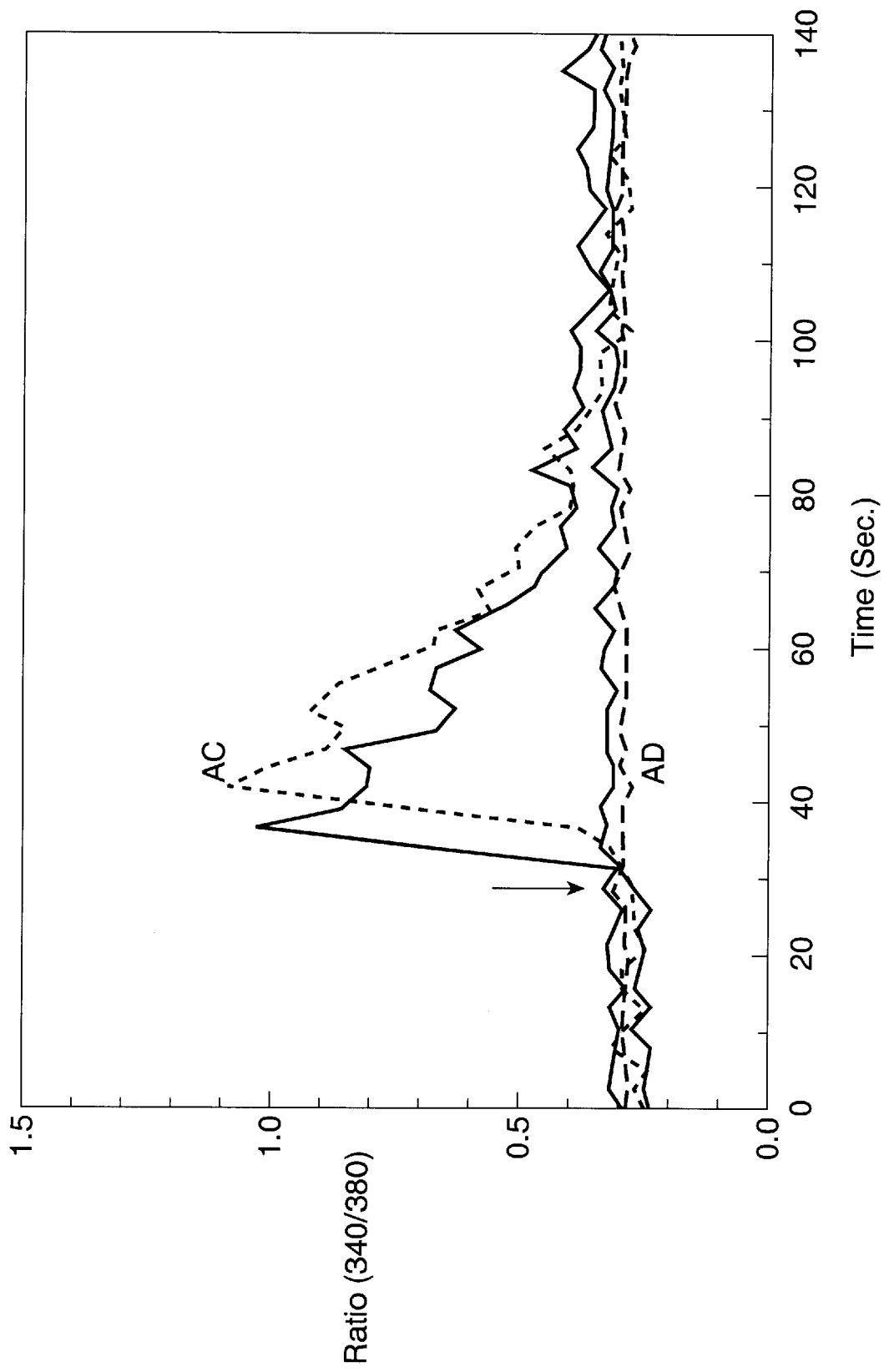

TEA Induced Responses.—TEA stimulation (100 mM) resulted in $Ca^{2+}$ elevations in control cell lines as expected (See Examples 1–4). All 11 control cell lines exhibited significant $Ca^{2+}$ elevations, meeting "CR" (see below). As expected, the majority of the AD cell lines (10 out of 14) did not meet CR. The remaining 4 cell lines with responses on average still had a lower % of cells responding. Overall, there was a highly significant difference between % of cells responding in AD as compared to all control cell lines, p<0.0005 (Mann-Whitney). Contingency table analysis (response/no-response) also revealed a clear and significant difference, p<0.0004 (Fisher's exact test). The 3 Es cell lines had lower % of responding cells (one did not meet CR), and on average they had values closer to AD than control cell lines. The bar graph in FIG. 17A illustrates these results. A representative trace of the TEA induced response is depicted in FIG. 17B. Latency to the onset and magnitude of the responses were comparable within control lines as well as with the 4 AD cell lines with responses. The control cell lines used in AG06241, AG04260 and AG07141 showed virtually identical responses in the present study. Lack of responsiveness was found in AD cell lines AG06844, AG06848, AG07375, AG07377, and AG08170 used in both the past and present study. A comparison of the TEA responses from the originally tested control cell lines (Examples 1–4; Etcheberrigaray, R. et al., *Proc. Natl. Acad. Sci. USA* 90:8209–8213; 1993) and those obtained from the present control group, revealed no significant differences between the two control groups, p=0.38 (Fisher's exact test). Similarly, the lack of responsiveness of the previously tested AD group did not significantly differ from the AD cell lines used in this study. Moreover, an overall comparison of TEA responses/lack of responses between the present and original sample showed no differences, p=0.55 (Fisher's exact test). In addition, no differences (response/no-response where observed between the Coriell and Italian samples, p=0.24, N.S. (Fisher's exact test).

Integrated Index for Alzheimer's Disease.—Each individual molecular alteration described in AD cells has a high degree of specificity and sensitivity, and correctly identifies and separates AD cases from controls. For diagnostic purposes, it is desirable to maximize specificity and sensitivity. Therefore, a combined scoring system taking into account all observable altered and normal responses in fibroblasts from AD and control cells respectively was devised. The combined score generates a numerical index whose negative values indicate the pathological response for each challenge. Positive values indicate the opposite. A combined index value <0 indicates AD, values $\geq 0.5$ would identify normal or non-AD conditions. Criterion responses defined based on the responses of all cell lines examined and scoring criteria for each challenge is as follows:

| Treatment | Response | Score |
|---|---|---|
| Bradykinin (0.1 nm) | <1.5% responding cells | 0 (no response) |
| (Latency of the onset $\leq$135 sec) | $\geq$1.5% responding cells | −0.5 |
|  | $\geq$4.0% responding cells | −1.0 |
| TEA (100 mM) | <5% responding cells | 0 (no response) |
| (Latency of the onset $\leq$60 sec) | $\geq$5% responding cells | 0.5 |
|  | $\geq$16% responding cells | 1.0 |
| Bombesin* (1 $\mu$m) | <50% responding cells or area <23000 nM-sec | 0 (no response) |
| (Latency of the onset $\leq$40 sec) | $\geq$50% responding cells and area $\geq$23000 nM-sec | −0.5 |
|  | $\geq$50% responding cells and area $\geq$30000 nM-sec | −1.0 |

*Calcium free medium

The results clearly indicated that taking into account the overall profile of responses increase the diagnostic value of these cellular alterations. The index allows the detection of all control and AD cases without a single overlap. Even though some AD cell lines do not express all AD "molecular phenotypes", in combination they express sufficient alterations to be correctly identified by the index system. Thus, this method of considering three or more diagnostic parameters adds specificity and sensitivity.

Bombesin induced responses were higher in AD fibroblasts as expected. (See Examples 1–4) The bombesin and bradykinin results are consistent since both agents induce $IP_3$ generation. Responses induced by 100 pM bradykinin turned out to have an even higher degree of specificity for identifying AD cells than TEA or bombesin-induced responses.

TABLE 7

| Line # | Bradykinin | TEA | Bombesin | Index |
|---|---|---|---|---|
| Alzheimer's |  |  |  |  |
| AG06848 | −1 | 0 | −1 | −2 |
| AG08170 | −1 | 0 | −0.5 | −1.5 |
| AG06844 | −1 | 0 | −1 | −2 |
| AG08527 | −1 | 0 | −0.5 | −1.5 |
| AG07375 | −1 | 0 | −0.5 | −1.5 |

TABLE 7-continued

| Line # | Bradykinin | TEA | Bombesin | Index |
|---|---|---|---|---|
| AG07377 | −1 | 0 | −1.0 | −2.0 |
| AG06262 | −1 | 0.5 | −0.5 | −1 |
| I4 | 0 | 0.5 | −1 | −0.5 |
| I6 | −1 | 0 | 0 | −1 |
| I8 | −0.5 | 0 | −0.5 | −1 |
| I24 | −0.5 | 1 | −1 | −0.5 |
| I41 | −1 | 0 | 0 | −1 |
| I43 | −1 | 0 | −1 | −2 |
| I46 | −1 | 0.5 | 0 | −0.5 |
| Controls | | | | |
| AG06241 | 0 | 1 | N.T. | 1 |
| GM04260 | 0 | 1 | −0.5 | 0.5 |
| AG07141 | −0.5 | 1 | 0 | 0.5 |
| AG05266 | 0 | 0.5 | 0 | 0.5 |
| I26 | 0 | 1 | 0 | 1 |
| I29 | 0 | 1 | 0 | 1 |
| I39 | 0 | 1 | 0 | 1 |
| I2 | 0 | 0.5 | 0 | 0.5 |
| I9 | 0 | 1 | 0 | 1 |
| I13 | 0 | 0.5 | −0.5 | 0 |
| I37 | 0 | 0.5 | 0 | 0.5 |

Figure 18:
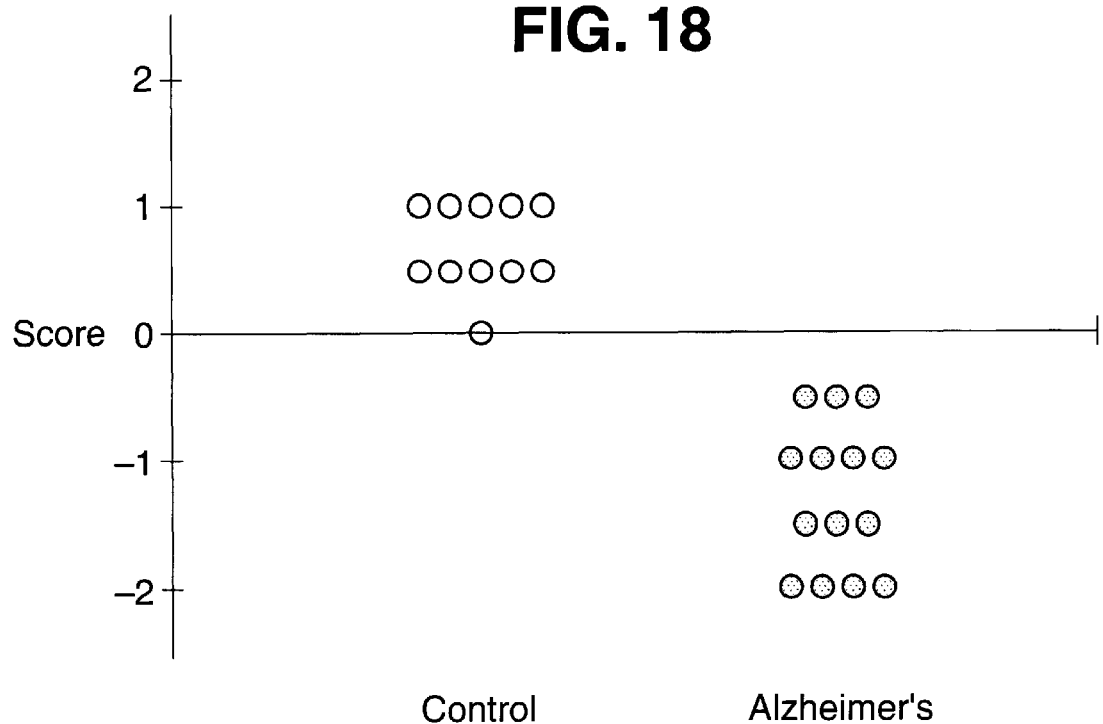
FIG. 18. Index for AD. Dots represent the combined score value for each particular cell line. As can be clearly observed from the figure, controls (open symbols) have significantly higher values than AD cell lines (solid symbols), p<0.001. The two groups also segregate without overlap.

Table 7 shows the scores and final index for each cell line analyzed with this method. It is clear that control cell lines have positive scores, while AD cell have negative scores. Only one of the control lines had a score of 0, which is still greater than all AD cell lines. Statistical analyses of the index revealed a highly significant difference between AD and controls, $p<0.0001$ (Mann-Whitney). FIG. 18 depicts the distribution of the scores of controls and AD cell lines. In the AD scoring system, a numeric value is assigned (see text) according to the response for each cell line. The sum of the scores generates a final index value. This index value distinguishes AD from all controls. Both the sensitivity and specificity of the index for this sample are 100%

The invention has been described in detail with particular reference to the preferred embodiments thereof, but it will be understood that the invention is capable of other and different embodiments. As is readily apparent to those skilled in the art, variations and modifications can be affected within the spirit and scope of the invention. Accordingly, the foregoing disclosure and description are for illustrative purposes only, and do not in any way limit the invention, which is defined only by the claims.

What is claimed is:

1. A method for assaying a sample of viable cells from a patient for the presence of Alzheimer's disease, said method comprising the steps of:
   i) assaying said sample with a bombesin Alzheimer's disease diagnostic test, wherein a score of 0 indicates the absence of Alzheimer's disease and a score of −0.5 or −1.0 indicates the presence of Alzheimer's disease;
   ii) assaying said sample with a bombesin Alzheimer's disease diagnostic test, wherein a score of 0 indicates the absence of Alzheimer's disease and a score of −0.5 or −1.0 indicates the presence of Alzheimer's disease; and
   iii) adding the scores obtained from said bradykinin and a bombesin Alzheimer's disease diagnostic tests, wherein a negative value indicates the presence of Alzheimer's disease and a positive value indicates the absence of Alzheimer's disease.

2. The method according to claim 1, wherein the bradykinin Alzheimer's disease diagnostic test comprises contacting the sample with bradykinin for a time period not more than 135 seconds, and measuring the percentage of cells responding with an increase in intracellular calcium ion concentration, wherein a score of zero is assigned when the percentage of responding cells is less than 1.5%, a score of −0.5 is assigned when the percentage of responding cells is greater than or equal to 1.5%, and a score of −1 is assigned when the percentage of cells responding is greater than or equal to 4%.

3. The method according to claim 1, wherein the bombesin Alzheimer's disease diagnostic test comprises contacting the sample with bombesin for a time period not more than 40 seconds, and measuring the percentage of cells responding with an increase in intracellular calcium ion concentration and the magnitude of response, the magnitude of response being represented by an area under a graph of calcium ion concentration as a function time, wherein a score of zero is assigned when the percentage of responding cells is less than 50% or the area <23000 nM-sec, a score of −0.5 is assigned when the percentage of responding cells is greater than or equal to 50% and an area greater than or equal to 2300 nM-sec, and a score of −1 is assigned when the percentage of cells responding is greater than or equal to 50% and an area greater than or equal to 30000 nM-sec.

4. A method for assaying a sample of viable cells from a patient for the presence of Alzheimer's disease, said method comprising the steps of:
   i) assaying said sample with a bradykinin Alzheimer's disease diagnostic test, wherein a score of 0 indicates the absence of Alzheimer's disease and a score of −0.5 or −1.0 indicates the presence of Alzheimer's disease;
   ii) assaying said sample with a TEA Alzheimer's disease diagnostic test, wherein a score of 0.5 or 1 indicates the absence of Alzheimer's disease and a score of 0 indicates the presence of Alzheimer's disease; and
   iii) adding the scores obtained from said bradykinin and TEA Alzheimer's disease diagnostic tests, wherein a negative value indicates the presence of Alzheimer's disease and a positive value indicates the absence of Alzheimer's disease.

5. The method according to claim 4, wherein the bradykinin Alzheimer's disease diagnostic test comprises contacting the sample with bradykinin for a time period not more than 135 seconds, and measuring the percentage of cells responding with an increase in intracellular calcium ion concentration, wherein a score of zero is assigned when the percentage of responding cells is less than 1.5%, a score of −0.5 is assigned when the percentage of responding cells is greater than or equal to 1.5%, and a score of −1 is assigned when the percentage of cells responding is greater than or equal to 4%.

6. The method according to claim 4, wherein the TEA Alzheimer's disease diagnostic test comprises contacting said sample with TEA for a time period not more than 60 seconds and measuring the percentage of cells responding with an increase in intracellular calcium ion concentration, wherein a score of zero is assigned when the percentage of responding cells is less than 5%, a score of 0.5 is assigned when the percentage of responding cells is greater than or equal to 5%, and a score of 1 when the percentage of cells responding is greater than or equal to 16%.

7. A method for assaying a sample of viable cells from a patient for the presence of Alzheimer's disease, said method comprising the steps of:

i) assaying said sample with a bombesin Alzheimer's disease diagnostic test, wherein a score of 0 indicates the absence of Alzheimer's disease and a score of −0.5 or −1.0 indicates the presence of Alzheimer's disease;

ii) assaying said sample with a TEA Alzheimer's disease diagnostic test, wherein a score of 0.5 or 1 indicates the absence of Alzheimer's disease and a score of 0 indicates the presence of Alzheimer's disease; and iii) adding the scores obtained from said bombesin and TEA Alzheimer's disease diagnostic tests, wherein a negative value indicates the presence of Alzheimer's disease and a positive value indicates the absence of Alzheimer's disease.

8. The method according to claim 7, wherein the bombesin Alzheimer's disease diagnostic test comprises contacting the sample with bombesin for a time period not more than 40 seconds, and measuring the percentage of cells responding with an increase in intracellular calcium ion concentration and the magnitude of response, the magnitude of response being represented by an area under a graph of calcium ion concentration as a function of time, wherein a score of zero is assigned when the percentage of responding cells is less than 50% or the area <23000 nM-sec, a score of −0.5 is assigned when the percentage of responding cells is greater than or equal to 50% and an area greater than or equal to 23000 nM-sec, and a score of −1 is assigned when the percentage of cells responding is greater than or equal to 50% and an area greater than or equal to 30000 nM-sec.

9. The method according to claim 7, wherein the TEA Alzheimer's disease diagnostic test comprises contacting said sample with TEA for a time period not more than 60 seconds and measuring the percentage of cells responding with an increase in intracellular calcium ion concentration, wherein a score of zero is assigned when the percentage of responding cells is less than 5%, a score of 0.5 is assigned when the percentage of responding cells is greater than or equal to 5%, and a score of 1 when the percentage of cells responding is greater than or equal to 16%.

10. A method for assaying a sample of viable cells from a patient for the presence of Alzheimer's disease, said method comprising the steps of:

i) assaying said sample with a bradykinin Alzheimer's disease diagnostic test, wherein a score of 0 indicates the absence of Alzheimer's disease and a score of −0.5 or −1.0 indicates the presence of Alzheimer's disease;

ii) assaying said sample with a bombesin Alzheimer's diagnostic test, wherein a score of 0 indicates the absence of Alzheimer's disease and a score of −0.5 or −1.0 indicates the presence of Alzheimer's disease; and iii) assaying said sample with a TEA Alzheimer's disease diagnostic test, wherein a score of 0.5 or 1 indicates the absence of Alzheimer's disease and a score of 0 indicates the presence of Alzhimer's disease; and iv) adding the scores obtained from said bradykinin, bombesin and TEA Alzheimer's disease diagnostic tests, wherein a negative value indicates the presence of Alzheimer's disease and a positive value indicates the absence of Alzheimer's disease.

11. The method according to claim 10, wherein the bradykinin Alzheimer's disease diagnostic test comprises contacting the sample with bradykinin for a time period not more than 135 seconds, and measuring the percentage of cells responding with an increase in intracellular calcium ion concentration, wherein a score of zero is assigned when the percentage of responding cells is less than 1.5%, a score of −0.5 is assigned when the percentage of responding cells is greater than or equal to 1.5%, and a score of −1 is assigned when the percentage of cells responding is greater than or equal to 4%.

12. The method according to claim 10, wherein the bombesin Alzheimer's disease diagnostic test comprises contacting the sample with bombesin for a time period not more than 40 seconds, and measuring the percentage of cells responding with an increase in intracellular calcium ion concentration and the magnitude of response, the magnitude of response being represented by an area under a graph of calcium ion concentration as a function of time, wherein a score of zero is assigned when the percentage of responding cells is less than 50% or the area <23000 nM-sec, a score of −0.5 is assigned when the percentage of responding cells is greater than or equal to 50% and an area greater than or equal to 23000 nM-sec, and a score of −1 is assigned when the percentage of cells responding is greater than or equal to 50% and an area greater than or equal to 30000 nM-sec.

13. The method according to claim 10, wherein the TEA Alzheimer's disease diagnostic test comprises contacting said sample with TEA for a time period not more than 60 seconds and measuring the percentage of cells responding with an increase in intracellular calcium ion concentration, wherein a score of zero is assigned when the percentage of responding cells is less than 5%, a score of 0.5 is assigned when the percentage of responding cells is greater than or equal to 5%, and a score of 1 when the percentage of cells responding is greater than or equal to 16%.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 46
      (B) TYPE: AMINO ACID
      (C) STRANDEDNESS: UNKNOWN
      (D) TOPOLOGY: UNKNOWN (xi) SEQUENCE DESCRIPTION: SEQ ID NO:1:

Ala Arg Leu Trp Thr Glu Tyr Phe Val Ile Ile Asp Ile
1               5                    10

Val Asn Leu Gly Tyr Asp Leu Asn Glu Thr Leu Ile Asn
    15               20                 25

Asp Leu Leu Leu Glu Asp Ile Lys Glu Ala Leu Leu Val
            30               35

Asp Val Asp Phe Val Asn Gln
40            45

(2) INFORMATION FOR SEQ ID NO:2:

(i) SEQUENCE CHARACTERISTICS:
      (A) LENGTH: 46
      (B) TYPE: AMINO ACID
      (C) STRANDEDNESS: UNKNOWN
      (D) TOPOLOGY: UNKNOWN (xi) SEQUENCE DESCRIPTION: SEQ ID NO:2:

Arg Arg Leu Trp Lys Asp Tyr Phe Pro Glu Val Asn Gly
1               5                    10

Ile Val Ala Leu Gly Leu Leu Asn Thr Thr Leu Lys Asn
    15               20                 25

Asp Arg Leu Ala Lys His Gly Lys Leu Leu Phe Leu Lys

```
                  30                  35
Asp Val Pro Phe Val Ile Leu
 40                  45

(2) INFORMATION FOR SEQ ID NO:3:

(i) SEQUENCE CHARACTERISTICS:
        (A) LENGTH: 16
        (B) TYPE: AMINO ACID
        (C) STRANDEDNESS: UNKNOWN
        (D) TOPOLOGY: UNKNOWN (xi) SEQUENCE DESCRIPTION: SEQ ID NO:3:

Arg Pro Leu Trp Arg His Tyr Phe Gln Asn Thr Gln Gly
 1               5                  10

Leu Ile Phe
    15

(2) INFORMATION FOR SEQ ID NO:4:

(i) SEQUENCE CHARACTERISTICS:
        (A) LENGTH: 16
        (B) TYPE: AMINO ACID
        (C) STRANDEDNESS: UNKNOWN
        (D) TOPOLOGY: UNKNOWN (xi) SEQUENCE DESCRIPTION: SEQ ID NO:4:

Lys Arg Leu Trp Lys Asp Ser Gly Val Gln Ala Cys Phe
 1               5                  10

Asn Arg Ser
    15

(2) INFORMATION FOR SEQ ID NO:5:

(i) SEQUENCE CHARACTERISTICS:
        (A) LENGTH: 16
        (B) TYPE: AMINO ACID
        (C) STRANDEDNESS: UNKNOWN
        (D) TOPOLOGY: UNKNOWN (xi) SEQUENCE DESCRIPTION: SEQ ID NO:5:

Ser Ala Met Arg Asp Gln Tyr Met Arg Thr Gly Glu Gly
 1               5                  10

Phe Leu Cys
    15

(2) INFORMATION FOR SEQ ID NO:6:

(i) SEQUENCE CHARACTERISTICS:
        (A) LENGTH: 16
        (B) TYPE: AMINO ACID
        (C) STRANDEDNESS: UNKNOWN
        (D) TOPOLOGY: UNKNOWN (xi) SEQUENCE DESCRIPTION: SEQ ID NO:6:

Arg Thr Ile Thr Ser Ser Tyr Tyr Arg Gly Ala His Gly
 1               5                  10

Ile Ile Val
    15

(2) INFORMATION FOR SEQ ID NO:7:

(i) SEQUENCE CHARACTERISTICS:
        (A) LENGTH: 16
        (B) TYPE: AMINO ACID
```

-continued

```
            (C) STRANDEDNESS:  UNKNOWN
            (D) TOPOLOGY:  UNKNOWN (xi) SEQUENCE DESCRIPTION: SEQ ID NO:7:

Arg Thr Ile Thr Thr Ala Tyr Tyr Arg Gly Ala Met Gly
 1               5                  10

Ile Ile Leu
     15

(2) INFORMATION FOR SEQ ID NO:8:

(i) SEQUENCE CHARACTERISTICS:
            (A) LENGTH:  8
            (B) TYPE:  AMINO ACID
            (C) STRANDEDNESS:  UNKNOWN
            (D) TOPOLOGY:  UNKNOWN (xi) SEQUENCE DESCRIPTION: SEQ ID NO:8:

Lys Asp Ile Lys Leu Leu Leu Leu
 1               5

(2) INFORMATION FOR SEQ ID NO:9:

(i) SEQUENCE CHARACTERISTICS:
            (A) LENGTH:  15
            (B) TYPE:  AMINO ACID
            (C) STRANDEDNESS:  UNKNOWN
            (D) TOPOLOGY:  UNKNOWN (xi) SEQUENCE DESCRIPTION: SEQ ID NO:9:

Ala Arg Leu Trp Thr Glu Tyr Phe Val Ile Ile Asp Asp
1                5                   10

Asp Cys
     15
```